United States Patent
Kimura et al.

[11] Patent Number: 6,092,420
[45] Date of Patent: Jul. 25, 2000

[54] ULTRASONIC FLAW DETECTOR APPARATUS AND ULTRASONIC FLAW-DETECTION METHOD

[75] Inventors: Tomonori Kimura; Shusou Wadaka; Shumpei Kameyama; Mitsuhiro Koike; Yuuichi Manome, all of Tokyo, Japan

[73] Assignee: Mitsubishi Denki Kabushiki Kaisha, Tokyo, Japan

[21] Appl. No.: 08/860,277

[22] PCT Filed: Feb. 12, 1997

[86] PCT No.: PCT/JP97/00362

§ 371 Date: Jun. 17, 1997

§ 102(e) Date: Jun. 17, 1997

[87] PCT Pub. No.: WO97/36175

PCT Pub. Date: Oct. 2, 1997

[30] Foreign Application Priority Data

| Mar. 28, 1996 | [JP] | Japan | 8-074405 |
| May 10, 1996 | [JP] | Japan | 8-116528 |
| Oct. 23, 1996 | [JP] | Japan | 8-280839 |

[51] Int. Cl.[7] .................................................. G01N 29/04
[52] U.S. Cl. .............................................. 73/620; 73/599
[58] Field of Search ............................. 73/599, 602, 618, 73/619, 620, 624, 627, 628, 1.82

[56] References Cited

U.S. PATENT DOCUMENTS

| 4,497,210 | 2/1985 | Uchida | 73/602 |
| 4,537,073 | 8/1985 | Oshiro et al. | |
| 4,597,292 | 7/1986 | Fujii | 73/599 |
| 4,949,310 | 8/1990 | Smith | 73/628 |
| 4,993,416 | 2/1991 | Ophir | 73/599 |
| 5,524,626 | 6/1996 | Liu | 73/599 |

OTHER PUBLICATIONS

"Ultrasonic Flaw Detection Technique", published by Nikkon–Kogyo Newspaper on Dec. 20, 1977, publisher Hajima Takashiro, in Japanese.

Primary Examiner—Hezron Williams
Assistant Examiner—Helen C. Kwok

[57] ABSTRACT

An ultrasonic flaw detection apparatus is equipped with a probe which is driven by a transmission signal and which transmits an ultrasonic pulse at an angle with respect to a surface of a test object. The probe receives an ultrasonic pulse, which has been reflected by a defect in the test object, as an echo. The apparatus further includes a scanner for scanning the probe over a predetermined scanning zone on the test object and for outputting a spatial position of the probe. The apparatus is further equipped with a transmitter-receiver which has a transmitter for generating a transmission signal and outputting the transmission signal to the probe, a position detector for receiving a spatial position of the probe from the scanner, and a signal processor for detecting the defect according to the stored spatial position of the probe and the stored echo, taking the spread of an ultrasonic beam attributable to diffraction into account. The apparatus makes it possible to improve the accuracy of an examination based on an ultrasonic wave through a test object, and also to improve the capability of detection and the accuracy of measurement of the shape, size, position, etc. of an acoustically disconnected portion (defect).

32 Claims, 47 Drawing Sheets

FIG. 73

| | PROPAGATION MODE FROM TRANSMITTING PROBE TO BOTTOM | PROPAGATION MODE FROM BOTTOM TO DEFECT | PROPAGATION MODE FROM DEFECT TO RECEIVING PROBE | CONDITION FOR EXISTENCE | REMARK | |
|---|---|---|---|---|---|---|
| | | | | | MODE CONVERSION AT BOTTOM | MODE CONVERSION AT DEFECT |
| PROPAGATION MODE IN PROPAGATION PATH I | LONGITUDINAL WAVE | TRANSVERSE WAVE | TRANSVERSE WAVE | $\theta LLa \leq \theta L2'a \leq \theta LHa$ $\theta SLb \leq \theta S1b \leq \theta SHb$ | YES | NO |
| PROPAGATION MODE IN PROPAGATION PATH II | LONGITUDINAL WAVE | LONGITUDINAL WAVE | TRANSVERSE WAVE | $\theta LLa \leq \theta L2a \leq \theta LHa$ $\theta SLb \leq \theta S1b \leq \theta SHb$ | NO | YES |
| PROPAGATION MODE IN PROPAGATION PATH III | LONGITUDINAL WAVE | TRANSVERSE WAVE | LONGITUDINAL WAVE | $\theta LLa \leq \theta L2'a \leq \theta LHa$ $\theta LLb \leq \theta L1b \leq \theta LHb$ | YES | YES |
| PROPAGATION MODE IN PROPAGATION PATH IV | LONGITUDINAL WAVE | LONGITUDINAL WAVE | LONGITUDINAL WAVE | $\theta LLa \leq \theta L2a \leq \theta LHa$ $\theta LLb \leq \theta L1b \leq \theta LHb$ | NO | NO |

FIG. 74

| | PROPAGATION MODE FROM TRANSMITTING PROBE TO DEFECT | PROPAGATION MODE FROM DEFECT TO BOTTOM | PROPAGATION MODE FROM BOTTOM TO RECEIVING PROBE | CONDITION FOR EXISTENCE | REMARK | |
|---|---|---|---|---|---|---|
| | | | | | MODE CONVERSION AT BOTTOM | MODE CONVERSION AT IMPERFECTION |
| PROPAGATION MODE IN PROPAGATION PATH V | LONGITUDINAL WAVE | TRANSVERSE WAVE | TRANSVERSE WAVE | $\Theta LLa \leq \Theta L1a \leq \Theta LHa$ $\Theta SLb \leq \Theta S2b \leq \Theta SHb$ | NO | YES |
| PROPAGATION MODE IN PROPAGATION PATH VI | LONGITUDINAL WAVE | LONGITUDINAL WAVE | TRANSVERSE WAVE | $\Theta LLa \leq \Theta L1a \leq \Theta LHa$ $\Theta SLb \leq \Theta S2'b \leq \Theta SHb$ | YES | NO |
| PROPAGATION MODE IN PROPAGATION PATH VII | LONGITUDINAL WAVE | TRANSVERSE WAVE | LONGITUDINAL WAVE | $\Theta LLa \leq \Theta L1a \leq \Theta LHa$ $\Theta LLb \leq \Theta L2'b \leq \Theta LHb$ | YES | YES |
| PROPAGATION MODE IN PROPAGATION PATH VIII | LONGITUDINAL WAVE | LONGITUDINAL WAVE | LONGITUDINAL WAVE | $\Theta LLa \leq \Theta L1a \leq \Theta LHa$ $\Theta LLb \leq \Theta L2b \leq \Theta LHb$ | NO | NO |

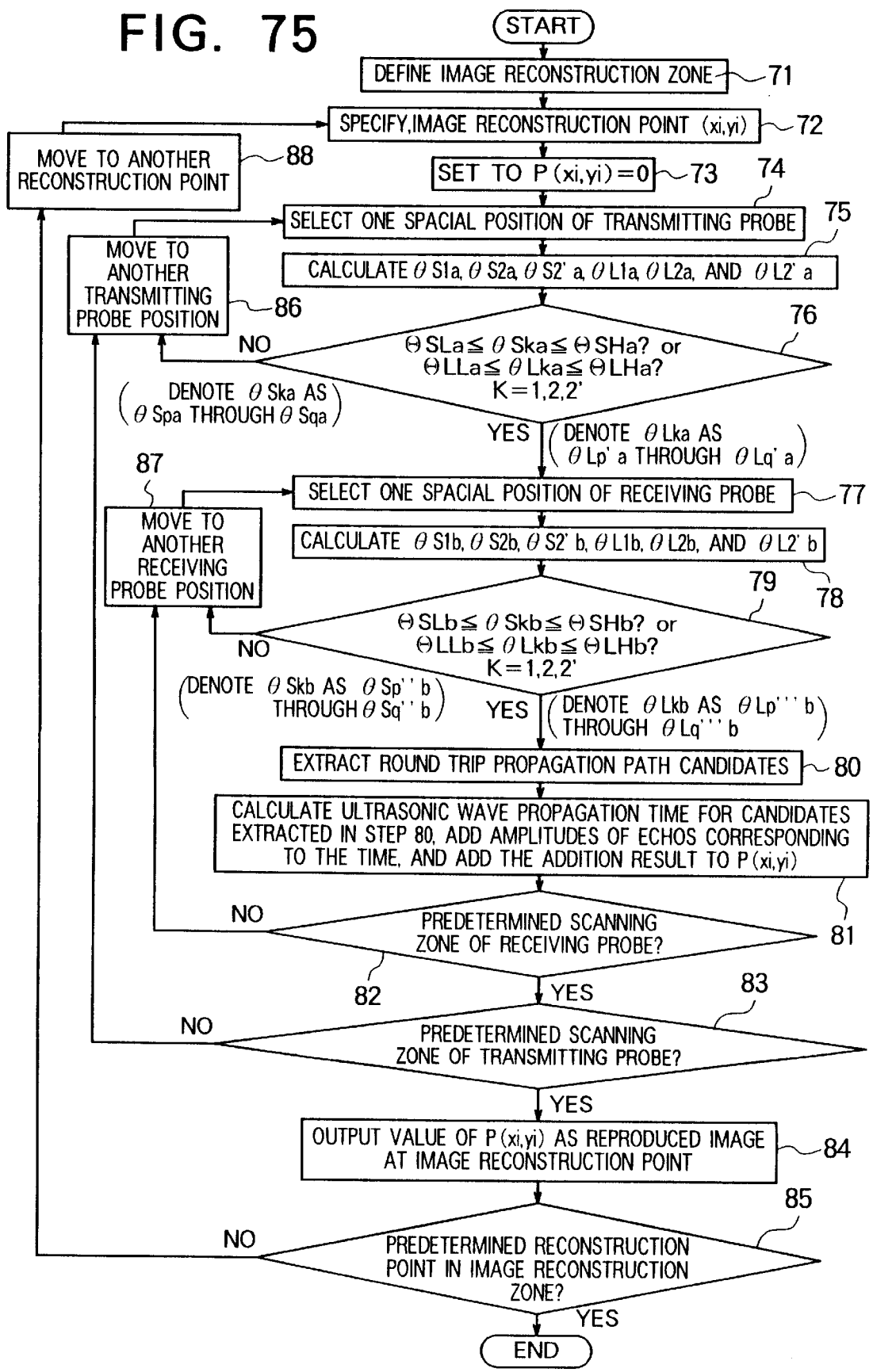

ULTRASONIC FLAW DETECTOR APPARATUS AND ULTRASONIC FLAW-DETECTION METHOD

This application is the national phase under 35 U.S.C § of PCT International Application No. PCT/JP97/00362 which has an International filing date of Feb. 12, 1997 which designates the United States of America.

TECHNICAL FIELD

The present invention relates to an ultrasonic flaw detection apparatus and an ultrasonic flaw detection technique used for examining a weld or examining plate materials, tubing materials, etc.

More particularly, the present invention relates to a so-called ultrasonic angle-beam flaw detection technique which employs ultrasonic waves which advance at a slanted angle with respect to a test surface of an object to be examined. There is such a term as measurement which is distinguished from such a term as examination or detection; however, the term, measurement, herein is handled so that it is included in the term, examination or detection. Likewise, the term, examination results, include such terms as test results and flaw detection results.

BACKGROUND ART

Hitherto, this type of ultrasonic angle-beam flaw detection technique has been described in detail on, for example, pages 180 to 199 of "Ultrasonic Flaw Detection Technique (revised new publication)" edited by Steelmaking Committee No. 19, Japan Society for the Promotion of Science, published by THE NIKKAN KOGYO SHIMBUN LTD., a revised new edition thereof being published on Jul. 30, 1974 and the third impression of a revised new edition thereof being published on Dec. 20, 1977 (hereinafter referred to as "Literature A").

Referring to FIG. 80, conventional ultrasonic flaw detection apparatus and ultrasonic flaw detection technique will be described. FIG. 80 is a diagram illustrative of a conventional ultrasonic angle-beam flaw detection technique cited from the foregoing literature A.

In FIG. 80, a test object 1 has a base material member 2, a surface 3, a bottom 4, and a weld 5. An acoustically discontinued portion (defect) 6 is present in the weld 5 of the test object 1. The acoustically discontinued portion 6 comes in various types including a crack in a first pass weld at the time of welding, a crater crack at a welding start or end, defective fusion, poor penetration, slag contamination, a blowhole, a wormhole, a hot crack, and a difference in material from a peripheral medium due to foreign substance contamination. Further, the acoustically discontinued portions also include spots contaminated by foreign substances, cracks, flaws, etc. which already exist in materials themselves irrespective of the welding operation. For the purpose of simplicity, these acoustically discontinued portions will be referred to as the defect 6 in the following description. In the drawing, a probe 7 is rested on the surface 3 of the test object 1.

An ultrasonic pulse is transmitted into the test object 1 from the probe 7 placed on the surface 3 of the test object 1 which corresponds to a test surface. In the drawing, the propagating direction of the ultrasonic pulse is indicated by a solid line with arrows; an angle "θ" denotes the refraction angle of the ultrasonic beam. An echo resulting from the irradiation to the defect 6 is reflected back and received by the probe 7.

The defect 6 is detected as follows. Although it is not shown, an ultrasonic flaw detector which is electrically connected to the probe 7 measures the difference between the time when the ultrasonic pulse is transmitted from the probe 7 and the time when the returning echo is received, that is, the time required for the ultrasonic pulse to propagate through the test object 1. The time required for the ultrasonic pulse to make a round trip between the probe 7 and the defect 6 is divided by two to determine the time required for one way propagation and then the determined time for one way propagation and the one way velocity of sound in the test object 1 are used to acquire the beam path length. The beam path length is denoted by "Wy" in the drawing.

As shown in the drawing, if the thickness of the test object 1 is denoted by "t", then a horizontal distance "y" and a depth "d" from the surface 3 of the test object 1 to the defect 6 can be determined by equation 1 and equation 2 shown below.

$$y = Wy \times \sin(\theta) \quad \text{Equation 1}$$

$$d = 2t - Wy \times \cos(\theta) \quad \text{Equation 2}$$

Equation 2 for determining the depth d applies when the ultrasonic pulse transmitted from the probe 7 is reflected once on the bottom 4 of the test object 1 and applied to the defect 6. If the ultrasonic pulse transmitted from the probe 7 is directly applied to the defect 6 without using the reflection on the bottom and the echo is directly received, then the following equation 3 which holds according to a similar geometrical relationship will be used:

$$d = Wy \times \cos(\theta) \quad \text{Equation 3}$$

Although not illustrated, if the ultrasonic pulse is repeatedly reflected a few times on the bottom 4 or the surface 3 of the test object 1 before it is applied to the defect 6 before the echo is received, then an equation which also holds according to a similar geometrical relationship will be used.

In the ultrasonic angle-beam flaw detection technique, transverse waves are often employed as the ultrasonic waves propagating through the test object 1. However, there are some cases where longitudinal waves are employed as disclosed in, for examples, Japanese Examined Patent Publication No. 55-36108, Japanese Examined Patent Publication No. 56-17024, Japanese Unexamined Patent Publication No. 53-74485, Japanese Examined Patent Publication No. 57-1788, Japanese Unexamined Patent Publication No. 61-169760, Japanese Unexamined Patent Publication No. 61-239158, and Japanese Unexamined Patent Publication No. 63-261156.

Furthermore, FIG. 80 illustrates a single probe technique wherein the single probe 7 transmits and receives the ultrasonic waves. However, there is also a double probe technique wherein separate probes are used for transmitting and receiving, respectively, as disclosed in, for example, Japanese Unexamined Patent Publication No. 62-222160, Japanese Unexamined Patent Publication No. 60-73453, Japanese Unexamined Patent Publication No. 64-59152, Japanese Unexamined Patent Publication No. 5-322857, Japanese Unexamined Patent Publication No. 7-120439, Japanese Examined Patent Publication No. 57-51062, Japanese Unexamined Patent Publication No. 55-13845, and Japanese Unexamined Patent Publication No. 5-288722.

Furthermore, there has been known a technique wherein an array-shaped probe is employed for the probe 7 to change electronic scanning or the refraction angle θ as disclosed in, for example, Japanese Unexamined Patent Publication No.

57-141549, Japanese Examined Patent Publication No. 1-46027, Japanese Examined Patent Publication No. 5-84464, Japanese Examined Patent Publication No. 6-64017, Japanese Examined Patent Publication No. 6-64027, Japanese Examined Patent Publication No. 3-50989, Japanese Examined Patent Publication No. 4-16174, Japanese Unexamined Patent Publication No. 60-66159, Japanese Unexamined Patent Publication No. 64-57165, or Japanese Unexamined Patent Publication No. 7-229879, instead of mechanically scanning the surface 3 of the test object 1 by the probe 7 longitudinally and laterally manually or automatically to perform the detection of flaws.

There has been known still another method called a tandem probe technique which is a double probe technique based on mechanical scanning which employs two probes having the same refraction angle θ as disclosed in, for example, Japanese Unexamined Patent Publication No. 5-288722, Japanese Examined Patent Publication No. 62-28870, Japanese Unexamined Patent Publication No. 64-9361, or Japanese Unexamined Patent Publication No. 56-67750.

Every one of the techniques described above, however, ignores the fact that an ultrasonic beam diverges due to diffraction. All the foregoing methods carry out the detection of the defect 6 according to the above equations established from the geometrical relationships based only on the central axis of an ultrasonic beam to estimate the size of the defect 6 from the height of an echo. This has posed a problem with the accuracy of measurement of the shape, size, position, etc. of the defect 6.

There have been attempts to take advantage of the spread of the ultrasonic beams caused by diffraction in order to improve the measurement accuracy. Such attempts include, for instance, the methods utilizing a synthetic aperture signal processing which has been disclosed, for example, in Japanese Unexamined Patent Publication No. 2-278149, Japanese Unexamined Patent Publication No. 2-248855, or Japanese Unexamined Patent Publication No. 5-172789.

In these methods based on the synthetic aperture signal processing, however, the length of only one beam path based on direct scanning is considered for the ultrasonic beam which is emitted from the probe 7 to the defect 6 and reflected from the defect 6 back to the probe 7, and signals are processed according thereto. Hence, the problem with the accuracy of the measurement of the shape, the size, the position, etc. of the defect 6 still remains unsolved.

The conventional ultrasonic flaw detection apparatuses and ultrasonic flaw detection techniques described above ignore the fact that an ultrasonic beam diverges due to diffraction. They are designed to carry out the detection of the defect 6 according to the above equations established according to the geometrical relationships based only on the central axis of an ultrasonic beam to estimate the size of the defect 6 from the height of an echo, posing a problem in that the accuracy of measurement and detection of shape, size, position, etc. of the defect 6 is not very good.

In other conventional ultrasonic flaw detection apparatuses and ultrasonic flaw detection techniques, although the divergence attributable to the diffraction is considered, the length of only one beam path based on direct scanning is considered for the ultrasonic beam which is emitted from the probe 7 to the defect 6 and reflected from the defect 6 back to the probe 7, and signals are processed according thereto. Hence, there has been a problem in that the accuracy of measurement and detection of the shape, size, position, etc. of the defect 6 is not very good.

The present invention has been made with a view toward solving the problems described above, and it is an object of the present invention to provide an ultrasonic flaw detection apparatus and an ultrasonic flaw detection technique which permit higher accuracy of the examination performed by ultrasonic waves through a test object so as to permit improved capability of detection and higher accuracy of measurement of the shape, size, position, etc. of a detect or the like.

DISCLOSURE OF INVENTION

An ultrasonic flaw detection apparatus in accordance with the present invention is equipped with: a probe which is driven by a transmission signal, and which transmits an ultrasonic pulse at an angle with respect to a test surface of a test object and receives the ultrasonic pulse, which has been reflected by an acoustically discontinued portion in the test object, as an echo; scanning means for scanning the probe over a predetermined scanning zone on the test object and outputting a spatial position of the probe; and transmitting and receiving means for generating the transmission signal and outputting it to the probe, receiving the echo received from the probe and storing it, receiving and storing the spatial position of the probe when the ultrasonic pulse was transmitted from the scanning means and when the echo was received, and detecting the acoustically discontinued portion according to the spatial position of the probe and the echo with consideration given to the spread of an ultrasonic beam attributable to diffraction.

Further, an ultrasonic flaw detection apparatus in accordance with the present invention is equipped with: a probe which is driven by a transmission signal, and which transmits an ultrasonic pulse at an angle with respect to a test surface of a test object and receives the ultrasonic pulse, which has been reflected by an acoustically discontinued portion in the test object, as an echo; a scanning means for scanning the probe over a predetermined scanning zone on the test object and outputting a spatial position of the probe; and transmitting and receiving means for generating the transmission signal and outputting it to the probe, receiving the echo received from the probe and storing it, receiving and storing the spatial position of the probe from the scanning means when the ultrasonic pulse was transmitted and when the echo was received, and detecting the acoustically discontinued portion according to the spatial position of the probe and the echo with consideration given to the spread of an ultrasonic beam attributable to diffraction, and the mode conversion from a longitudinal wave to a transverse wave and the mode conversion from a transverse wave to a longitudinal wave when the ultrasonic beam is reflected.

An ultrasonic flaw detection technique in accordance with the present invention includes the steps of: scanning a probe over a predetermined scanning zone on a test object by scanning means; generating a transmission signal and outputting it to the probe and transmitting an ultrasonic pulse at an angle with respect to a test surface of the test object by the probe; receiving the ultrasonic pulse, which has been reflected by an acoustically discontinued portion in the test object, as an echo by the probe; receiving the echo received from the probe and storing it, and receiving and storing the spatial position of the probe from the scanning means when the ultrasonic pulse was transmitted and when the echo was received; and detecting the acoustically discontinued portion according to the spatial position of the probe and the echo with consideration given to the spread of an ultrasonic beam attributable to diffraction.

Furthermore, an ultrasonic flaw detection technique in accordance with the present invention includes the steps of:

scanning a probe over a predetermined scanning zone on a test object by scanning means; generating a transmission signal and outputting it to the probe and transmitting an ultrasonic pulse at an angle with respect to a test surface of the test object by the probe; receiving the ultrasonic pulse, which has been reflected by an acoustically discontinued portion in the test object, as an echo by the probe; receiving the echo received from the probe and storing it, and receiving and storing the spatial position of the probe from the scanning means when the ultrasonic pulse was transmitted and when the echo was received; and detecting the acoustically discontinued portion according to the spatial position of the probe and the echo with consideration given to the spread of an ultrasonic beam attributable to diffraction, and the mode conversion from a longitudinal wave to a transverse wave and the mode conversion from a transverse wave to a longitudinal wave which take place when the ultrasonic beam is reflected.

BRIEF DESCRIPTION OF DRAWINGS

FIG. 73 is a diagram showing the propagation mode of an ultrasonic beam propagation path for describing the operation of the ultrasonic flaw detection apparatus according to the fourth embodiment of the present invention;

FIG. 74 is a diagram showing the propagation mode of an ultrasonic beam propagation path for describing the operation of the ultrasonic flaw detection apparatus according to the fourth embodiment of the present invention;

FIG. 75 is a flowchart for describing the signal processing of the ultrasonic flaw detection apparatus according to the fourth embodiment of the present invention;

BEST MODES FOR CARRYING OUT THE INVENTION

Figure 1:
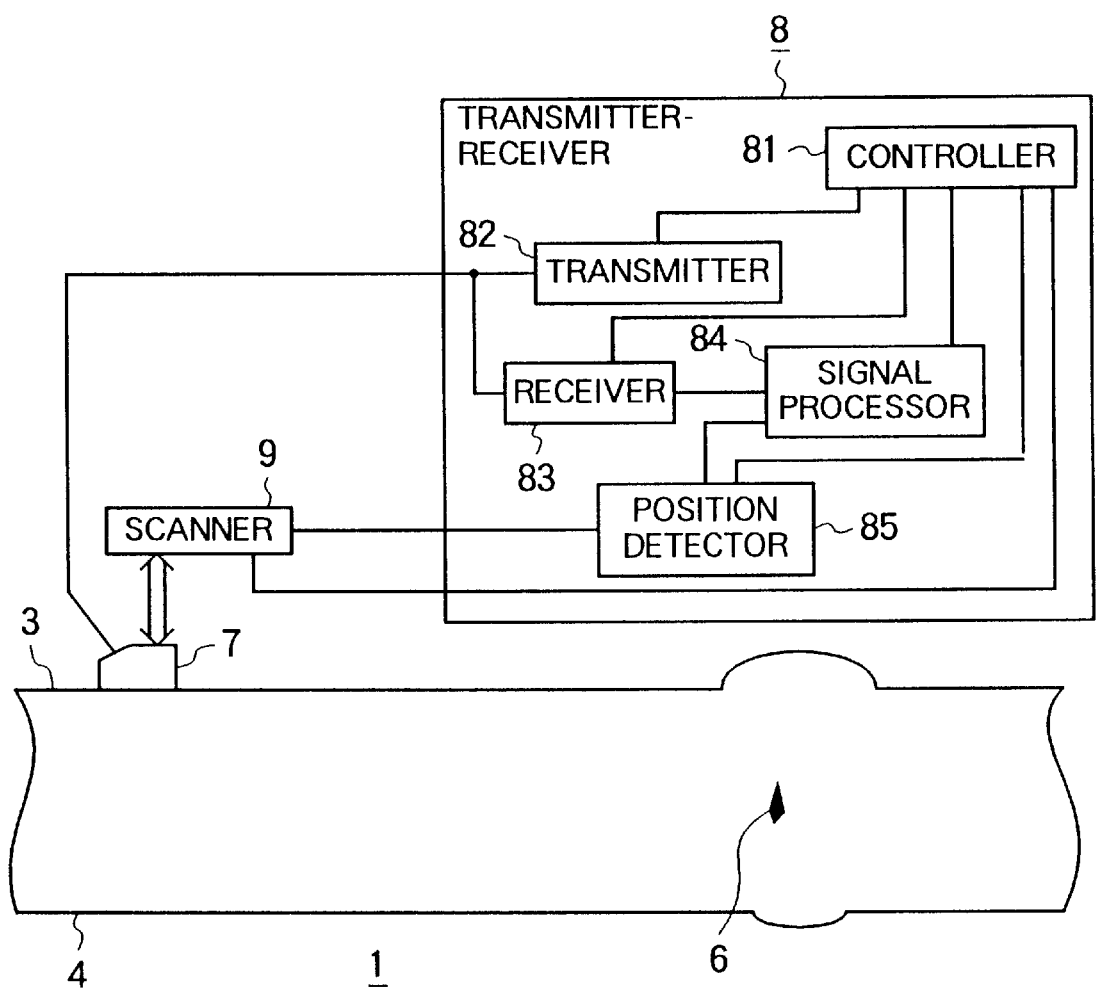
FIG. 1 is a diagram showing the configuration of an ultrasonic flaw detection apparatus according to a first embodiment of the present invention.
Figure 2:
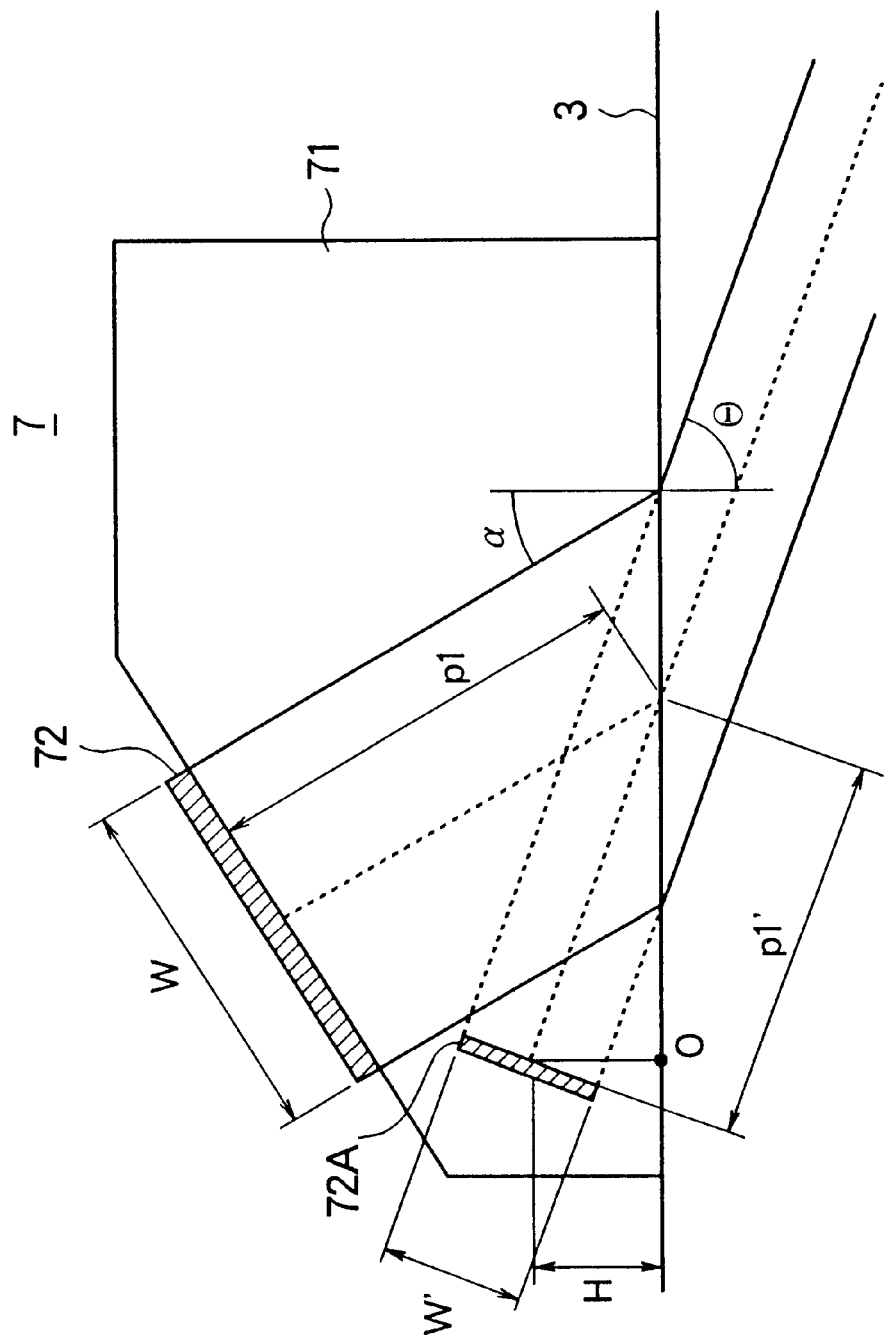
FIG. 2 is a diagram showing the configuration of a probe of the ultrasonic flaw detection apparatus according to the first embodiment of the present invention.
Figure 3:
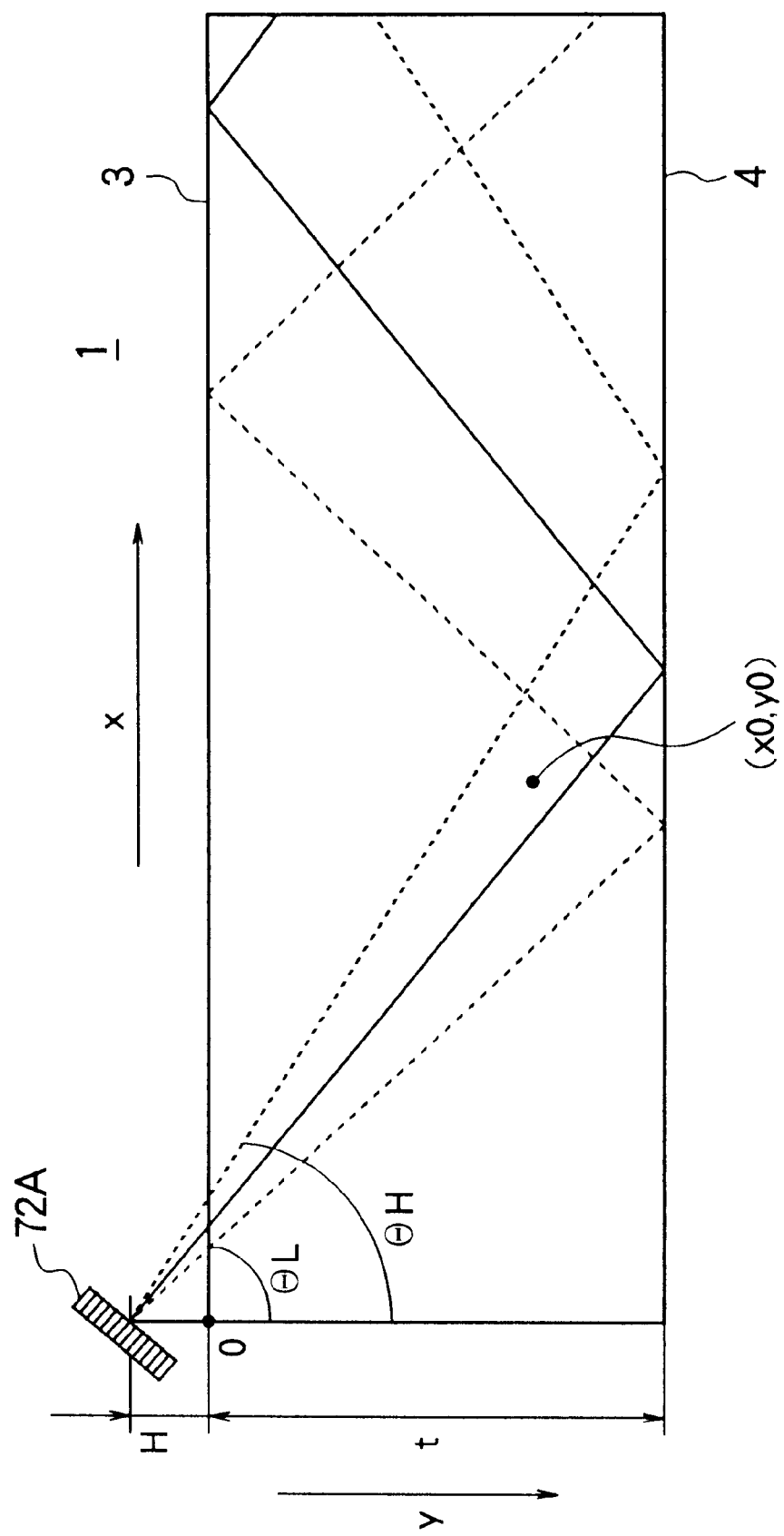
FIG. 3 is a diagram showing a propagation path of an ultrasonic beam for describing the operation of the ultrasonic flaw detection apparatus according to the first embodiment of the present invention.

The embodiments of the present invention will now be described in conjunction with the accompanying drawings.
First Embodiment Referring to FIG. 1 and FIG. 2, the configuration of an ultrasonic flaw detection apparatus according to a first embodiment of the present invention will be described. FIG. 1 is a block diagram showing the configuration of the ultrasonic flaw detection apparatus according to the first embodiment of the present invention. FIG. 2 is a diagram showing the configuration of a probe of the ultrasonic flaw detection apparatus according to the first embodiment. FIG. 2 provides a citation from pages 291 to 292 of "New Non-Destructive Inspection Handbook" edited by The Japanese Society for Non-Destructive Inspection and published by THE NIKKAN KOGYO SHIMBUN LTD. on Oct. 15, 1992 (hereinafter referred to as "literature B"). In the drawing, like reference numerals denote like or corresponding parts.

In FIG. 1, the ultrasonic flaw detection apparatus is equipped with a probe 7 rested on a test object 1, a transmitter-receiver 8 connected to the probe 7, and a scanner 9 for the probe 7.

Further in the drawing, the transmitter-receiver 8 includes a controller 81, a transmitter 82, a receiver 83, a signal processor 84, and a position detector 85 for detecting the position of the probe 7. The scanner 9 includes a sensor for detecting the position of the probe 7 although it is not shown.

In the drawing, the probe 7 is connected to the transmitter 82 and the receiver 83 by a signal conductor. The receiver 83 is connected to the signal processor 84. The position detector 85 is connected to the signal processor 84. The controller 81 is connected to the transmitter 82, the receiver 83, the signal processor 84, the position detector 85, and the scanner 9.

Further in the drawing, the scanner 9 is connected to the position detector 85. The output signal from the position detecting sensor of the scanner 9 is supplied to the position detector 85. The information on the position of the probe 7 detected by the position detector 85 is supplied to the signal processor 84.

The signal processor 84 has an internal memory (not shown). Various results obtained by operations and calculations are stored in this memory as needed, and the input signals supplied to the signal processor 84 are also stored therein as needed.

Furthermore, although not shown, the signal processor 84 furnishes signals which indicate processing states to the controller 81 as needed. Based on the input signals, the controller 81 issues control signals to the transmitter 82, the receiver 83, the signal processor 84, the position detector 85, and the scanner 9 to control these elements.

In FIG. 2, the probe 7 includes a wedge 71 composed of a material such as acrylic material, and a rectangular or circular transducer 72 composed of a piezoelectric material such as piezoelectric ceramic. Reference numeral 72A denotes an apparent transducer, and "H" denotes the height from the surface 3 of the test object 1 to the center of the transducer 72A. Further, "W" denotes the width of the transducer 72, "W'" denotes the width of the apparent transducer 72A, "p1" denotes the distance in the wedge, "p1'" denotes the distance in the apparent wedge, "α" denotes the incident angle of an ultrasonic wave on the boundary surface between the wedge 71 and the surface 3 of the test object 1, and "Θ" denotes a refraction angle.

It should be noted that, for convenience in description, the reference numerals and designations used in this specification are different from those used in the foregoing literature B. The correspondence between this specification and literature B is as follows: the designations and reference numerals on the left side of an arrow (→) are those in literature B, while those on the right side thereof are used in the present specification. The height corresponding to that denoted by reference numeral H in the present specification is not contained in literature B. The position of origin O is different from that shown in literature B; it is defined as a point obtained by perpendicularly projecting the center of the apparent transducer 72A to the surface 3 of the test object 1 as shown in FIG. 2.

Height H of the transducer→Width W of the transducer 72 Apparent height HR of the transducer→Apparent width W' of the transducer 72

Distance l 1 in the wedge→Distance p1 in the wedge

Distance l 2 in the wedge converted to the distance in the test object → Apparent distance p1' in the wedge The expression "apparent" has been used as shown above. This is because, as described in literature B, an ultrasonic wave transmitted from the transducer 72 into the wedge 71 is refracted according to the Snell's law of refraction at the boundary surface with respect to the test object 1, namely, the surface 3; therefore, width W of the transducer 72 observed from the test object 1 seemingly becomes W' equivalently, and distance p1 in the wedge seemingly becomes p1' equivalently when it is converted to the distance in the test object 1. Employing these apparent physical quantities enables various types of calculations and signal processing to be achieved by handling the wedge 71 as if it were the test object 1. Thus, the following description will use the apparent transducer 72A, width W' thereof, apparent distance P1' in the wedge, and height H related to the center of the apparent transducer 72A.

Referring now to FIG. 3 through FIG. 15, the operation of the ultrasonic flaw detection apparatus according to the first embodiment of the present invention will be described.

Figure 12:
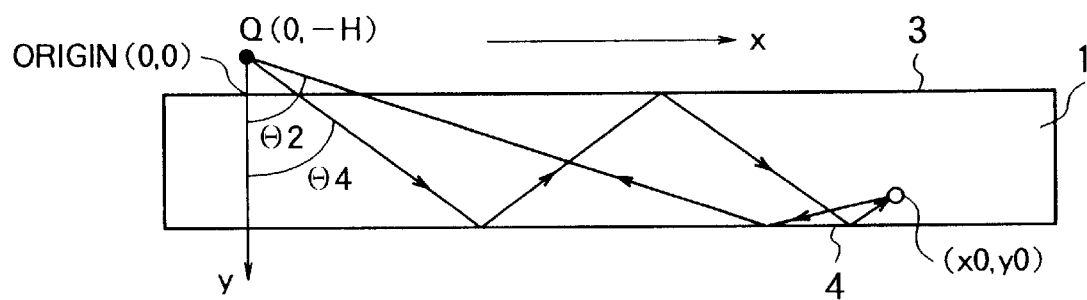
FIG. 12 is a diagram showing a propagation path of an ultrasonic beam for describing the operation of the ultrasonic flaw detection apparatus according to the first embodiment of the present invention.
Figure 13:
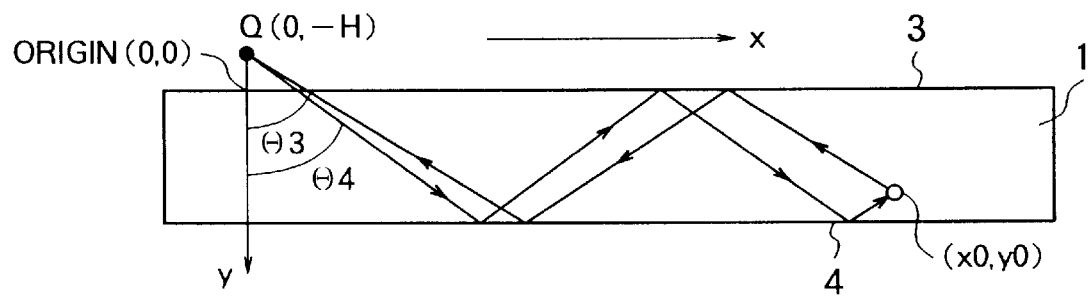
FIG. 13 is a diagram showing a propagation path of an ultrasonic beam for describing the operation of the ultrasonic flaw detection apparatus according to the first embodiment of the present invention.
Figure 14:
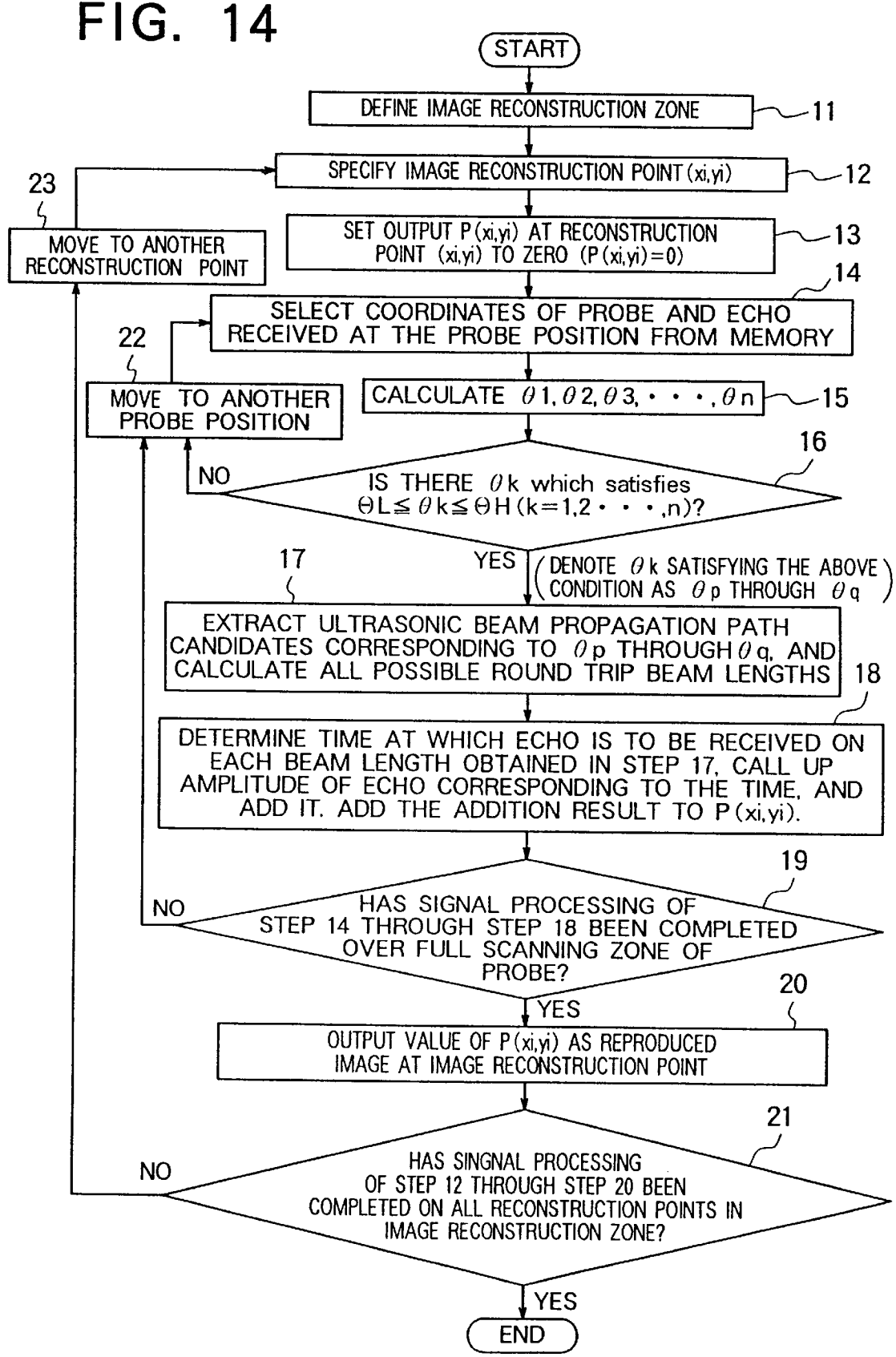
FIG. 14 is a flowchart for describing the signal processing of the ultrasonic flaw detection apparatus according to the first embodiment of the present invention.
Figure 15:
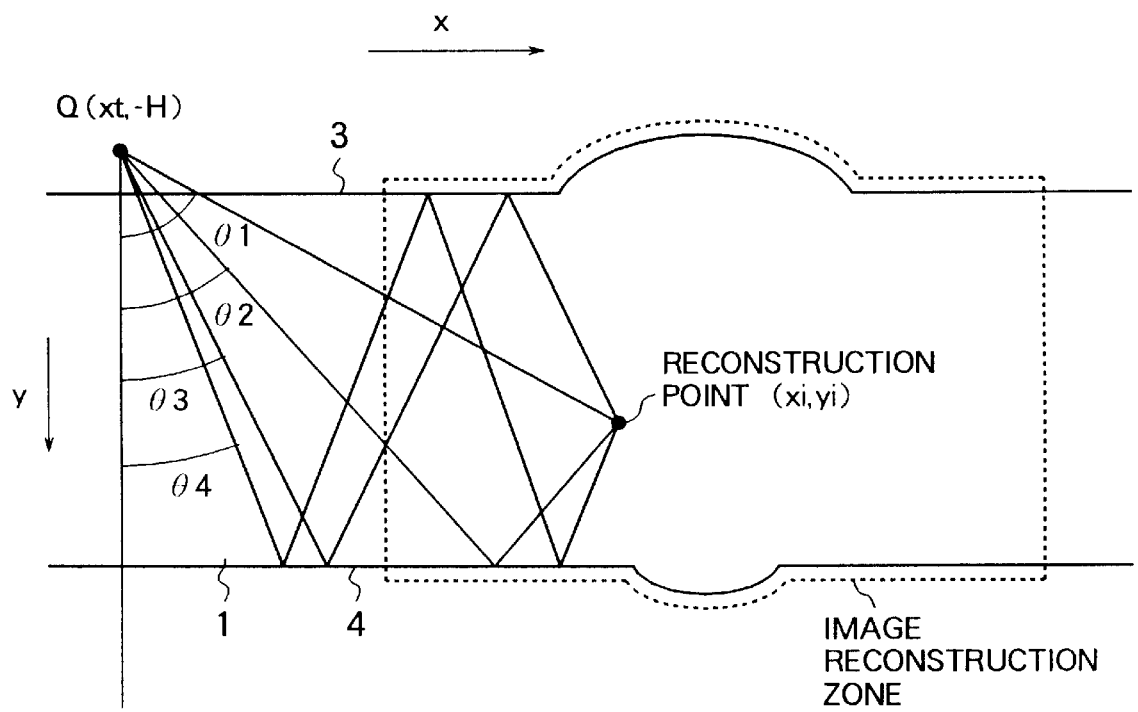
FIG. 15 is a diagram showing a beam propagation path for describing the signal processing of the ultrasonic flaw detection apparatus according to the first embodiment of the present invention.

FIG. 3 through FIG. 13 are diagrams illustrating the ultrasonic beam propagation paths for describing the operation of the ultrasonic flaw detection apparatus according to the first embodiment. FIG. 14 is a flowchart for describing the signal processing of the ultrasonic flaw detection apparatus according to the first embodiment. Further, FIG. 15 is a diagram illustrating the beam propagation path for describing the flowchart of the signal processing shown in FIG. 14.

A transmission signal such as a burst signal which has a certain carrier frequency or a narrow pulse which may be regarded as an impulse is generated and transmitted from the transmitter 82 of the transmitter-receiver 8 to the probe 7. The probe 7 is driven by the transmission signal; and transmits the ultrasonic pulse at an angle with respect to the test surface of the test object 1, i.e. the surface 3 of the test object 1. In the embodiments, the description will be given, taking the surface as the test surface as an example. The test surface, however, is not limited to a surface; it may be a bottom or side. The ultrasonic pulse propagates in the test object 1 and is reflected, scattered, and diffracted by the defect 6. The term "reflection" herein is handled as a term which includes such physical phenomena as scattering and diffraction in addition to reflection. This means that the term "reflection" should be interpreted as a term which includes all phenomena wherein ultrasonic waves are affected by the defect 6 and therefore behave differently in propagation from a case where no defect 6 is present. The description will be given, assuming that a distal end diffraction echo or a tip echo which is known to occur at a tip of the defect 6 is also included in the echos reflected by the defect 6. The reflected, scattered and diffracted ultrasonic pulse propagates through the test object 1 and is received by the probe 7. The received echo is amplified by the receiver 83 before it is sent to the signal processor 84.

The information on the spatial position of the probe 7 is detected by the scanner 9 and it is sent to the position detector 85. The information on the spatial position of the probe 7 is sent from the position detector 85 to the signal processor 84. The signal processor 84 stores the information on the spatial position of the probe 7 and the received echo.

Then, the probe 7 is moved by the scanner 9 to another spatial position (coordinates). And an ultrasonic pulse is transmitted from the probe 7 by the transmission signal, and the echo received from the defect 6 and the information on the spatial position of the probe 7 are transmitted to and stored in the signal processor 84 in the same manner as described above.

This series of operations is conducted over a predetermined scanning zone of the probe 7. After that, the signal processing to be discussed later is carried out in the signal processor 84.

Before describing the signal processing procedure in the signal processor 84, the propagating characteristic of the ultrasonic beam in the test object 1 will be described. First, the propagation path of the ultrasonic beam will be discussed with reference to FIG. 3. In the drawing, the horizontal direction is taken on an x-axis, while the vertical direction is taken on a y-axis.

It is assumed that a point reflection source which corresponds to the defect 6 is located at (x0, y0). An ultrasonic beam transmitted from the apparent transducer 72A diverges due to diffraction; in the drawing, the solid line indicates the centerline of the ultrasonic beam, while the dashed lines indicate the lines which connect the points at which the sound pressure is −6 dB in, for example, an overall ultrasonic beam on a round trip of transmission and reception, according to the sound pressure on the foregoing centerline. In other words, the zone defined by the two dashed lines corresponds to an effective beam width in the overall transmission and reception. The refraction angles corresponding to the two dashed lines are denoted as "Θ L" and "Θ H" as shown in the drawing. In this embodiment, the beam width of −6 dB is used, but it is not limited thereto; it may be −3 dB or −12 dB according to the application or purpose, or other value may be used to define the effective beam width.

Referring now to FIG. 4 through FIG. 9, the sound rays in the foregoing beam width will be discussed. In FIG. 4 through FIG. 9, an origin (0, 0) of the coordinates is established at a point where the center of the apparent transducer 72A is projected onto the surface 3 of the test object 1 along the y-axis as in the case of FIG. 2. Point Q denotes the center of the apparent transducer 72A; the coordinates thereof is (0, −H). A blank circle mark located at (x0, y0) denotes a reflection source which corresponds to the defect 6.

Figure 4:
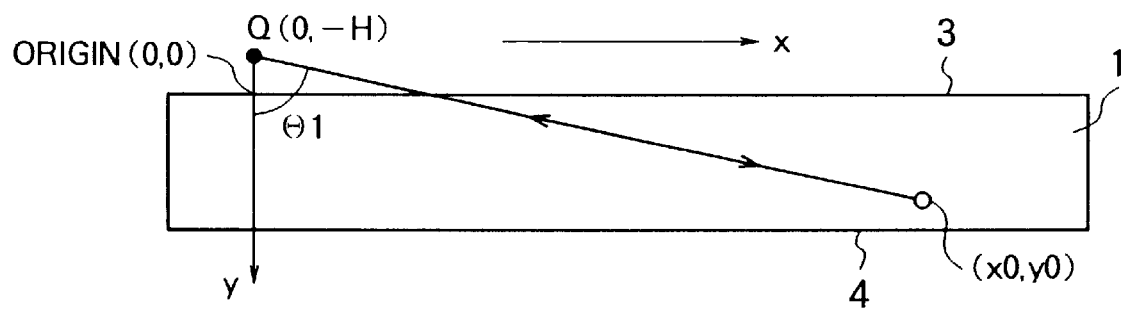
FIG. 4 is a diagram showing a propagation path of an ultrasonic beam for describing the operation of the ultrasonic flaw detection apparatus according to the first embodiment of the present invention.

As shown in FIG. 4, if a sound ray equivalent to refraction angle Θ 1 exists in the foregoing beam width, that is, if Θ L≦Θ 1≦Θ H, then the propagation path of the ultrasonic beam indicated by the arrows may exist. At this time, the ultrasonic wave transmitted from the probe 7 is directly applied to the defect 6 and directly reflected, then received as an echo by the probe probe 7. In this case, Θ 1 is given by equation 4 shown below.

$$\Theta 1 = \tan^{-1}[x0/(y0+H)]$$ Equation 4

The overall length of the round trip beam path in this case is 2×L1, L1 being determined by equation 5 below; where SQRT [ ] denotes the arithmetic operation for determining the square root of the value in the bracket [ ].

$$L1 = SQRT[x0^2 + (y0+H)^2] \quad \text{Equation 5}$$

Figure 5:
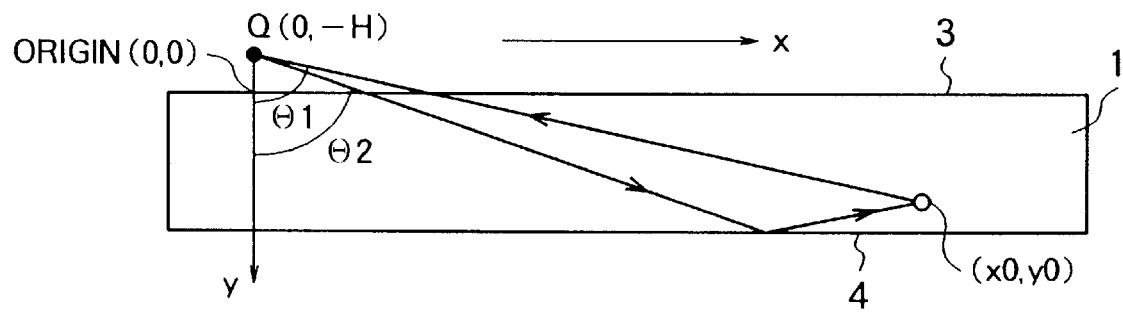
FIG. 5 is a diagram showing a propagation path of an ultrasonic beam for describing the operation of the ultrasonic flaw detection apparatus according to the first embodiment of the present invention.

As shown in FIG. 5, if a sound ray equivalent to refraction angle Θ 1 exists in the aforesaid beam width and a sound ray equivalent to refraction angle Θ 2 also exists in the beam width, that is, if Θ L≦Θ 1≦Θ H, and also Θ L≦Θ 2≦Θ H at the same time, then a propagation path may exist, in which the ultrasonic wave transmitted from the probe 7 is reflected once on the bottom 4 as indicated by the arrow before it hits the defect 6, then it is reflected by the defect 6 and it directly reaches the probe 7 to be received as an echo.

Although not shown, it is possible that a propagation path opposite from the one described above exists. More specifically, the ultrasonic wave transmitted from the probe 7 directly hits the defect 6; it is reflected by the defect 6 and reflected once on the bottom 4, then it reaches the probe 7 to be received as an echo. In this case, 2 is given by equation 6 shown below, "t" denoting the thickness of the test object 1.

$$\Theta 2 = \tan^{-1}[x0/(2t-y0+H)] \quad \text{Equation 6}$$

The total beam path length in the two cases described above is L1+L2; L2 is given by equation 7 shown below.

$$L2 = SQRT[x0^2 + (2t-y0+H)^2] \quad \text{Equation 7}$$

Figure 6:
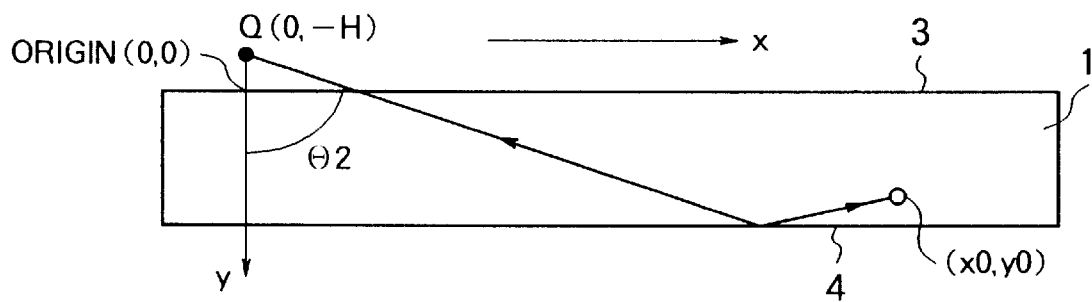
FIG. 6 is a diagram showing a propagation path of an ultrasonic beam for describing the operation of the ultrasonic flaw detection apparatus according to the first embodiment of the present invention.

Further, if Θ L≦Θ 2≦Θ H, then the propagation path shown in FIG. 6 may also exist. To be more specific, the ultrasonic wave transmitted from the probe 7 is reflected once on the bottom 4 as indicated by the arrow before it hits the defect 6; the ultrasonic wave reflected by the defect 6 is then reflected by the bottom 4 once and it reaches the probe 7 to be received as an echo. The total beam path length is 2×L2.

Figure 7:
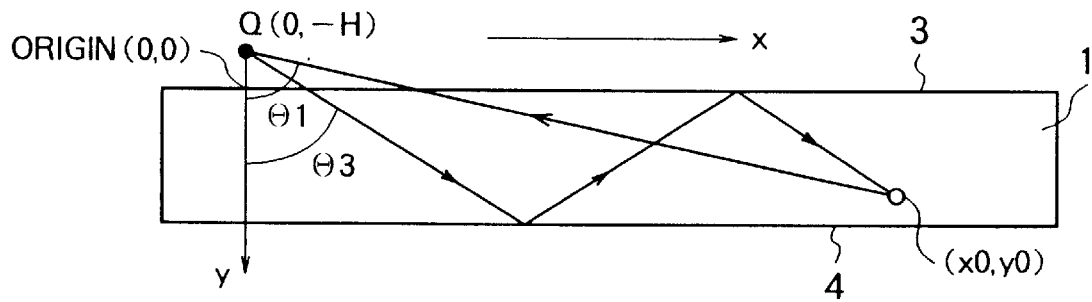
FIG. 7 is a diagram showing a propagation path of an ultrasonic beam for describing the operation of the ultrasonic flaw detection apparatus according to the first embodiment of the present invention.

As shown in FIG. 7, if a sound ray equivalent to refraction angle Θ 1 exists in the aforesaid beam width and a sound ray equivalent to refraction angle Θ 3 also exists in the beam width, that is, if Θ L≦Θ 1≦Θ H, and also Θ L≦Θ 3≦Θ H at the same time, then the following propagation path may exist.

Specifically, the ultrasonic wave transmitted from the probe 7 is reflected once on the bottom 4 and further reflected once on the surface 3 as indicated by the arrows before it hits the defect 6; then it is reflected by the defect 6 and it directly reaches the probe 7 to be received as an echo.

Although not shown, it is possible that a propagation path opposite from the one described above exists. More specifically, the ultrasonic wave transmitted from the probe 7 directly hits the defect 6; it is reflected by the defect 6 and reflected once on the surface 3, then it is reflected once on the bottom 4 before it reaches the probe 7 to be received as an echo. In this case, Θ 3 is given by equation 8 shown below.

$$\Theta 3 = \tan^{-1}[x0/(2t+y0+H)] \quad \text{Equation 8}$$

The total beam path length in the two cases described above is L1+L3; L3 is given by equation 9 shown below.

$$L3 = SQRT[x0^2 + (2t+y0+H)^2] \quad \text{Equation 9}$$

Figure 8:
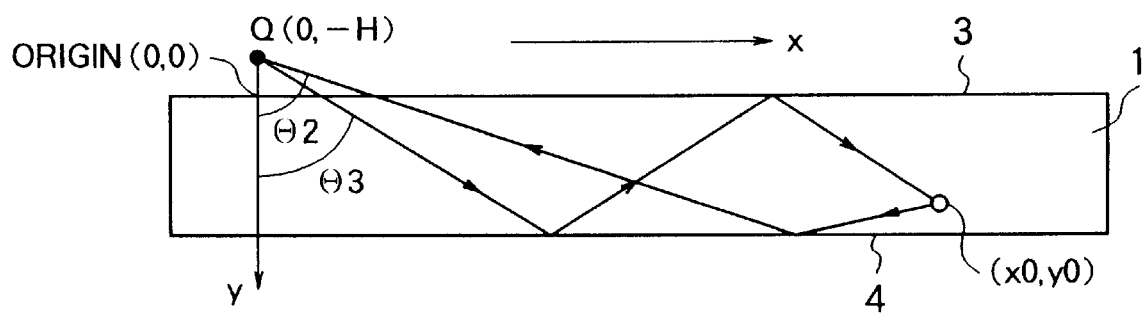
FIG. 8 is a diagram showing a propagation path of an ultrasonic beam for describing the operation of the ultrasonic flaw detection apparatus according to the first embodiment of the present invention.

There is a relationship Θ 3≦Θ 2≦Θ 1; therefore, if the sound ray equivalent to refraction angle Θ 1 exists in the aforesaid beam width and a sound ray equivalent to refraction angle Θ 3 also exists in the beam width, then Θ L≦Θ 2≦Θ H holds, so that the beam propagation path shown in FIG. 8 may exist.

Specifically, the ultrasonic wave transmitted from the probe 7 is reflected once on the bottom 4 and further reflected once on the surface 3 as indicated by the arrows before it hits the defect 6; then it is reflected by the defect 6 and it reaches the probe 7 to be received as an echo.

Although not shown, it is possible that a propagation path opposite from the one described above exists. More specifically, the ultrasonic wave transmitted from the probe 7 is reflected once on the bottom 4 before it hits the defect 6; then, the ultrasonic wave reflected by the defect 6 is reflected once on the surface 3, and it is reflected once on the bottom 4 before it reaches the probe 7 to be received as an echo. The total beam path length in the two cases described above is L2+L3.

Figure 9:
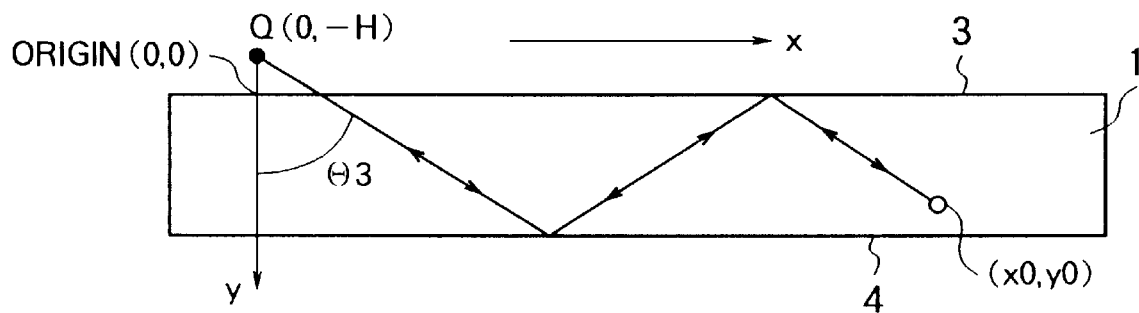
FIG. 9 is a diagram showing a propagation path of an ultrasonic beam for describing the operation of the ultrasonic flaw detection apparatus according to the first embodiment of the present invention.

Furthermore, if Θ L≦Θ 3≦Θ H, then the beam path shown in FIG. 9 may also exist. Specifically, the ultrasonic wave transmitted from the probe 7 is reflected once on the bottom 4 and further reflected once on the surface 3 before it hits the defect 6 as shown by the arrows; after it is reflected by the defect 6, it is reflected once on the surface 3 and further reflected once on the bottom 4 before it reaches the probe 7 to be received as an echo. The total beam path length in this case is 2×L3.

So far, for the purpose of simplifying the description, cases have been discussed where the sound rays up to those equivalent to refraction angle Θ 3 exist in the effective ultrasonic beam width. In other words, the cases have been discussed where the reflection takes place once on the bottom 4 and once on the surface 3 in a beam path.

Referring now to FIG. 10 through FIG. 13, cases will be discussed where the beam width is greater than that considered above.

Figure 10:
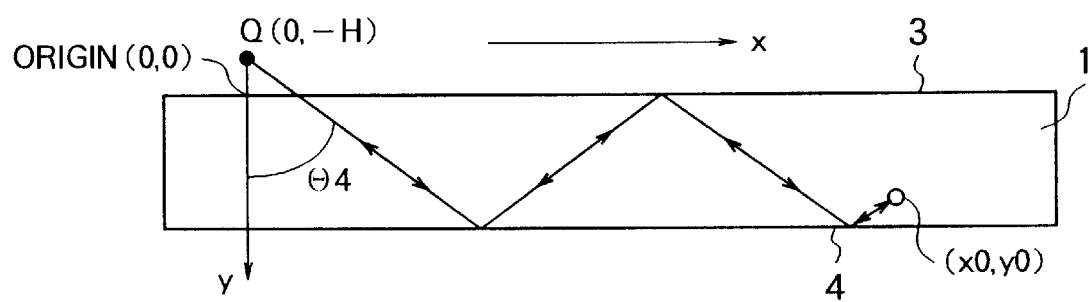
FIG. 10 is a diagram showing a propagation path of an ultrasonic beam for describing the operation of the ultrasonic flaw detection apparatus according to the first embodiment of the present invention.
Figure 11:
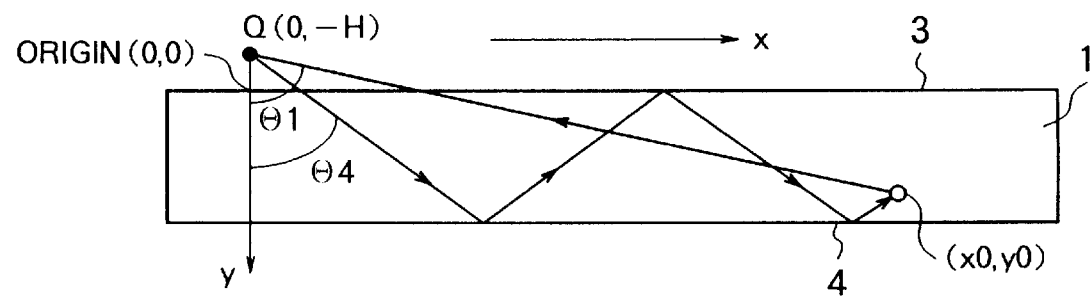
FIG. 11 is a diagram showing a propagation path of an ultrasonic beam for describing the operation of the ultrasonic flaw detection apparatus according to the first embodiment of the present invention.

In such a case, as illustrated in FIG. 10, it is necessary to contemplate a beam path wherein the ultrasonic wave transmitted from the probe 7 is reflected once on the bottom 4, then reflected once on the surface 3 and further reflected once on the bottom 4 before it hits the defect 6, and another beam path opposite from the above beam path. Hence, it is likely that there are various beam paths as shown in FIG. 11 through FIG. 13 and the opposite propagation paths from the above respective beam paths in addition to those illustrated in FIG. 4 through FIG. 9. In the drawings, Θ 4 is given by equation 10 given below.

$$\Theta 4 = \tan^{-1}[x0/(4t-y0+H)] \quad \text{Equation 10}$$

In FIG. 10, the paths are covered where the ultrasonic wave is reflected twice on the bottom 4 and once on the surface 3; however, when the beam width is even greater, it also required to consider another path wherein the ultrasonic wave reflects twice on the bottom 4 and twice on the surface 3 in total. Thus, as the beam width increases, the number of reflections on the bottom 4 and the surface 3 increases accordingly in the paths to be considered.

Thus, the first embodiment provides an apparatus and a method for detecting a flaw at an angle by taking the spread of an ultrasonic beam into account. This is one of the significant differences of the first embodiment from the conventional apparatuses and methods. Further, the first embodiment is entirely different from the prior art disclosed in Japanese Unexamined Patent Publication No. 2-278149, Japanese Unexamined Patent Publication No. 2-248855, or Japanese Unexamined Patent Publication No. 5-172789 in that it also considers the reflections on the surface 3 and the bottom 4.

Based on the consideration results concerning the beam paths discussed above, the signal processing procedure in the signal processor 84 will be described with reference to FIG. 14 and FIG. 15. The coordinate origin in FIG. 15 is different from those in FIG. 2 to FIG. 13. Obviously, the origin may be established anywhere. It is obvious that, if the origin is different from that when the probe 7 performs scanning, then the coordinate conversion must be implemented accordingly.

As previously mentioned, the memory of the signal processor 84 stores the echo waveforms at spatial (coordinate) points in the scanning zone when the predetermined scanning zone was scanned with the probe 7 and the information on the spatial positions (coordinates) of the probe 7 at the time when the echo waveforms were received. The echo waveforms are stored as raw waveforms, i.e. AC waveforms which have not been subjected to such processing as rectification or detection.

In step 11 in FIG. 14, a predetermined image reconstruction zone is decided. More specifically, in FIG. 15, a zone is defined where an image should be displayed as a result of the flaw detection of the test object 1 as indicated, for example, by the dotted line.

In step 12, an image reconstruction point is specified. The image reconstruction point is one point in the foregoing image reconstruction zone. The coordinates of this point are set to (xi, yi) as shown in FIG. 15.

In step 13, the output corresponding to the reconstruction point (xi, yi) is defined as P (xi, yi), and the value is set to zero. This means P (xi, yi)=0 for initialization.

In step 14, the spatial position, i.e. the coordinates, of the probe 7 and the echo waveform received at that position are selected from the memory. As shown in FIG. 15, the position of the probe 7 is represented by point Q, and the coordinates are assumed to be (xt, −H). The meaning of point Q is the same as in FIG. 4 through FIG. 13.

In step 15, the angles (refraction angles) $\theta 1$, $\theta 2$, $\theta 3$, ..., $\theta n$ shown in FIG. 15 are calculated. In this case, n is an integer; it is decided in advance according to the image reconstruction zone and the scanning zone of the probe 7, taking the effective beam width of the probe 7 into account. The angles of $\theta 1$ through $\theta n$ are given by the following equation 11, equation 12, equation 13, equation 14, and equation 15. The value of m is given as follows: if n is an even number, then m=n; if n is an odd number, then m=n−1.

$\theta 1 = \tan^{-1}[(xi-xt)/(yi+H)]$ Equation 11

$\theta 2 = \tan^{-1}[(xi-xt)/(2t-yi+H)]$ Equation 12

$\theta 3 = \tan^{-1}[(xi-xt)/(2t+yi+H)]$ Equation 13

$\theta 4 = \tan^{-1}[(xi-xt)/(4t-yi+H)]$ Equation 14

$\theta n = \tan^{-1}[(xi-xt)/(mt-(-1)^n yi+H)]$ Equation 15

If the image reconstruction point is tentatively regarded as the reflection source, and the beam path wherein an ultrasonic wave transmitted from the probe 7 reaches the image reconstruction point (xi, yi) and the length of one way of the beam path from the probe 7 to the image reconstruction point are considered accordingly, then these angles $\theta 1$ through $\theta n$ will be as shown below.

Angle $\theta 1$ corresponds to a path wherein the ultrasonic wave transmitted from the probe 7 is directly applied to the image reconstruction point (xi, yi). If the length of one way of the beam path in this case is taken as w1, then w1 is determined by equation 16 shown below:

$w1 = SQRT[(xi-xt)^2+(yi+H)^2]$ Equation 16

Angle $\theta 2$ corresponds to a beam path wherein the ultrasonic wave transmitted from the probe 7 is reflected once on the bottom 4 before it hits the image reconstruction point (xi, yi). If the length of one way of the beam path in this case is taken as w2, then w2 is determined by equation 17 shown below:

$w2 = SQRT[(xi-xt)^2+(2t-yi+H)^2]$ Equation 17

Angle $\theta 3$ corresponds to a beam path wherein the ultrasonic wave transmitted from the probe 7 is reflected once on the bottom 4 and then reflected once on the surface 3 before it hits the image reconstruction point (xi, yi). If the length of one way of the beam path in this case is taken as w3, then w3 is determined by equation 18 shown below:

$w3 = SQRT[(xi-xt)^2+(2t+yi+H)^2]$ Equation 18

Angle $\theta 4$ corresponds to a beam path wherein the ultrasonic wave transmitted from the probe 7 is reflected once on the bottom 4, then reflected once on the surface 3 and further reflected on the bottom 4 once again before it hits the image reconstruction point (xi, yi). If the length of one way of the beam path in this case is taken as w4, then w4 is determined by equation 19 shown below:

$wn = SQRT[(xi-xt)^2+(4t-yi+H)^2]$ Equation 19

The same applies to $\theta 5$ through $\theta n$ and the description therefor will be omitted because it can be inferred without the need for description in particular. If one way of the beam path corresponding to angle $\theta n$ is taken as wn, then wn is given by equation 20 shown below:

$wn = SQRT[(xi-xt)^2+(mt-(-1)^n yi+H)^2]$ Equation 20

The description above provides consideration given by associating angles $\theta 1$ through $\theta n$ with the beam paths wherein the ultrasonic waves transmitted from the probe 7 reach the image reconstruction point. Conversely, if beam paths, wherein the ultrasonic wave reflected at the image reconstruction point advances in the entirely opposite direction to reach the probe 7, are considered for the respective beam paths described above, then angles $\theta 1$ through $\theta n$ can be considered by bringing them into correspondence with these reflection-associated beam paths. Obviously, path lengths w1 to wn of the beam paths along which the ultrasonic wave transmitted from the probe 7 reaches the image reconstruction point are respectively equal to the lengths of the beam paths in the opposite directions from those of the aforesaid beam paths.

In step 16, it is determined whether angles $\theta 1$ through $\theta n$ obtained by the calculation in step 15 are within the effective beam width of the ultrasonic beam. Then, the angles which are in the effective beam width are selected among $\theta 1$ through $\theta n$. Specifically, $\theta k$ which satisfies the condition given by equation 21 below is selected, assuming that k is an integer from 1 to n.

$\theta L \leq \theta k \leq \theta H$ Equation 21

Those that have been selected as $\theta k$ satisfying the above condition are denoted as angles $\theta p$ through $\theta q$; p and q indicate integers falling in a range from 1 to n. If there is no $\theta k$ satisfying the aforesaid condition, then the program proceeds to step 22. The description of step 22 will be given later.

In step 17, the propagation paths of the aforesaid ultrasonic beams respectively associated with angles $\theta p$ through θ q, which have been selected in step 16, are extracted. More specifically, in respective angles θ p through θ q, the ultrasonic beam propagation paths along which the ultrasonic wave transmitted from the probe 7 reaches the image reconstruction point (xi, yi) (hereinafter referred to as "outbound propagation path") and the propagation paths opposite therefrom, i.e. the propagation paths along which the ultrasonic reflected at the image reconstruction point (xi, yi) reaches the probe 7 (hereinafter referred to as "outbound-back propagation path") are extracted. Further, path lengths wp through wq respectively corresponding to angles θ p through θ q are calculated.

Then, for each of angles θ p through θ q, all combinations of round trip propagation paths composed of the outbound propagation paths and the inbound propagation paths which have been drawn as described above are extracted, and the round trip beam path lengths are calculated. The round trip propagation paths refer to the propagation paths in which the ultrasonic wave transmitted from the probe 7 reaches the image reconstruction point (xi, yi) and it is reflected by the image reconstruction point, then the ultrasonic wave reflected at the image reconstruction point (xi, yi) reaches the probe 7. There may be a combination wherein the outbound propagation path corresponds to one angle among angles θ p through θ q and the inbound propagation path also corresponds to one angle among angles θ p through θ q; it is obvious that the angle corresponding to the outbound propagation path may be identical to the angle corresponding to the inbound propagation path in some combinations, or the angles may be different in other combinations.

Next, on all the combinations of the round trip propagation paths extracted as mentioned above, the round trip path lengths thereof are calculated according to wp through wq. Thus, every possible round trip path length should have been calculated.

In step 18, on each of all the round trip beam path lengths obtained in step 17, the time when the echo is to be received is determined according to the velocity of sound in the test object 1. Specifically, time =beam path length/sound velocity. Then, the amplitude of the echo corresponding to the time is called up. The echo is the echo waveform selected in step 14.

Next, the amplitudes of the echos called up for the respective round trip beam path lengths are added, and the result of the addition is added to P (xi, yi).

In step 19, it is determined whether the signal processing from step 14 through step 18 has been completed over the entire scanning zone of the probe 7 or over a predetermined scanning zone. If the determination result is negative, then the program goes to step 22; if it is affirmative, then the program proceeds to the next step 20.

In step 20, the value of P (xi, yi) or an absolute value thereof or a square value of the absolute value or the like is output as a reconstructed image at the image reconstruction point (xi, yi).

In step 21, it is determined whether the signal processing from step 12 through step 20 has been completed on all reconstruction points or predetermined reconstruction points in a predetermined image reconstruction zone. If the determination result is negative, then the program goes to step 23; if it is affirmative, then it means that all signal processing in the signal processor 84 has been completed.

In step 22, another spatial position (coordinates) in the scanning zone of the probe 7 is specified, and the signal processing from step 14 to step 19 is continued.

In step 23, another predetermined image reconstruction point (coordinates) in the predetermined image reconstruction zone is specified, and the signal processing from step 12 to step 21 is repeated. Thus, in step 18, the time when the echo is to be received has been determined on each of all the round trip beam path lengths and the amplitude of the echo corresponding to the time has been called up and added; attention should be paid to the following when carrying out the addition. When the ultrasonic wave is reflected once on the bottom 4, the phase changes. Likewise, when the ultrasonic wave is reflected on the surface 3, the phase also changes. It is necessary, therefore, to correct the change in the phase involved in the reflection when performing the addition. The following is an example wherein the phase changes to a reversed phase (180 degrees) when the reflection takes place. It is assumed, for instance, that there are such round trip beam paths as a path (first path) wherein the ultrasonic pulse transmitted from the probe 7 directly hits the defect 6 and it is received directly by the probe 7, a path (second path) wherein the ultrasonic pulse transmitted from the probe 7 is directly applied to the defect 6 and reflected by the defect 6, then reflected once on the bottom 4 before it is received by the probe 7, and a path (third path) wherein the ultrasonic pulse transmitted from the probe 7 is directly applied to the defect 6 and reflected by the defect 6, then it is reflected once on the surface 3 and further reflected once on the bottom 4 before it is received by the probe 7.

In the second path, since the ultrasonic pulse is reflected once on the bottom 4, the phase is shifted 180 degrees in comparison with the first path. In the third path, since the ultrasonic pulse is reflected once on the surface 3 and also once on the bottom 4, the total shift of the phase amounts to 360 degrees in comparison with the first path, meaning that the phase is identical to that in the first path as a result. Hence, the amplitude of the echo corresponding to the first path and the amplitude of the echo corresponding to the third path are added as they are, whereas the value of the amplitude of the echo corresponding to the second path is multiplied by −1 to provide a value obtained by reversing the phase is to be added to the amplitudes which correspond to the first and second paths. Thus, it is required to make the same correction of the changes in phase before adding up the amplitudes of the echos for each of the round trip beam paths.

In step 18 of the signal processing described above, if the amplitude of the echo of the time corresponding to a round trip beam path has a value which is not more than a predetermined signal-to-noise ratio (S/N ratio), then processing with this amplitude taken as zero may, in some cases, reduce the influences by noises on a reconstructed image acquired as a final result. In such a case, only beam paths that have significant corresponding echo amplitudes are selected among all the possible round trip beam paths which have been extracted in step 17, and the amplitudes of echos corresponding thereto are added and the addition result is added to P (xi, yi) to enable a preferable result to be obtained.

The method wherein a refraction angle is selected and a round trip beam propagation path is extracted according to the refraction angle is just one extracting method; other methods are possible. Further, it is not always necessary to determine all round trip beam propagation paths; obtaining several candidates is adequate.

As a result of the signal processing described above, the result of the inspection in the test object 1 has been acquired in terms of an image. The operation and advantage of the first embodiment will now be described.

Unlike the prior art, in the first embodiment, consideration has been given also to the reflection of the ultrasonic waves on the bottom 4 and the surface 3 of the test object 1 to obtain candidates of possible ultrasonic beam propagation paths, the ultrasonic beam paths corresponding to the candidates have been determined by arithmetic operation, and the amplitudes of the echos in the time positions which correspond to the ultrasonic beam paths have been added. Further, the result of the addition has been added in relation to the echo corresponding to each position of the probe 7 in the scanning zone of the probe 7. The result of the addition has been output as an image at the image reconstruction point. This makes it possible to reproduce an image with consideration given to the propagation paths which were not considered in the past, thus providing an operation and advantage in that more accurate examination result can be obtained than that in prior arts.

If the amplitude of the echo in the time position corresponding to an ultrasonic beam path length of the possible ultrasonic beam propagation path has a value which is not more than a predetermined signal-to-noise ratio, then only ultrasonic beam paths that have significant corresponding echo amplitude values are selected among the ultrasonic beam propagation paths, and only the amplitudes of echos corresponding thereto are added and the addition result is added to P (xi, yi), thus providing an operation and advantage in that sharper images can be obtained and therefore more accurate examination can be achieved.

Furthermore, if a beam width of −3 dB is used for the transmitted ultrasonic beam and the received ultrasonic beam, respectively, as the ultrasonic beam width specified by the foregoing angles $\Theta$ L and $\Theta$ H, then signal processing based on principal beam can be implemented, thus providing an operation and advantage in that sharper images can be obtained.

The first embodiment described above has referred to a case where an image is reconstructed by signal processing by scanning with the probe 7 at a particular value of z on a z-axis perpendicular to the x-axis and the y-axis, i.e. within a section of (x, y), although it is not shown. The first embodiment, however, is not limited thereto. The information on the defect 6 along the z-axis can be also obtained by implementing the same scanning by using the probe 7 and signal processing along the z-axis, i.e. at diverse values of z, and by reconstructing and displaying the final result in terms of a three-dimensional image in the test object 1, thus providing an operation and advantage which allow effective use for classifying, sorting, or the like of the defect 6.

The ultrasonic flaw detection apparatus and the ultrasonic flaw detection method in accordance with the first embodiment of the present invention further present an operation and advantage set forth below. For example, there is such a case as a weld bead wherein it is difficult to transmit and receive ultrasonic waves via the surface of a test object by scanning a probe close to a defect because the surface of the test object is very uneven. In such a case, if there is a defect near the surface of the test object, then no echo from the defect may be obtained by direct scanning because of the aforesaid limitation in the scanning zone of the probe wherein ultrasonic waves can be transmitted and received properly. Another problem may be encountered: even if there no such limitation in the scanning zone of the probe on the surface of the test object, the presence of a defect in the vicinity of the surface shortens the time required from the moment a transmission signal is sent to the moment the echo is received, whereas the transmission signal leaks into a receiving circuit, i.e. the receiver, so that the echo is buried in the leakage of the transmission signal, thus preventing the echo from being received properly. In this case, it is necessary to place the probe on the bottom of the test object to use the bottom as the test surface to carry out the flaw detecting examination. If, however, the test object is a part of a structure and the bottom cannot be accessed physically, then it is impossible to use the bottom as the test surface. Even in these cases where the scanning zone of the probe is limited because of the presence of a defect near the surface or where there is the problem of the leakage of a transmission signal, the ultrasonic flaw detection apparatus and the ultrasonic flaw detection method according to the first embodiment of the present invention allow the foregoing limitation to be overcome, the foregoing problem to be solved, and the flaw detecting examination to be achieved since they employ the reflection of ultrasonic waves on a bottom and the reflection of ultrasonic waves on a surface as well in addition to direct scanning.

So far, the description has been given to the cases where the probe is brought in direct contact with the test surface of the test object to carry out the flaw detecting examination. The present invention, however, is not limited thereto and instead may be applied to a so-called immersion method or immersion testing in which a test object is immersed in a liquid such as water and the probe transmits and receives ultrasonic waves to and from the test object via the liquid. The present invention may also be applied to a so-called local immersion testing wherein a water film is provided only on an acoustic transmitting and receiving surface which is the front surface of the probe, that is, only in the local space between the probe and the test surface of the test object, and ultrasonic waves are transmitted to and received from the test object. The same operations and advantages of the present invention described above can be obtained also in such immersion method, immersion testing, and local immersion testing.

In conjunction with FIG. 1, it has been described that the scanner 9 has the function for the spatial scanning of the probe 7, outputs the information on the spatial position of the probe 7, and supplies it to the position detector 85 to however, the function for gathering and outputting the information on the spatial position of the probe 7 may be implemented by a position information generator provided independently of the scanner 9, that is, the information may be gathered and output by the position information generator, then supplied to the position detector 85. In this case, the scanner 9 is responsible only for the function for the spatial scanning of the probe 7. Further, in this case, it is necessary to connect the position information generator to the controller 81 to exchange various types of signals with the controller 81.

Furthermore, in conjunction with FIG. 1, it has been described that the information on the spatial position of the probe 7 is output from the scanner 9 and applied to the position detector 85 to however, since the information on the spatial scanning zone and the travel distance of the probe 7 is controlled and generated by the controller 81, the scanner 9 may be responsible only for the spatial scanning function, and the information on the scanning of the probe 7 from the controller 81 may be directly supplied to and stored in the signal processor 84, thus obviating the need for providing the position detector 85.

Second Embodiment

Figure 16:
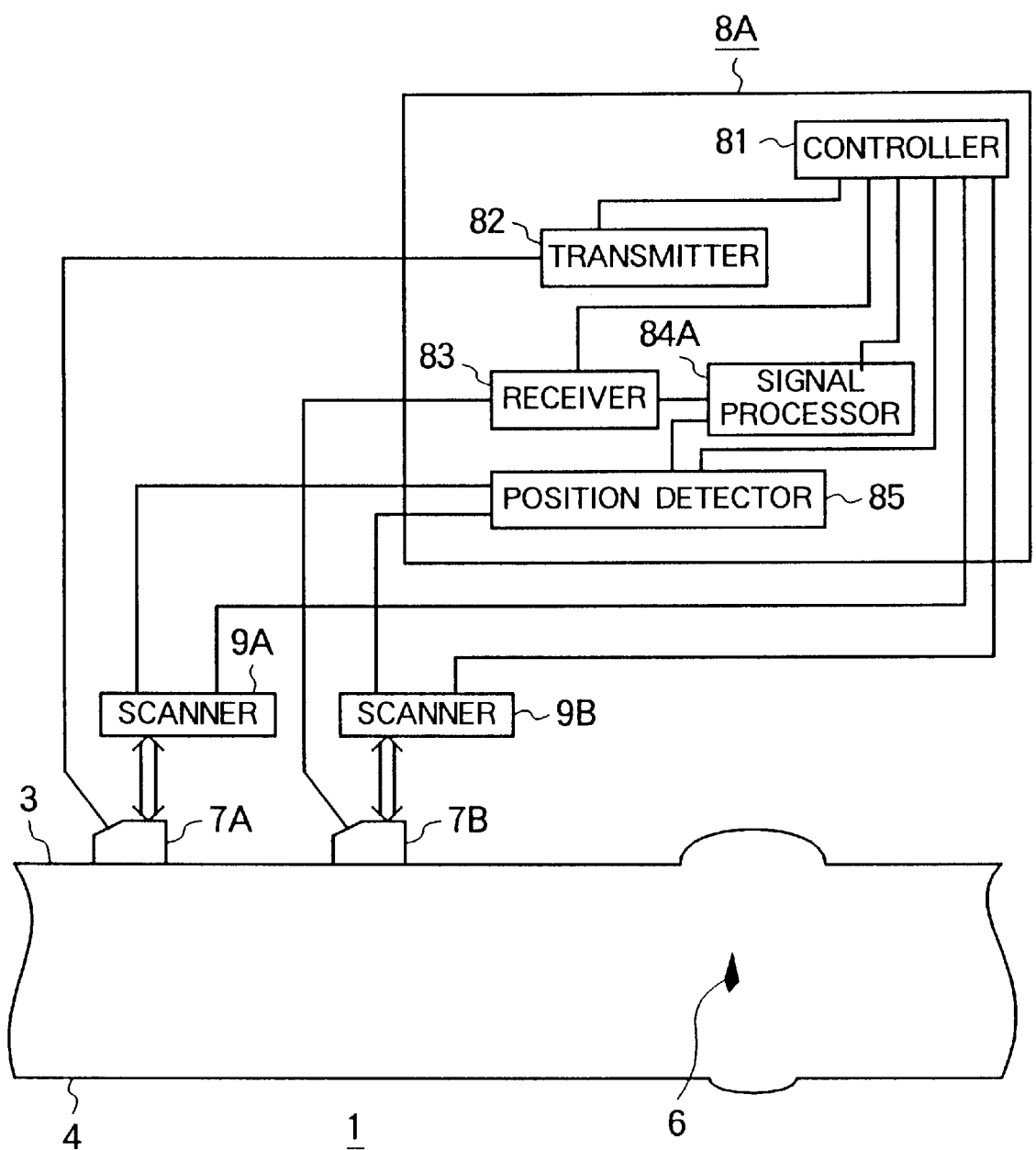
FIG. 16 is a diagram showing the configuration of an ultrasonic flaw detection apparatus according to a second embodiment of the present invention.

Referring to FIG. 16, the configuration of an ultrasonic flaw detection apparatus according to a second embodiment of the present invention will be described. FIG. 16 is a block diagram illustrating the configuration of the ultrasonic flaw detection apparatus according to the second embodiment of the invention.

In FIG. 16, the ultrasonic flaw detection apparatus is equipped with a transmitting probe 7A and a receiving probe 7B rested on a test object 1, a transmitter-receiver 8A connected to the probes 7A and 7B, and scanners 9A and 9B for the transmitting probe 7A and the receiving probe 7B.

Further in the drawing, the transmitter-receiver 8A includes a controller 81, a transmitter 82, a receiver 83, a signal processor 84A, and a position detector 85 for the probes 7A and 7B. The scanners 9A and 9B include position detecting sensors for the transmitting probe 7A and the receiving probe 7B although they are not shown.

In the drawing, the transmitting probe 7A and the receiving probe 7B are connected to the transmitter 82 and the receiver 83, respectively, by signal conductors. The receiver 83 is connected to the signal processor 84A. The position detector 85 is connected to the signal processor 84A. The controller 81 is connected to the transmitter 82, the receiver 83, the signal processor 84A, the position detector 85, and the scanners 9A and 9B.

Further in the drawing, the scanners 9A and 9B are connected to the position detector 85. The output signals from the position detecting sensors of the scanners 9A and 9B are supplied to the position detector 85. The information on the positions of the probes 7A and 7B detected by the position detector 85 is supplied to the signal processor 84A.

The signal processor 84A has a memory inside as in the case of the first embodiment although it is not shown. Various results obtained by operations and calculations are stored in this memory, and the input signals supplied to the signal processor 84A are also stored therein as necessary.

Furthermore, although not shown, the signal processor 84A furnishes signals which indicate processing states to the controller 81 as necessary. Based on the input signals, the controller 81 issues control signals to the transmitter 82, the receiver 83, the signal processor 84A, the position detector 85, and the scanners 9A and 9B to control them.

The configurations of the transmitting probe 7A and the receiving probe 7B are the same as that shown in FIG. 2. Refraction angle θ a corresponding to refraction angle θ shown in FIG. 2, which is related to the transmitting probe 7A may be identical to or different from refraction angle θ b which is related to the receiving probe 7B; if they are different, the capability for detecting the defect 6 can be further improved in some cases.

The operation of the ultrasonic flaw detection apparatus according to the second embodiment of the present invention will now be described with reference to FIG. 17 through FIG. 29.

Figure 28:
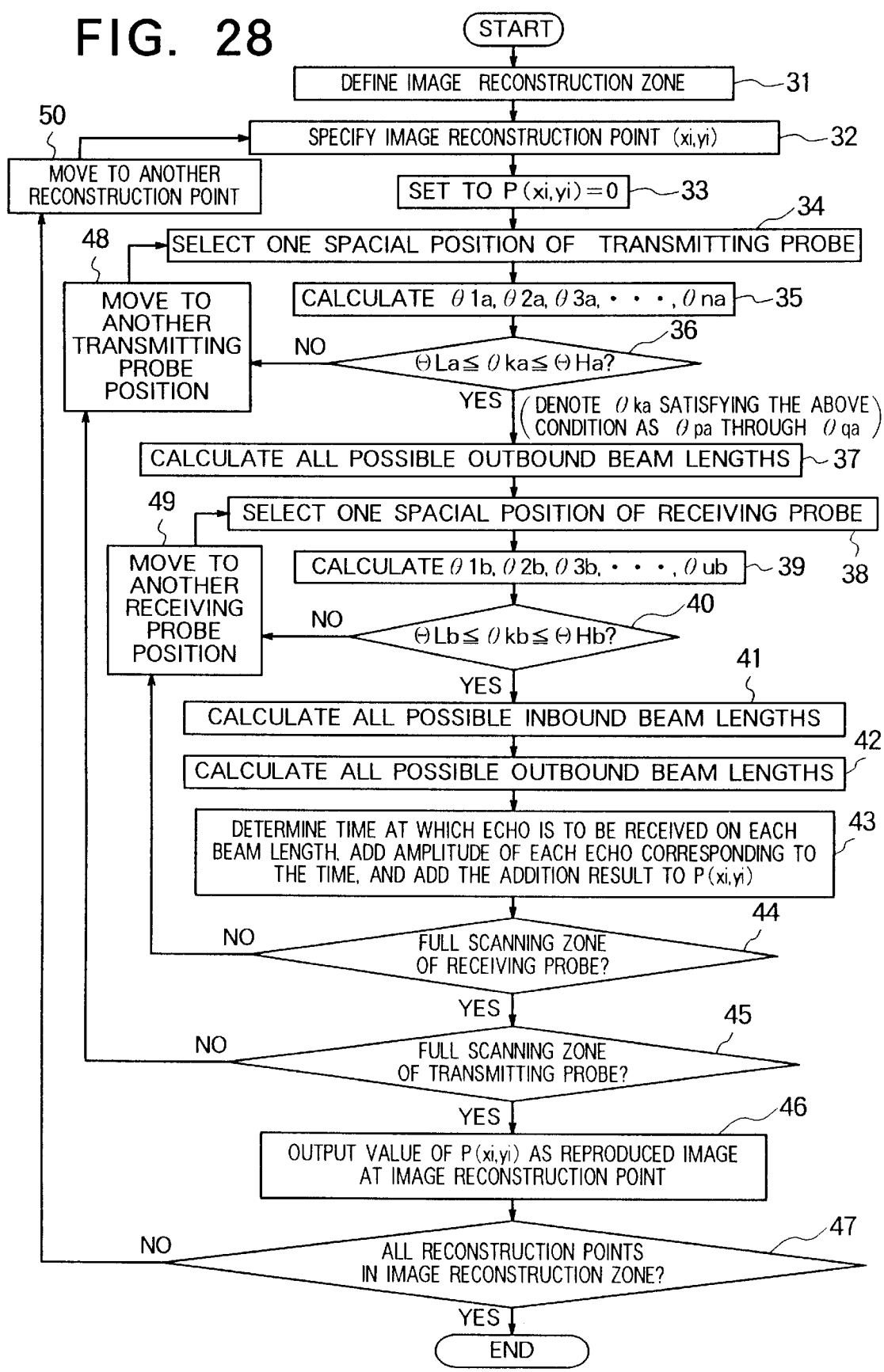
FIG. 28 is a flowchart for describing the signal processing of the ultrasonic flaw detection apparatus according to the second embodiment of the present invention.
Figure 29:
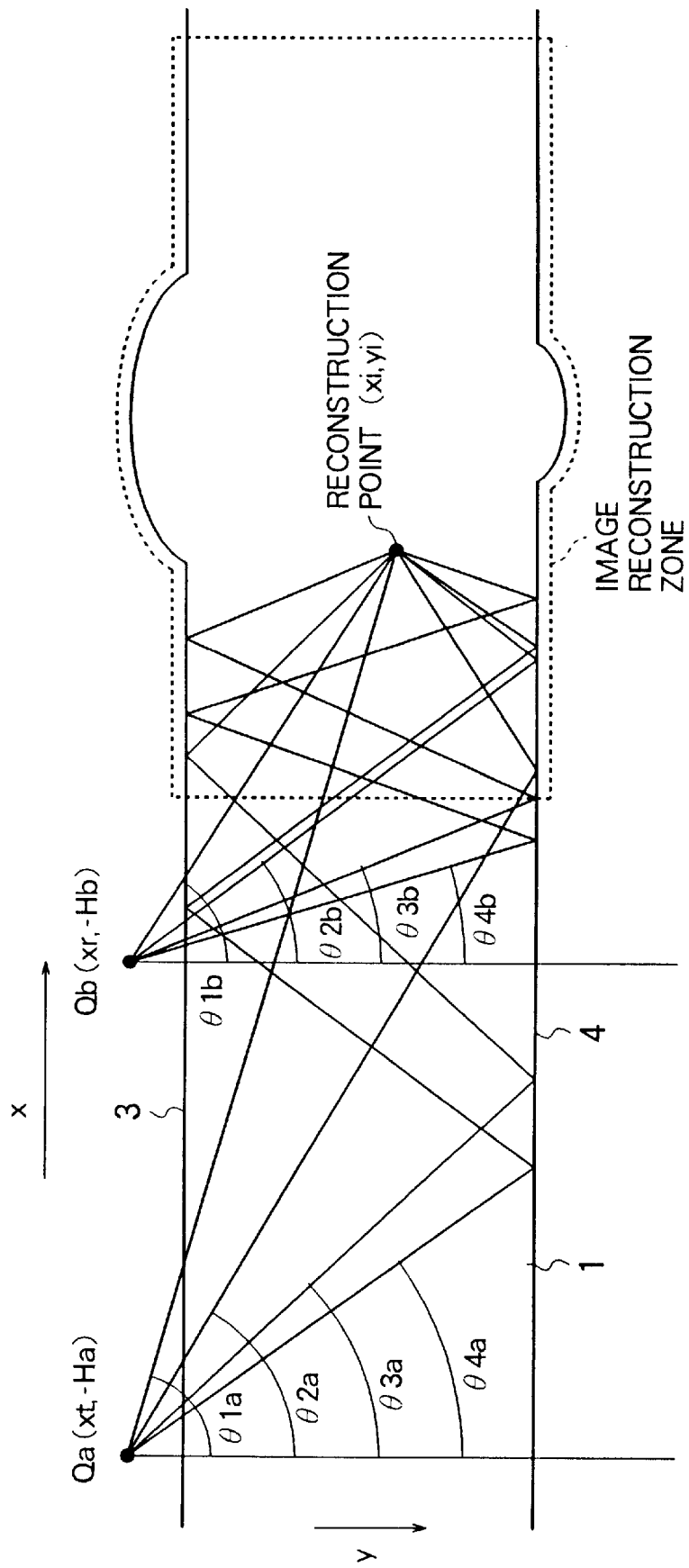
FIG. 29 is a diagram showing a propagation path of an ultrasonic beam for describing the operation of the ultrasonic flaw detection apparatus according to the second embodiment of the present invention.

FIG. 17 through FIG. 27 are diagrams illustrating the ultrasonic beam propagation paths for describing the operation of the ultrasonic flaw detection apparatus according to the second embodiment. FIG. 28 is a flowchart for describing the signal processing of the ultrasonic flaw detection apparatus according to the second embodiment. Further, FIG. 29 is a diagram illustrating the beam propagation path for describing the flowchart of the signal processing shown in FIG. 28.

As in the case of the first embodiment, a transmission signal such as a narrow pulse which may be regarded as an impulse or a burst signal which has a certain carrier frequency is generated and transmitted from the transmitter 82 to the transmitting probe 7A. The transmitting probe 7A is driven by the transmission signal to the transmitting probe 7A transmits the ultrasonic pulse at an angle with respect to the test surface of the test object 1, i.e. the surface 3 of the test object 1. The ultrasonic pulse propagates in the test object 1 and is reflected and scattered by the defect 6. The reflected and scattered ultrasonic pulse propagates through the test object 1 and is received by the receiving probe 7B. The received echo is amplified by the receiver 83 before is sent to the signal processor 84A.

The information on the spatial positions of the transmitting probe 7A and the receiving probe 7B is detected by the scanners 9A and 9B and is sent to the position detector 85. The information on the spatial positions of the transmitting probe 7A and the receiving probe 7B from the position detector 85 is sent to the signal processor 84A.

The signal processor 84A stores the information on the spatial positions of the transmitting probe 7A and the receiving probe 7B and the received echo.

With both transmitting probe 7A and the receiving probe 7B fixed in a certain spatial position, the operation described above is performed and the information on the spatial positions of the transmitting probe 7A and the receiving probe 7B and the information on the echo are stored.

Then, with the transmitting probe 7A fixed in the spatial position, the receiving probe 7B is moved by the scanner 9B to another spatial position. An ultrasonic pulse is transmitted from the transmitting probe 7A by the transmission signal, and the received echo from the defect 6 and the information on the spatial positions of the transmitting probe 7A and the receiving probe 7B are transmitted to and stored in the signal processor 84A in the same manner as described above. This series of operations including the spatial scanning of the receiving probe 7B is conducted over a predetermined scanning zone of the receiving probe 7B.

Next, the transmitting probe 7A is moved by the scanner 9A to another spatial position and fixed at that point. An ultrasonic pulse is transmitted from the transmitting probe 7A by the transmission signal, and the received echo from the defect 6 and the information on the spatial positions of the transmitting probe 7A and the receiving probe 7B are transmitted to and stored in the signal processor 84A in the same manner as described above. This series of operations including the spatial scanning of the receiving probe 7B is conducted over a predetermined scanning zone of the receiving probe 7B.

The series of operations including the spatial scanning of the transmitting probe 7A and the receiving probe 7B are implemented over the predetermined scanning zones of the transmitting probe 7A and the receiving probe 7B.

By performing the operations described above, the transmitting probe 7A is spatially moved in the predetermined scanning zone, and the receiving probe 7B is moved in the predetermined scanning zone at each position of the transmitting probe 7A in the scanning zone thereof. The information on each spatial position of the transmitting probe 7A and the receiving probe 7B and the information on the echos in these positions are stored in the signal processor 84A. After that, the signal processing to be discussed later is carried out in the signal processor 84.

Before describing the signal processing procedure in the signal processor 84A, the propagating characteristic of the ultrasonic beam in the test object 1 will be described with reference to FIG. 17 through FIG. 22.

Figure 17:
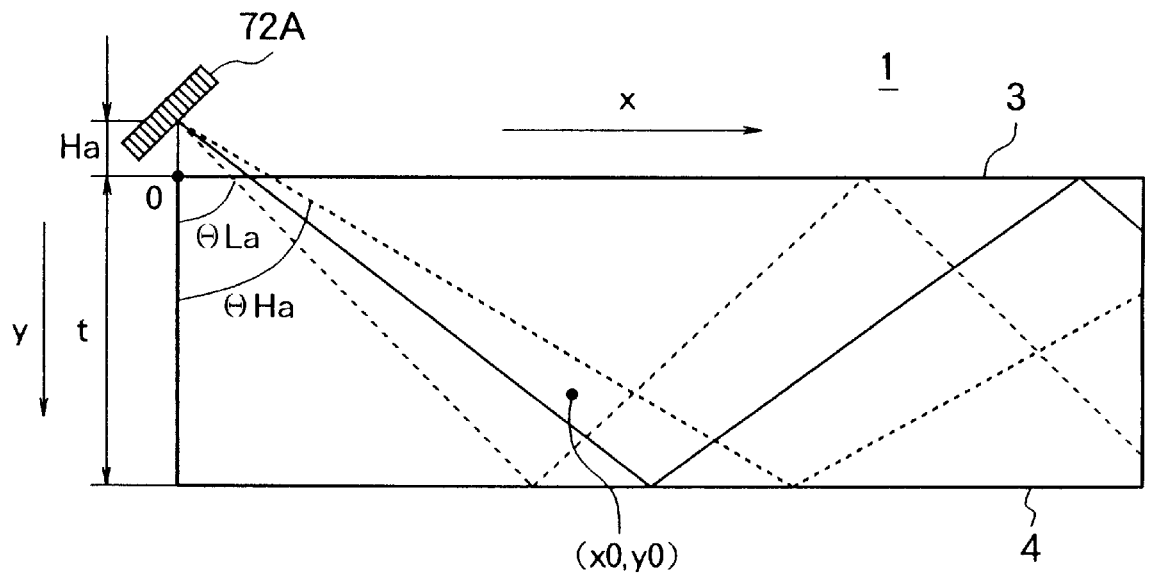
FIG. 17 is a diagram showing a propagation path of an ultrasonic beam for describing the operation of the ultrasonic flaw detection apparatus according to the second embodiment of the present invention.

FIG. 17 is an ultrasonic beam propagation path diagram concerned with an ultrasonic beam transmitted from the transmitting probe 7A. In FIG. 17, the horizontal direction is taken on an x-axis, while the vertical direction is taken on a y-axis. As in the case shown in FIG. 3, it is assumed that a point reflection source is located at (x0, y0). Reference numeral 72A denotes an apparent transducer associated with the transmitting probe 7A. "Ha" denotes the height from the surface 3 of the test object 1 to the center of the apparent transducer 72A. An ultrasonic beam transmitted from the apparent transducer 72A associated with the transmitting probe 7A diverges due to diffraction. In the drawing, the solid line indicates the centerline of the beam, while the dashed lines indicate the lines which connect the points at which the sound pressure becomes −3 dB from the sound pressure on the centerline. In other words, the zone defined by the two dashed lines corresponds to an effective beam width of the transmitted ultrasonic beam. The refraction angles corresponding to the two dashed lines are denoted as "Θ La" and "Θ Ha" as shown in the drawing.

Figure 18:
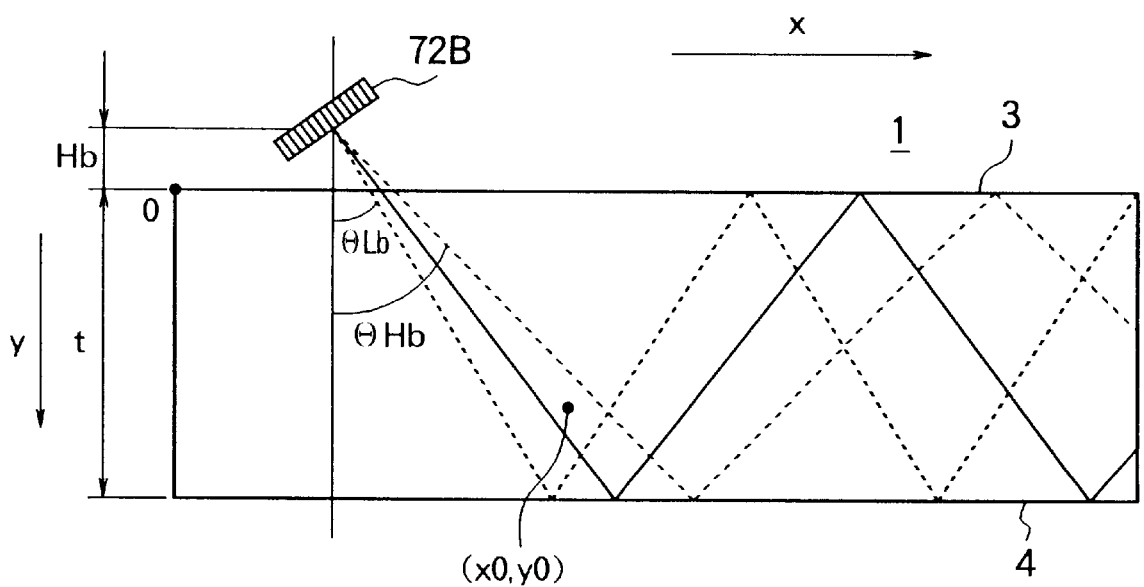
FIG. 18 is a diagram showing a propagation path of an ultrasonic beam for describing the operation of the ultrasonic flaw detection apparatus according to the second embodiment of the present invention.

FIG. 18 is an ultrasonic beam propagation path diagram concerned with an ultrasonic beam received by the receiving probe 7B. In FIG. 18 also, the horizontal direction is taken on an x-axis, while the vertical direction is taken on a y-axis. As in the cases shown in FIG. 3 and FIG. 17, it is assumed that a point reflection source is located at (x0, y0). Reference numeral 72B denotes an apparent transducer associated with the receiving probe 7B. "Hb" denotes the height from the surface 3 of the test object 1 to the center of the receiving probe 7B. The ultrasonic beam received by the apparent transducer 72B is received at a certain spread angle when the diffraction of the ultrasonic wave is taken into account. In the drawing, the solid line indicates the centerline of the beam, while the dashed lines indicate the lines which connect the points at which the sound pressure becomes −3 dB from the sound pressure on the centerline. In other words, the zone defined by the two dashed lines corresponds to an effective beam width of the received ultrasonic beam. The refraction angles corresponding to the two dashed lines are denoted as "Θ Lb" and "Θ Hb" as shown in the drawing.

In FIG. 17 and FIG. 18, the beam width of −3 dB is used, but it is not limited thereto; it may be 6−dB or −9 dB according to the application or purpose, or other value may be used to define the effective beam width. Furthermore, different values may be used for transmission and reception to define the effective beam widths.

Referring now to FIG. 19 through FIG. 22, the sound rays in the foregoing transmitted ultrasonic beam width and the foregoing received ultrasonic beam width will be discussed. In FIG. 19 through FIG. 22, the origin of the coordinates is established at a point where the center of the apparent transducer 72A of the transmitting probe 7A is projected onto the surface 3 of the test object 1 along the y-axis as in the case shown in FIG. 17. Point "Qa" denotes the center of the apparent transducer 72A and the coordinates thereof is (0, −Ha). Point "Qb" denotes the center of the apparent transducer 72B of the receiving probe 7B; the coordinates thereof is (xr, −Hb). A blank circle mark located at (x0, y0) denotes a reflection source which corresponds to the defect 6.

To make the description easier to understand, consideration will be focused only up to one reflection on the bottom 4 of the test object 1, referring to FIG. 19 through FIG. 22.

Figure 19:
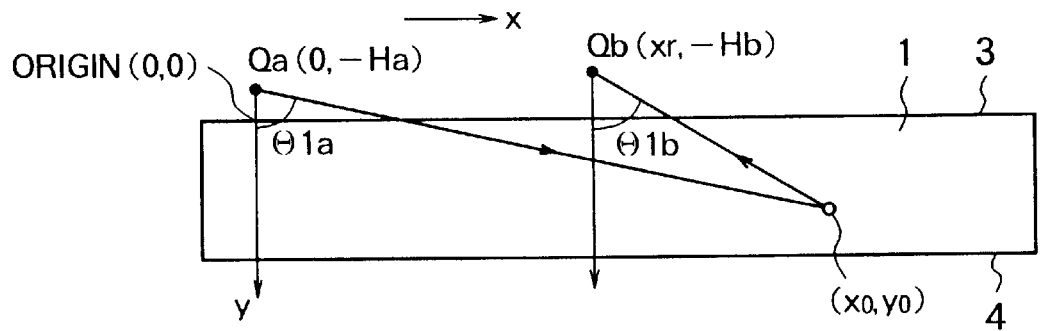
FIG. 19 is a diagram showing a propagation path of an ultrasonic beam for describing the operation of the ultrasonic flaw detection apparatus according to the second embodiment of the present invention.

As shown in FIG. 19, if a sound ray corresponding to a refraction angle Θ 1a exists in the aforesaid transmitted ultrasonic beam width and a sound ray corresponding to a refraction angle Θ 1b exists in the foregoing received ultrasonic beam width, i.e. if Θ La≦Θ 1a≦Θ Ha and also Θ Lb≦Θ 1b≦Θ Hb at the same time, then there is a likelihood that an ultrasonic beam propagation path indicated by the arrows exists. In this case, the ultrasonic wave transmitted from the transmitting probe 7A directly hits the defect 6 and it is directly reflected and received as an echo by the receiving probe 7B. In this case, Θ 1a and Θ 1b are respectively given by equation 22 and equation 23 shown below.

$$\Theta 1a = \tan^{-1}[x0/(y0+Ha)] \quad \text{Equation 22}$$

$$\Theta 1b = \tan^{-1}[(x0-xr)/(y0+Hb)] \quad \text{Equation 23}$$

The overall length of the round trip beam path in this case is L1a+L1b; L1a and L1b are determined by equation 24 and equation 25, respectively.

$$L1a = SQRT[x0^2+(y0+Ha)^2] \quad \text{Equation 24}$$

$$L1b = SQRT[(x0-xr)^2+(y0+Hb)^2] \quad \text{Equation 25}$$

Figure 20:
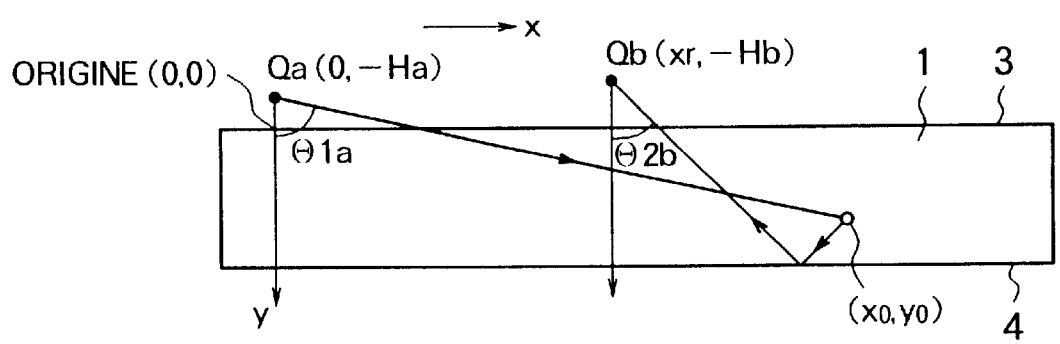
FIG. 20 is a diagram showing a propagation path of an ultrasonic beam for describing the operation of the ultrasonic flaw detection apparatus according to the second embodiment of the present invention.

As shown in FIG. 20, if a sound ray equivalent to refraction angle Θ 1a exists in the aforesaid transmitted ultrasonic beam width and a sound ray equivalent to refraction angle Θ 2b also exists in the aforesaid received ultrasonic beam width, that is, if Θ La≦Θ 1a≦Θ Ha, and also Θ Lb≦Θ 2b≦Θ Hb at the same time, then a beam path may exist, in which the ultrasonic wave transmitted from the transmitting probe 7A is directly applied to the defect 6, reflected by the defect 6, and reflected once on the bottom 4 before reaching the receiving probe 7B to be received as an echo as shown by the arrows. In this case, Θ 2b is given by the following equation 26.

$$\Theta 2b = \tan^{-1}[(x0-xr)/(2t-y0+Hb)] \quad \text{Equation 26}$$

The total beam path length in this case is L1a+L2b; L2b is given by equation 27 shown below.

$$L2b = SQRT[(x0-xr)^2+(2t-y0+Hb)^2] \quad \text{Equation 27}$$

Figure 21:
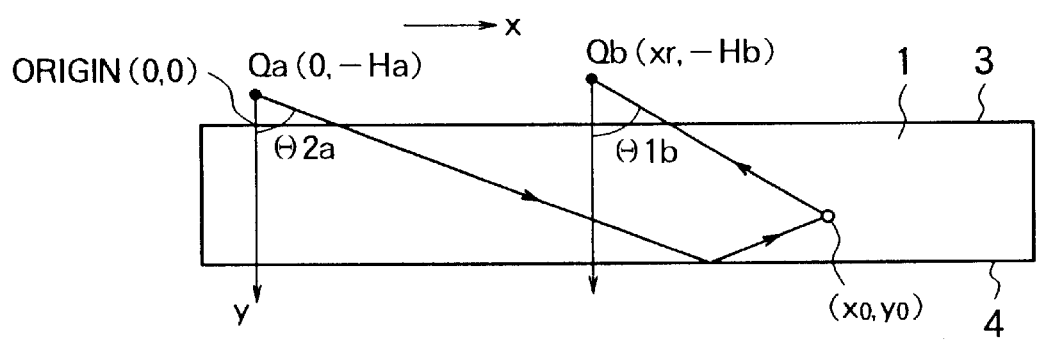
FIG. 21 is a diagram showing a propagation path of an ultrasonic beam for describing the operation of the ultrasonic flaw detection apparatus according to the second embodiment of the present invention.

Further, as shown in FIG. 21, if a sound ray corresponding to a refraction angle Θ 2a exists in the aforesaid transmitted ultrasonic beam width and a sound ray corresponding to a refraction angle Θ 1b exists in the foregoing received ultrasonic beam width, i.e. if Θ La≦Θ 2a≦Θ Ha and also Θ Lb≦Θ 1b≦Θ Hb at the same time, then there is a likelihood that a propagation path exists, in which the ultrasonic wave transmitted from the transmitting probe 7A is reflected once on the bottom 4 before it hits the defect 6, then it is reflected by the defect 6 before directly reaching the receiving probe 7B to be received as an echo as shown by the arrows. In this case, Θ 2a is given by the following equation 28.

$$\Theta 2a = \tan^{-1}[x0/(2t-y0+Ha)] \quad \text{Equation 28}$$

The total beam path length in this case is L2a+L1b; L2a is given by equation 29 shown below.

$$L2a = SQRT[x0^2+(2t-y0+Ha)^2] \quad \text{Equation 29}$$

Figure 22:
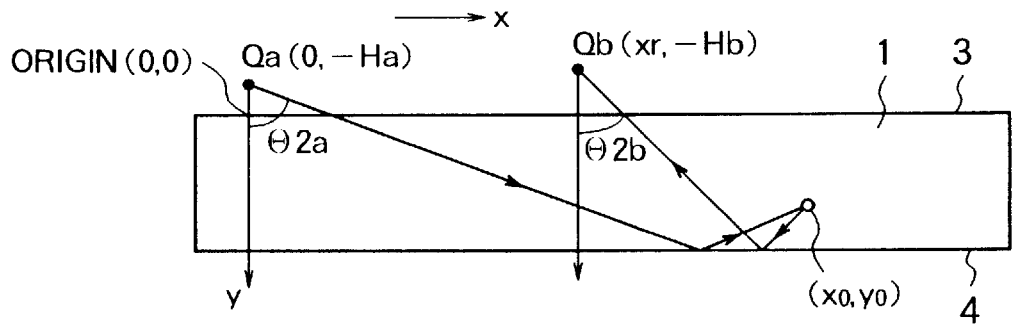
FIG. 22 is a diagram showing a propagation path of an ultrasonic beam for describing the operation of the ultrasonic flaw detection apparatus according to the second embodiment of the present invention.

If, Θ La≦Θ 2a≦Θ Ha and also Θ Lb≦Θ 2b≦Θ Hb at the same time, then there may be a propagation path shown in FIG. 22. Specifically, the ultrasonic wave transmitted from the transmitting probe 7A is reflected once on the bottom 4 before hits the defect 6, then it is reflected by the defect 6 and reflected once on the bottom 4 before reaching the receiving probe 7B to be received as an echo as shown by the arrows. In this case, the total beam path length is L2a+L2b.

So far, for the clarity of description, the consideration has been given to the cases where the sound rays up to those corresponding to refraction angle Θ 2a exist in the effective transmitted ultrasonic beam width and the sound rays up to those corresponding to refraction angle Θ 2b exist in the effective received ultrasonic beam width. In other words, consideration has been given to cases where the ultrasonic beam is reflected once on the bottom 4 in the beam paths.

Cases where the beam widths are greater than those discussed above will now be considered with reference to FIG. 23 through FIG. 27. FIG. 23 through FIG. 27 illustrate possible beam paths in those cases where the ultrasonic wave is reflected once on the bottom 4 and reflected once on the surface 3, that is, those cases where sound rays corresponding to refraction angles Θ 1a through Θ 3a exist in the aforesaid transmitted ultrasonic beam width and sound rays corresponding to refraction angles Θ 1b through Θ 3b exist in the aforesaid received ultrasonic beam width. The beam propagation paths shown in FIG. 23 through FIG. 27 may exist in addition to those shown in FIG. 19 through FIG. 22, where Θ 3a and Θ 3b are given by equation 30 and equation 31, respectively shown below.

$$\Theta 3a = \tan^{-1}[x0/(2t+y0+Ha)] \quad \text{Equation 30}$$

$$\Theta 3b = \tan^{-1}[(x0-xr)/(2t+y0+Hb)] \quad \text{Equation 31}$$

Figure 23:
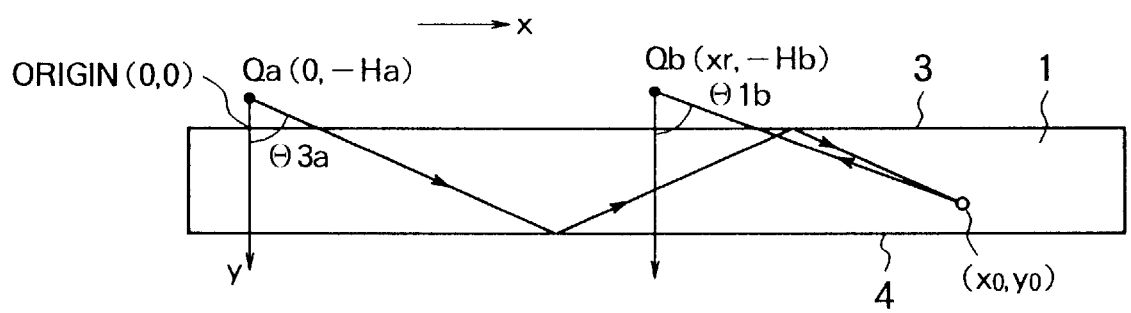
FIG. 23 is a diagram showing a propagation path of an ultrasonic beam for describing the operation of the ultrasonic flaw detection apparatus according to the second embodiment of the present invention.

Description will now be given in conjunction with FIG. 23 through FIG. 27. FIG. 23 illustrates a path wherein an ultrasonic wave transmitted from the transmitting probe 7A is reflected once on the bottom 4 and further reflected once on the surface 3, then it hits the defect 6 and it is reflected by the defect 6 before directly reaching the receiving probe 7B to be received as an echo as indicated by the arrows. In this case, the total beam path length is L3a+L1b; L3a is given by the following equation 32.

$$L3a = SQRT[x0^2 + (2t+y0+Ha)^2] \quad \text{Equation 32}$$

Figure 24:
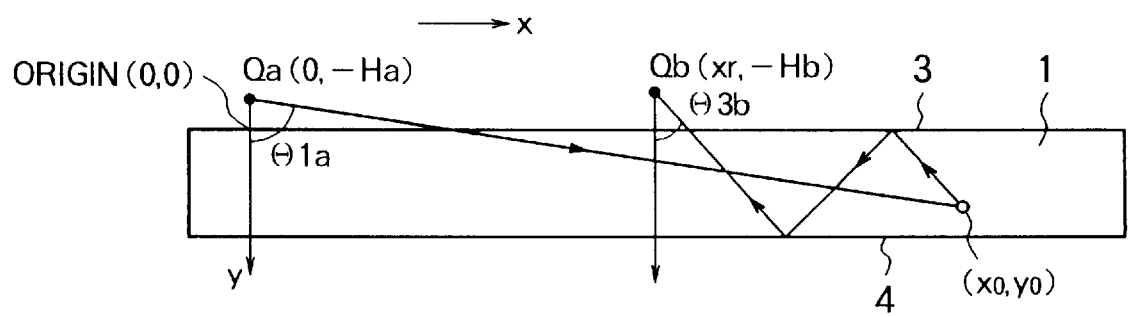
FIG. 24 is a diagram showing a propagation path of an ultrasonic beam for describing the operation of the ultrasonic flaw detection apparatus according to the second embodiment of the present invention.

FIG. 24 shows a path wherein the ultrasonic wave transmitted from the transmitting probe 7A directly hits the defect 6 and it is reflected by the defect 6, then reflected once on the surface 3 and reflected once on the bottom 4 before reaching the receiving probe 7B to be received as an echo. In this case the overall beam path length is L1a+L3b; L3b is given by the following equation 33.

$$L3b = SQRT[(x0-xr)^2 + (2t+y0+Hb)^2] \quad \text{Equation 33}$$

Figure 25:
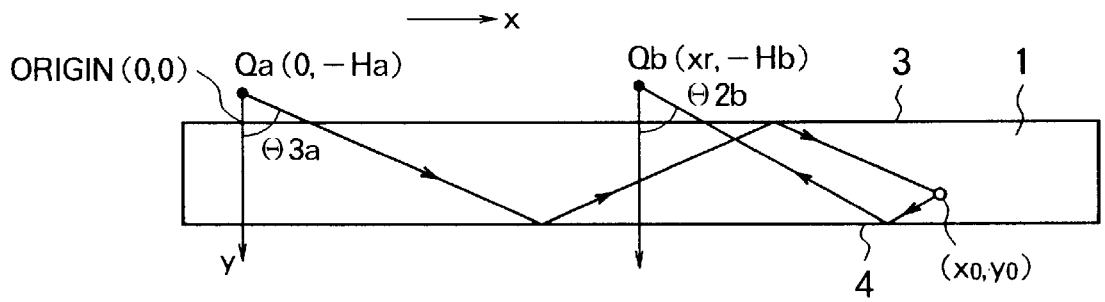
FIG. 25 is a diagram showing a propagation path of an ultrasonic beam for describing the operation of the ultrasonic flaw detection apparatus according to the second embodiment of the present invention.

FIG. 25 illustrates a path wherein an ultrasonic wave transmitted from the transmitting probe 7A is reflected once on the bottom 4 and further reflected once on the surface 3 before hitting the defect 6, then it is reflected by the defect 6 and further reflected once on the bottom 4 before reaching the receiving probe 7B to be received as an echo as indicated by the arrows. In this case, the total beam path length is L3a+L2b.

Figure 26:
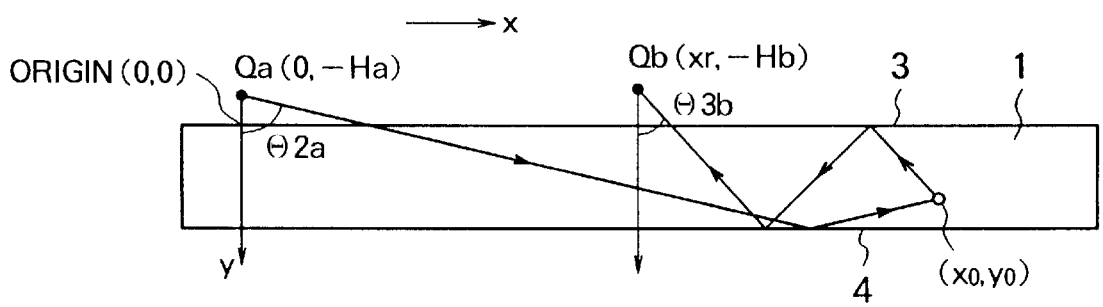
FIG. 26 is a diagram showing a propagation path of an ultrasonic beam for describing the operation of the ultrasonic flaw detection apparatus according to the second embodiment of the present invention.

FIG. 26 illustrates a path wherein an ultrasonic wave transmitted from the transmitting probe 7A is reflected once on the bottom 4 before hitting the defect 6, then it is reflected by the defect 6, reflected once on the surface 3, and further reflected once on the bottom 4 before reaching the receiving probe 7B to be received as an echo. In this case, the total beam path length is L2a+L3b.

Figure 27:
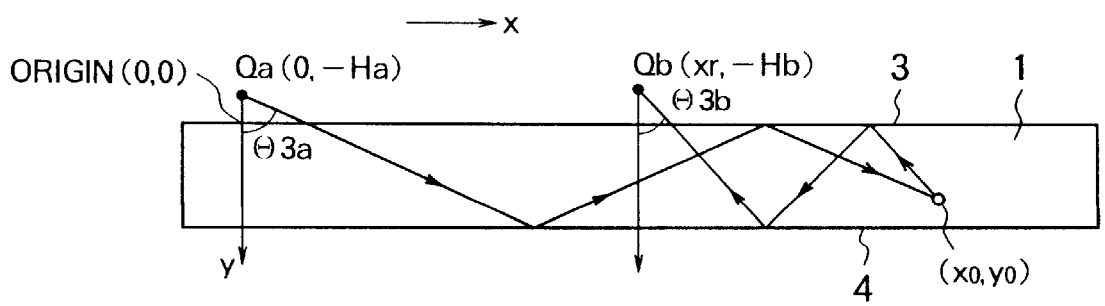
FIG. 27 is a diagram showing a propagation path of an ultrasonic beam for describing the operation of the ultrasonic flaw detection apparatus according to the second embodiment of the present invention.

FIG. 27 illustrates a path wherein an ultrasonic wave transmitted from the transmitting probe 7A is reflected once on the bottom 4 and further reflected once on the surface 3 before hitting the defect 6, then is reflected by the defect 6, reflected once on the surface 3 and further reflected once on the bottom 4 before reaching the receiving probe 7B to be received as an echo as indicated by the arrows. In this case, the total beam path length is L3a+L3b.

If the effective transmitted ultrasonic beam width and the received ultrasonic beam width are greater than those in the cases discussed above, then it is necessary to also consider a beam path wherein the ultrasonic wave transmitted from the transmitting probe 7A is reflected once on the bottom 4, then reflected once on the surface 3, and further reflected once on the bottom 4 before hitting the defect 6, and a path wherein the ultrasonic wave reflected by the defect 6 is reflected once on the bottom 4, reflected once on the surface 3, and further reflected once on the bottom 4 before being received by the receiving probe 7B.

If the effective transmitting and receiving beam widths are still greater, then it is necessary to also consider a path wherein the ultrasonic wave is reflected twice on the bottom 4 and twice on the surface 3. Thus, as the beam width increases, the number of reflections on the bottom 4 and the surface 3 in the paths to be considered increases accordingly.

As described above, one of the significant differences of the second embodiment from the conventional ones is that it provides an apparatus and a method for detecting flaws at an angle by taking the spread of ultrasonic beams into account. Moreover, the second embodiment is entirely different from the prior art disclosed in Japanese Unexamined Patent Publication No. 2-278149, Japanese Unexamined Patent Publication No. 2-248855, or Japanese Unexamined Patent Publication No. 5-172789 in that consideration is given also to the reflection on the surface 3 and the bottom 4.

Based on the consideration results concerning the ultrasonic beam paths shown in FIG. 17 through FIG. 27, the signal processing procedure in the signal processor 84A will now be described with reference to FIG. 28 and FIG. 29. The coordinate origin in FIG. 29 is different from those in FIG. 19 through FIG. 27. Obviously, the origin may be located anywhere. It is needless to say that coordinate conversion must be implemented if the origin is different from that used for scanning with the transmitting probe 7A and the receiving probe 7B.

As previously described, there are stored in the signal processor 84A the echo waveforms at spatial points in the scanning zone when a predetermined scanning zone was scanned with the transmitting probe 7A and the receiving probe 7B, the information on the spatial positions of the transmitting probe 7A at the time when the echo waveforms were received, and the information on the spatial positions of the receiving probe 7B. The echo waveforms are stored as raw waveforms, i.e. AC waveforms which have not been subjected to such processing as rectification and detection.

In step 31, a predetermined image reconstructing zone is decided. More specifically, in FIG. 29, a zone where an image should be displayed as a result of the flaw detection of the test object 1 is defined as indicated, for example, by the dotted line.

In step 32, an image reconstructing point is specified. The image reconstructing point is one point in the foregoing image reconstructing zone. The coordinates of this point are set to (xi, yi) as shown in FIG. 29.

In step 33, the output corresponding to the reconstructing point (xi, yi) is defined as P (xi, yi), and the value is set to zero. This means that the setting is P (xi, yi)=0.

In step 34, a single spatial position of the transmitting probe 7A where the echo has been received in the scanning zone of the transmitting probe 7A is selected. As shown in FIG. 29, the position of the transmitting probe 7A is represented by point Qa, and the coordinates are assumed to be (xt, −Ha). The meaning of point Qa is the same as in FIG. 17 to FIG. 27.

In step 35, the angles θ 1a, θ 2a, θ 3a, θ 4a . . . , θ na shown in FIG. 29 are calculated. In this case, n is an integer; it is decided in advance according to the image reconstructing zone and the scanning zone of the transmitting probe 7A, taking the effective beam width of the transmitting probe 7A into account. The angles of θ 1a through θ na are given by the following equations 34 through 38.

$$\theta 1a = \tan^{-1}[(xi-xt)/(yi+Ha)] \qquad \text{Equation 34}$$

$$\theta 2a = \tan^{-1}[(xi-xt)/(2t-yi+Ha)] \qquad \text{Equation 35}$$

$$\theta 3a = \tan^{-1}[(xi-xt)/(2t+yi+Ha)] \qquad \text{Equation 36}$$

$$\theta 4a = \tan^{-1}[(xi-xt)/(4t-yi+Ha)] \qquad \text{Equation 37}$$

$$\theta na = \tan^{-1}[(xi-xt)/(mt-(-1)^n\,yi+Ha)] \qquad \text{Equation 38}$$

In this case, m is given as follows: if n is an even number, then m=n; if n is an odd number, then m=n−1.

If the image reconstructing point is tentatively regarded as the reflection source, and a beam path wherein an ultrasonic wave transmitted from the transmitting probe 7A reaches the image reconstructing point (xi, yi) is considered, then these angles θ 1a through θ na will be as shown below.

Angle θ 1a corresponds to a path wherein the ultrasonic wave transmitted from the transmitting probe 7A is directly applied to the point (xi, yi). If the distance of one way of the beam path in this case is taken as w1a, then w1a l is determined by equation 39 shown below:

$$w1a = SQRT\,[(xi-xt)^2 + (yi+Ha)^2] \qquad \text{Equation 39}$$

Angle θ 2a corresponds to a beam path wherein the ultrasonic wave transmitted from the transmitting probe 7A is reflected once on the bottom 4 before it hits the point (xi, yi) If the distance of one way of the beam path in this case is taken as w2a, then w2a is determined by equation 40 shown below:

$$w2a = SQRT\,[(xi-xt)^2 + (2t-yi+Ha)^2] \qquad \text{Equation 40}$$

Angle θ 3a corresponds to a beam path wherein the ultrasonic wave transmitted from the transmitting probe 7A is reflected once on the bottom 4 and then reflected once on the surface 3 before it hits the point (xi, yi). If the distance of one way of the beam path in this case is taken as w3a, then w3a is determined by equation 41 shown below:

$$w3a = SQRT\,[(xi-xt)^2 + (2t+yi+Ha)^2] \qquad \text{Equation 41}$$

Angle θ 4a corresponds to a beam path wherein the ultrasonic wave transmitted from the transmitting probe 7A is reflected once on the bottom 4, then reflected once on the surface 3 and further reflected on the bottom 4 once again before it hits the point (xi, yi). If the distance of one way of the beam path in this case is taken as w4a, then w4a is determined by equation 42 shown below:

$$w4a = SQRT\,[(xi-xt)^2 + (4t-yi+Ha)^2] \qquad \text{Equation 42}$$

The same applies to θ 5a through θ na and the description therefor will be omitted because it can be inferred without the need for description in particular. If one way of the beam path corresponding to angle θ na is taken as wna, then wna is given by equation 43 shown below:

$$wna = SQRT\,[(xi-xt)^2 + (mt-(-1)^n yi+Ha)^2] \qquad \text{Equation 43}$$

In step 36, it is determined whether θ 1a through θ na obtained by the calculation in step 35 lie in the effective beam width of the transmitted ultrasonic beam related to the transmitting probe 7A. And those that lie in the effective beam width of the transmitted ultrasonic beam are selected among θ 1a through θ na. More specifically, assuming ka as integers from 1 to n, θ ka which satisfies the conditional equation 44 shown below is selected to provide θ pa through θ qa. The values of pa and qa take the integers which fall in the range from 1 to n.

$$\Theta La \leq \Theta\,ka \leq \Theta\,Ha \qquad \text{Equation 44}$$

If no θ ka which satisfies the above conditional equation exists, then the program proceeds to step 48. This step 48 will be discussed later.

In step 37, the propagation paths of the aforesaid ultrasonic beams respectively associated with θ pa through θ qa which have been selected in step 36 are extracted. More specifically, in respective angles θ pa through θ qa, the ultrasonic beam propagation paths (the propagation path on the way) along which the ultrasonic wave transmitted from the transmitting probe 7A reaches the image reconstruction point (xi, yi) are extracted. Further, beam path lengths wpa through wqa respectively corresponding to angles θ pa through θ qa are calculated.

In step 38, the spatial position of the receiving probe 7B when an echo has been received is selected in the position of the transmitting probe 7A which has been selected in step 34 within the scanning zone where the receiving probe 7B has been moved for scanning. As shown in FIG. 29, the position of the receiving probe 7B is represented by point Qb, and the coordinates are assumed to be (xr, −Hb). The meaning of point Qb is the same as in FIG. 17 to FIG. 27.

In step 39, the angles θ 1b, θ 2b, θ 3b, . . . , θ ub shown in FIG. 29 are calculated. In this case, u is an integer; it is decided in advance according to the image reconstruction zone and the scanning zone of the receiving probe 7B, taking the effective beam width of the receiving probe 7B into account. The angles of θ 1b through θ ub are given by the following equations 45 through 49.

$$\theta 1b = \tan^{-1}[(xi-xr)/(yi+Hb)] \qquad \text{Equation 45}$$

$$\theta 2b = \tan^{-1}[(xi-xr)/(2t-yi+Hb)] \qquad \text{Equation 46}$$

$$\theta 3b = \tan^{-1}[(xi-xr)/(2t+yi+Hb)] \qquad \text{Equation 47}$$

$$\theta 4b = \tan^{-1}[(xi-xr)/(4t-yi+Hb)] \qquad \text{Equation 48}$$

$$\theta ub = \tan^{-1}[(xi-xr)/(vt-(-1)^n\,yi+Hb)] \qquad \text{Equation 49}$$

The value of v is given as follows: if u is an even number, then v=u; if u is an odd number, then v=u−1.

If the image reconstruction point is tentatively regarded as the reflection source, and the beam path wherein an ultrasonic wave reflected from the point reflection source reaches the receiving probe 7B and it is received as an echo is considered, then these angles θ 1b through θ ub will be as set forth below.

Angle θ 1b corresponds to a path wherein the ultrasonic wave reflected at the image reconstruction point directly reaches the receiving probe 7B. If the path length of one way in this case is taken as w1b, then w1b is determined by equation 50 shown below:

$$w1b = SQRT\,[(xi-xr)^2 + (yi+Hb)^2] \qquad \text{Equation 50}$$

Angle θ 2b corresponds to a beam path wherein the ultrasonic wave reflected at the image reconstruction point bounces once on the bottom 4 before it reaches the receiving probe 7B. If the path length of one way in this case is taken as w2b, then w2b is determined by equation 51 shown below:

$$w2b = SQRT\,[(xi-xr)^2 + (2t-yi+Hb)^2] \qquad \text{Equation 51}$$

Angle θ 3b corresponds to a beam path wherein the ultrasonic wave reflected at the image reconstruction point bounces once on the surface 3 and then bounces once on the bottom 4 before it reaches the receiving probe 7B. If the path length of one way in this case is taken as w3b, then w3b is determined by equation 52 shown below:

$$w3b = SQRT\,[(xi-xr)^2 + (2t+yi+Hb)^2]$$ Equation 52

Angle θ 4b corresponds to a beam path wherein the ultrasonic wave reflected at the image reconstruction point bounces once on the bottom 4, then bounces once on the surface 3, and further bounces once on the bottom 4 before it reaches the receiving probe 7B. If the path length of one way in this case is taken as w4b, then w4b is determined by equation 53 shown below:

$$w4b = SQRT\,[(xi-xr)^2 + (4t-yi+Hb)^2]$$ Equation 53

The same applies to θ 5b through θ ub and the description therefor will be omitted because it can be inferred without the need for description in particular. If one way of the path length corresponding to angle θ ub is taken as wub, then wub is given by equation 54 shown below:

$$wub = SQRT\,[(xi-xr)^2 + (vt-(-1)^n\,yi+Hb)^2]$$ Equation 54

In step 40, it is determined whether θ 1b through θ ub obtained by the calculation in step 39 lie in the effective beam width of the received ultrasonic beam related to the receiving probe 7B. And those that lie in the effective beam width of the received ultrasonic beam are selected among θ 1b through θ ub. More specifically, assuming kb as integers from 1 to u, θ kb which satisfies the conditional equation 55 shown below is selected. The those that have been selected as θ kb satisfying the above conditional equation are denoted as θ pb through θ qb. The values of pb and qb take the integers which fall in the range from 1 to u.

$$\Theta Lb \leq \theta\,kb \leq \Theta\,Hb$$ Equation 55

If no θ kb which satisfies the above conditional equation exists, then the program proceeds to step 49. This step 49 will be discussed later.

In step 41, the propagation paths of the ultrasonic beams associated with receiving which correspond respectively to θ pb through θ qb selected in step 40 are extracted. More specifically, in respective angles θ pb through θ qb, the propagation paths (the propagation path on the way back) along which the ultrasonic wave reflected at the image reconstruction point (xi, yi) reaches the receiving probe 7B are extracted. Further, beam path lengths wpb through wqb respectively corresponding to angles θ pb through θ qb are calculated.

In step 42, based on the propagation paths on the way of the ultrasonic beams extracted in step 37 and the propagation paths on the way back extracted in step 40, all combinations of round trip propagation paths composed of the aforesaid outbound and inbound propagation paths are extracted. As previously mentioned, the outbound propagation paths refer to the propagation paths in which the ultrasonic wave transmitted from the transmitting probe 7A reaches the image reconstruction point (xi, yi), and the inbound propagation paths refer to the propagation paths in which the ultrasonic wave reflected at the image reconstruction point (xi, yi) reaches the receiving probe 7B. There may be a combination wherein the outbound propagation path corresponds to one angle among θ pa through θ qa, while the angle corresponding to the inbound propagation path corresponds to one angle among θ pb through θ qb. Thus, a variety of round trip propagation paths are likely to exist.

Next, on all the combinations of the round trip propagation paths extracted as mentioned above, the round trip beam path lengths thereof are calculated according to wpa through wqa which denote the outbound beam path lengths and wpb through wqb which denote the inbound beam path lengths. Thus, every possible round trip beam path length should have been calculated.

In step 43, on each of all the round trip beam path lengths obtained in step 42, the time when the echo is to be received is determined according to the velocity of sound in the test object 1 in the echo waveforms corresponding to the positions of the combinations of the spacial positions of the transmitting probe 7A selected in step 34 and the spatial positions of the receiving probe 7B selected in step 38, and the amplitudes of the echos corresponding to the time are called up. Next, the amplitudes of the echos called up for the respective round trip beam path lengths are added, and the result of the addition is added to P (xi, yi).

In step 44, it is determined whether the signal processing from step 38 through step 43 has been completed over the entire scanning zone of the receiving probe 7B or over a predetermined scanning zone. If the determination result is negative, then the program goes to step 49; if it is affirmative, then the program proceeds to step 45.

In step 49, the receiving probe 7B is moved to another spatial position and the signal processing from step 38 to step 43 is continued. Specifically, in step 38, a new spacial position (the position after the aforesaid movement) of the receiving probe 7B excluding the spatial positions selected previously is selected within the scanning zone of the receiving probe 7B and the signal processing up to step 44 is implemented.

In step 45, it is determined whether the signal processing from step 34 through step 44 has been completed over the entire scanning zone or a predetermined scanning zone of the transmitting probe 7A. If the determination result is negative, then the program goes to step 48; if it is affirmative, then the program proceeds to step 46.

In step 48, the transmitting probe 7A is moved to another spatial position and the signal processing from step 34 to step 45 is continued. Specifically, in step 34, a new spacial position (the position after the aforesaid movement) of the transmitting probe 7A excluding the spacial positions selected previously is selected within the scanning zone of the transmitting probe 7A and the signal processing up to step 45 is implemented.

In step 46, the value of P (xi, yi) or an absolute value thereof or a square value of the absolute value or the like is output as a reproduced image at the image reconstruction point (xi, yi).

In step 47, it is determined whether the signal processing from step 32 to step 46 has been completed on all predetermined reconstruction points or established reconstruction points in the predetermined image reconstruction zone. If the determination result is negative, then the program proceeds to step 50. If the determination result is affirmative, then it means that all signal processing in the signal processor 84A has been completed.

In step 50, another predetermined image reconstruction point is specified in a predetermined image reconstruction zone, and the signal processing from step 32 to step 47 is carried out.

In step 43 of the signal processing described above, as in the case of the first embodiment, if the amplitude of the echo of the time corresponding to a round trip path length has a value which is not more than a predetermined signal-to-noise ratio, then processing with this amplitude taken as zero may, in some cases, reduce the influences by noises on a reproduced image acquired as a final result. In such a case, only path lengths that have significant corresponding echo amplitudes are selected among all the possible round trip path lengths which have been extracted in step 42, and the amplitudes of echos corresponding thereto are added and the addition result is added to P (xi, yi) to enable a preferable result to be obtained.

The method whereby a refraction angle is selected and a round trip beam propagation path is extracted according to the refraction angle is just one extracting method; other methods are possible. Further, it is not always necessary to determine all round trip beam propagation paths; obtaining several candidates is adequate.

As a result of the signal processing described above, the result of the inspection in the test object 1 in this second embodiment has been acquired in terms of an image. The operation and advantage of the second embodiment will now be described.

Unlike the prior art, in the second embodiment, consideration has been given also to the reflection of the ultrasonic waves on the bottom 4 and the surface 3 of the test object 1 to obtain candidates of possible ultrasonic beam propagation paths, the ultrasonic beam path lengths corresponding to the candidates have been determined by arithmetic operation, and the amplitudes of the echos in the time positions which correspond to the ultrasonic beam path lengths have been added just like the first embodiment. Further, unlike the first embodiment, the result of the addition has been added in relation to the echos corresponding to the time positions of the combinations of each position of the transmitting probe 7A in the scanning zone of the transmitting probe 7A and each position of the receiving probe 7B in the scanning zone of the receiving probe 7B. The result of the addition has been output as an image at the image reconstruction point. This makes it possible to reproduce an image with consideration given to the ultrasonic beam propagation paths just like the first embodiment. Therefore, an operation and advantage are provided in that more accurate examination result can be obtained than that in the prior art, and the number of additions can be increased in comparison with the first embodiment since the transmitting probe 7A and the receiving probe 7B are used for the spatial scanning, thus providing an operation and advantage in that more accurate inspection results than those obtained in the first embodiment can be acquired in some cases.

If the amplitude of the echo in the time position corresponding to an ultrasonic beam path length of the possible ultrasonic beam propagation path has a value which is not more than a predetermined signal-to-noise ratio, then, as in the case of the first embodiment, only ultrasonic beam paths that have significant corresponding echo amplitude values are selected among the ultrasonic beam propagation paths, and only the amplitudes of echos corresponding thereto are added and the addition result is added to P (xi, yi), thus providing an operation and advantage in that sharper images can be obtained and therefore more accurate examination can be achieved.

Furthermore, if a beam width of −3 dB is used for the transmitted ultrasonic beam as the ultrasonic beam width defined by the foregoing $\Theta$ La and $\Theta$ Ha, and if the beam width of −3 dB in the received ultrasonic beam is used as the ultrasonic beam width defined by the foregoing $\Theta$ Lb and $\Theta$ Hb, then, signal processing based on principal beam can be implemented for both transmission and receiving, thus providing an operation and advantage in that sharper images can be obtained just like the first embodiment.

The second embodiment has referred to a case where an image is reproduced by signal processing by scanning by using the transmitting probe 7A and the receiving probe 7B at a particular value of z on a z-axis perpendicular to the x-axis and the y-axis, i.e. within a section of (x, y) although it is not shown. However, the present invention is not limited thereto and the information on the defect 6 along the z-axis can be also obtained by implementing the same scanning by using the transmitting probe 7A and the receiving probe 7B and signal processing along the z-axis, i.e. at diverse values of z, and by reproducing and displaying the final result in terms of a three-dimensional image in the test object 1, thus providing an operation and advantage which allow effective use for classifying, sorting, or the like of the defect 6 just like the first embodiment.

The second embodiment presents the following operation and advantage in addition to those provided by the first embodiment described above. The characteristic of the reflection from the defect 6 may exhibit spatial directivity, depending on the shape of the defect 6. For instance, if the defect 6 is planar, then an ultrasonic pulse applied to the defect 6 displays mirror reflection or similar thereto. In such a case, the ultrasonic wave launched into the defect 6 is not reflected in the incident direction; it is intensely reflected in an entirely different direction from the incident direction. Hence, the ultrasonic pulse bounced off the defect 6 hardly comes back to the transmitting probe 7A which transmitted the ultrasonic pulse. In this case, the echo from the defect 6 can hardly be received by the probe in the first embodiment. The second embodiment is very likely to be able to receive the echo even if the characteristic of reflection from the defect 6 has the spatial directivity as described above since the second embodiment is provided with the receiving probe 7B separately from the transmitting probe 7A to receive the echos by scanning the receiving probe 7B for scanning. Thus, in comparison with the first embodiment, the second embodiment presents an operation and advantage of improved capability of detecting the defect 6, that is, improved capability of not overlooking the defect 6 in addition to the operation and advantage provided by the first embodiment.

Furthermore, using different refraction angles for the transmitting probe 7A and the receiving probe 7B, respectively, and carrying out the second embodiment by using various different combinations of the refraction angles will provide an operation and advantage in that the probability of detecting the defect 6 without fail is increased and a sharp image thereof can be obtained.

The ultrasonic flaw detection apparatus and the ultrasonic flaw detection method in accordance with the second embodiment of the present invention further present an operation and advantage set forth below. For example, there is such a case as a weld bead wherein it is difficult to transmit and receive ultrasonic waves via the surface of a test object by scanning a transmitting probe and a receiving probe close to a defect because the surface of the test object is badly uneven. In such a case, if there is a defect near the surface of the test object, then no echo from the defect may be obtained by direct scanning because of the aforesaid limitation on the scanning zone of the transmitting probe and the receiving probe wherein ultrasonic waves can be transmitted and received properly. In this case, it is necessary to place the transmitting probe and the receiving probe on the bottom of the test object to use the bottom as the test surface to carry out the flaw detecting examination, or to dispose the transmitting probe on the surface and dispose the receiving probe on the bottom to conduct the flaw detecting examination. If, however, the test object is a part of a structure and the bottom cannot be accessed physically, then it is impossible to use the bottom as the test surface. Thus, since the ultrasonic flaw detection apparatus and the ultrasonic flaw detection method according to the present invention make use of the reflection of ultrasonic waves on a bottom and the reflection of ultrasonic waves on a surface rather than depending merely on direct scanning, they provide an operation and advantage in that the foregoing limitation can be overcome, allowing the flaw detecting examination to be achieved by utilizing such reflections.

In the second embodiment of the invention, the description has been given to the configuration where the transmitting probe and the receiving probe are brought in direct contact with the surface of the test object. However, if the bottom of the test object can also be used as the test surface, then either the transmitting probe or the receiving probe may be disposed on the surface and the other may be disposed on the bottom to carry out the flaw detecting examination according to the same procedure as that of the second embodiment.

So far, the description has been given to cases where the probes are brought in direct contact with the test surfaces of the test object 1. The present invention, however, is not limited thereto; and may be applied to a so-called immersion method or immersion testing in which the test object 1 is immersed in a liquid such as water and the probes transmit and receive ultrasonic waves to and from the test object 1 via the liquid. The present invention may also be applied to a so-called local immersion testing wherein a water film is provided only on acoustic transmitting and receiving surfaces which are the front surfaces of the probes, that is, only in the local space between the probes and the test surfaces of the test object, and ultrasonic waves are transmitted to and received from the test object. The same operations and advantages of the present invention described above can be obtained also in such immersion method, immersion testing, and local immersion testing.

In conjunction with FIG. 1 and FIG. 16, it has been described that the scanners 9, 9A, and 9B have the function for the spatial scanning of the probes 7, 7A, and 7B output the information on the spatial positions of the probes 7, 7A, and 7B and supply it to the position detector 85. However, the function for gathering and outputting the information on the spatial positions of the probes 7, 7A, and 7B may be implemented by position information generators provided independently of the scanners 9, 9A, and 9B. In other words, the information on the spatial positions of the probes 7, 7A, and 7B may alternatively be gathered and output by the position information generators, then supplied to the position detector 85. In this case, the scanners 9, 9A, and 9B are responsible only for the function for the spatial scanning of the probes 7, 7A, and 7B. Further, in this case, it is necessary to connect the position information generators to the controller 81 to exchange various types of signals with the controller 81.

Furthermore, in conjunction with FIG. 1 and FIG. 16, it has been described that the information on the spatial positions of the probes 7, 7A, and 7B are output from the scanners 9, 9A, and 9B and applied to the position detector 85. However, since the information on the spatial scanning zones and the travel distances of the probes 7, 7A, and 7B are controlled and generated by the controller 81, the scanners 9, 9A, and 9B may be responsible only for the spacial scanning function of the probes 7, 7A, and 7B, and the information on the scanning of the probes 7, 7A, and 7B from the controller 81 may be directly supplied to and stored in the signal processor 84A so as to obviate the need for providing the position detector 85.

Third Embodiment

Figure 30:
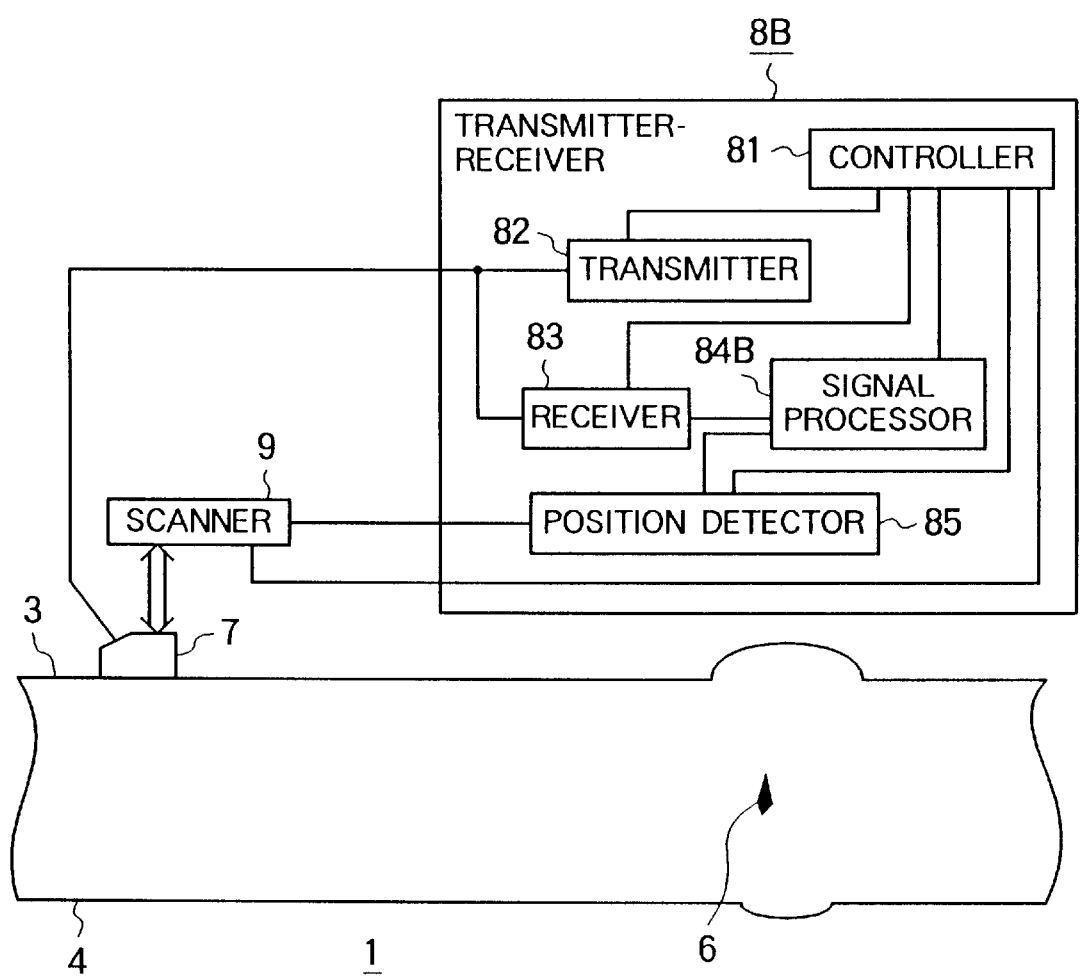
FIG. 30 is a diagram showing the configuration of an ultrasonic flaw detection apparatus according to a third embodiment of the present invention.
Figure 31:
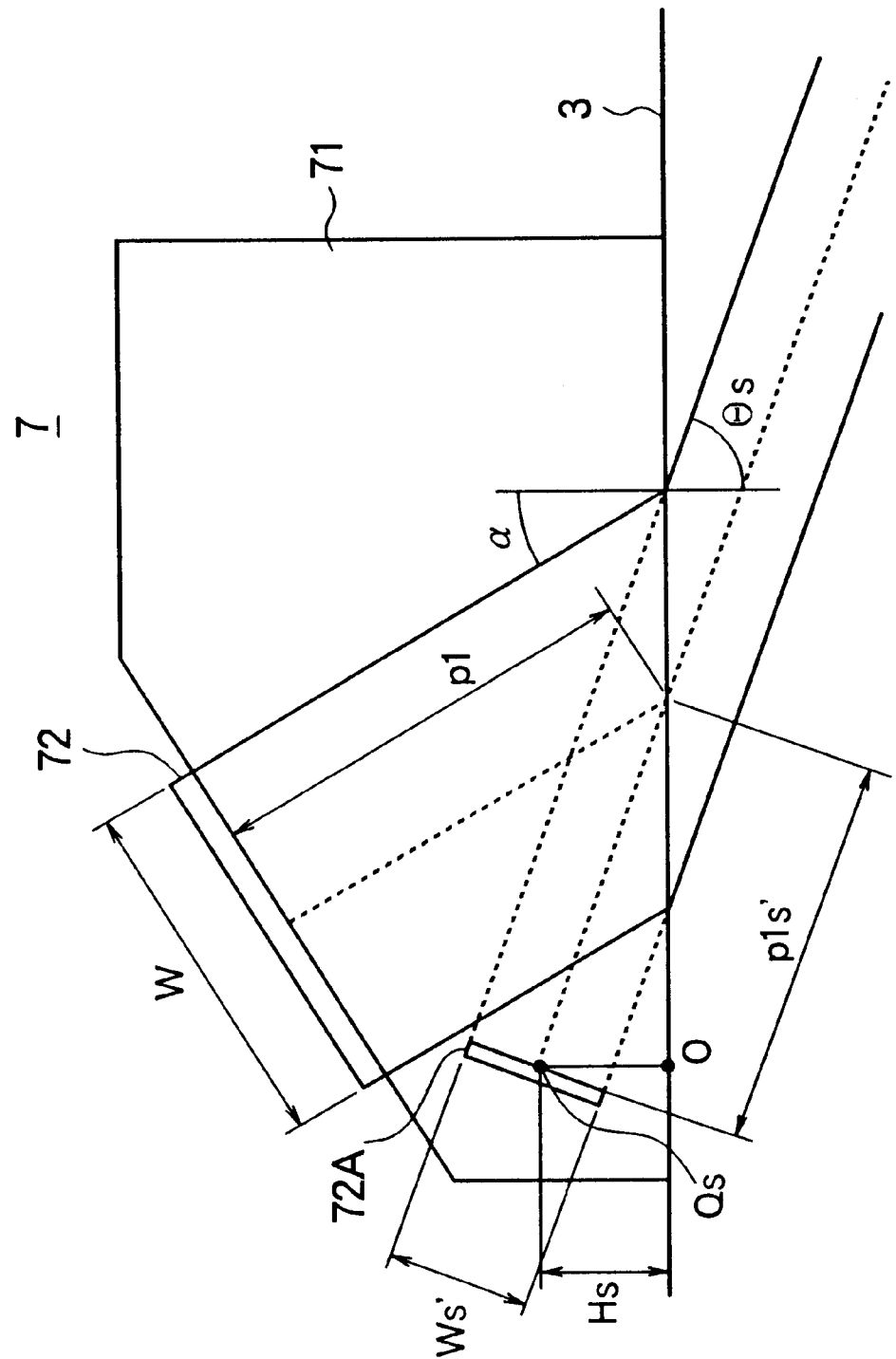
FIG. 31 is a diagram showing the configuration of a probe of the ultrasonic flaw detection apparatus according to the third embodiment of the present invention.

Referring to FIG. 30 and FIG. 31, the configuration of the ultrasonic flaw detection apparatus according to a third embodiment of the present invention will be described. FIG. 30 is a block diagram showing the configuration of the ultrasonic flaw detection apparatus according to the third embodiment of the invention. FIG. 31 is a diagram showing the configuration of a probe of the ultrasonic flaw detection apparatus according to the third embodiment of the invention. FIG. 31 has been cited from literature B.

In FIG. 30, the ultrasonic flaw detection apparatus is equipped with: a probe 7 rested on a test object 1, a transmitter-receiver 8B connected to the probe 7, and a scanner 9 for the probe 7.

Further in the drawing, the transmitter-receiver 8B includes a controller 81, a transmitter 82, a receiver 83, a signal processor 84B, and a position detector 85 for detecting the position of the probe 7. The scanner 9 includes a sensor for detecting the position of the probe 7 although it is not shown.

In the drawing, the probe 7 is connected to the transmitter 82 and the receiver 83 by a signal conductor. The receiver 83 is connected to the signal processor 84B. The position detector 85 is connected to the signal processor 84B. The controller 81 is connected to the transmitter 82, the receiver 83, the signal processor 84B, the position detector 85, and the scanner 9.

Further in the drawing, the scanner 9 is connected to the position detector 85. The output signal from the position detecting sensor of the scanner 9 is supplied to the position detector 85. The information on the position of the probe 7 detected by the position detector 85 is supplied to the signal processor 84B.

The signal processor 84B has an internal memory (not shown). Various results obtained by operations and calculations are stored in this memory in the signal processor 84B as needed, and the input signals supplied to the signal processor 84B are also stored therein as needed.

Furthermore, although not shown, the signal processor 84B furnishes signals which indicate processing states to the controller 81 as needed. Based on the input signals, the controller 81 issues control signals to the transmitter 82, the receiver 83, the signal processor 84B, the position detector 85, and the scanner 9 to control them.

In FIG. 31, the probe 7 includes a wedge 71 composed of a material such as acrylic material, and a rectangular or circular transducer 72 composed of a piezoelectric material such as piezoelectric ceramic.

The operation of the probe 7 will be described. In the ultrasonic angle beam flaw detection, transverse waves are often employed as the ultrasonic waves transmitted from the probe 7 into the test object 1. In the probe 7 exclusively designed for transverse waves, longitudinal ultrasonic waves are transmitted from the transducer 72 into the wedge 71. It is designed so that the longitudinal ultrasonic waves transmitted into the wedge 71 are reflected and refracted on the boundary surface between the wedge 71 and the test object 1, namely, the surface 3 of the test object 1, according to the Snell's law of reflection and refraction; therefore, only transverse ultrasonic waves are refracted and propagated into the test object 1. Specifically, the probe 7 is designed to have an incident angle "α" so that the longitudinal waves transmitted from the transducer 72 to the wedge 71 are refracted on the aforesaid boundary surface between the wedge 71 and the test object 1 according to the Snell's law of reflection and refraction and are not launched into the test object 1, only refracted transverse waves being allowed to be launched therein. The transverse ultrasonic waves which have propagated through the test object 1 are received in the reverse order from that described above. Therefore, the probe 7 which has been designed specifically for transverse waves receives, in design, only the transverse ultrasonic waves which have propagated through the test object 1.

The operation of the probe 7 dedicated for transverse waves thus designed can be easily understood in the following way. In FIG. 31, reference numeral 72A denotes an apparent transducer; and "Hs" denotes the height from the surface 3 of the test object 1 to the center of the apparent transducer 72A. Further, "W" denotes the width of the transducer 72, "Ws'" denotes the width of the apparent transducer 72A, "p1" denotes the distance in the wedge, "p1s'" denotes the distance in the apparent wedge, "α" denotes the incident angle of an ultrasonic wave on the boundary surface between the wedge 71 and the surface 3 of the test object 1, and "θ s" denotes a transverse wave refraction angle.

For the purpose of descriptive convenience, the reference numerals and designations used in this specification (the description of the third embodiment) are different from those used in literature B. The correspondence between this specification and literature B is as follows: the designations and reference numerals on the left side of an arrow (→) are those in literature B, while those on the right side thereof are used in the present specification. The height corresponding to that denoted by reference character H in the present specification is not contained in literature B. The position of origin O is different from that shown in literature B; it is defined as a point obtained by projecting the center of the apparent transducer 72A perpendicularly to the surface 3 of the test object 1 as shown in FIG. 31.

Height H of the transducer→Width W of the transducer 72

Apparent height HR of the transducer→Apparent width Ws' of the transducer 72

Distance l 1 in the wedge→Distance p1 in the wedge

Distance l 2 in the wedge converted to the distance in the test object→Apparent distance p1s' in the wedge The expression "apparent" has been used as shown above; this is because, as described in literature B, a longitudinal ultrasonic wave transmitted from the transducer 72 into the wedge 71 is refracted according to the Snell's law of refraction at the boundary surface with respect to the test object 1, namely, the surface 3; therefore, width W of the transducer 72 observed from the test object 1 seemingly becomes Ws' equivalently, and distance p1 in the wedge seemingly becomes p1s' equivalently when it is converted to the distance in the test object 1. Employing these apparent physical quantities enables various types of calculations and signal processing to be achieved by handling the wedge 71 as if it were the test object 1. Thus, the following description will use the apparent transducer 72A, width Ws' thereof, apparent distance P1s' in the wedge, and height Hs related to the center of the apparent transducer 72A. In addition, point Qs is defined as the center of the apparent transducer 72A. The coordinates of point Qs are (0, –Hs).

Because width W of the transducer 72 of the probe 7 is finite, there are refracted longitudinal waves, although in a smaller scale than refracted transverse waves, also in the probe 7 which has been designed as the probe 7 specifically designed for transverse waves extensively used for ultrasonic angle beam flaw detection. In other words, refracted longitudinal waves are transmitted, although in a smaller scale, into the test object 1. The reverse order from the aforesaid order is followed for receiving. Therefore, even the probe 7 designed exclusively for transverse waves undesirably receives the longitudinal waves which have propagated through the test object 1 although at a lower receiving level than the transverse waves which have propagated through the test object 1. Thus, the longitudinal waves are transmitted from the probe 7 into the test object 1, and the longitudinal waves which have propagated through the test object 1 are inevitably received by the probe 7. Regarding these transmitted longitudinal waves and received longitudinal waves, our (the inventors') experiments have revealed that the concept of the apparent distance in the wedge and the apparent transducer may reasonably be applied just as in the case of the transverse waves. Hence, the center of the apparent transducer with respect to longitudinal waves is denoted as point QL although it is not shown. The coordinates of point QL are generally different from those of point Qs for transverse waves. The coordinates of point QL are represented as (xL, –HL).

Referring now to FIG. 32 through FIG. 53, the operation of the ultrasonic flaw detection apparatus according to the third embodiment of the present invention will be described.

Figure 32:
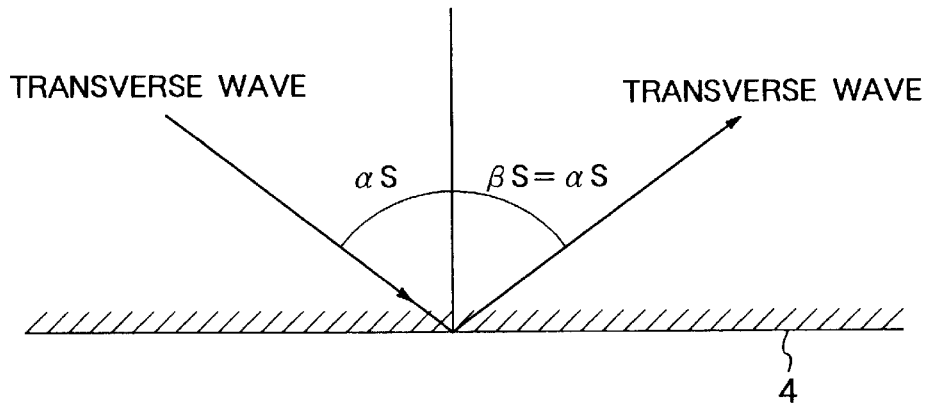
FIG. 32 is a diagram showing a propagation path of an ultrasonic beam for describing the operation of the ultrasonic flaw detection apparatus according to the third embodiment of the present invention.
Figure 33:
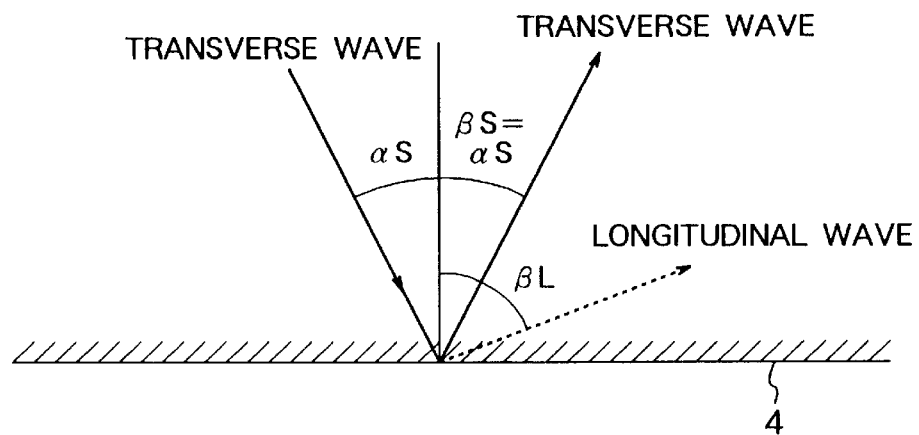
FIG. 33 is a diagram showing a propagation path of an ultrasonic beam for describing the operation of the ultrasonic flaw detection apparatus according to the third embodiment of the present invention.
Figure 34:
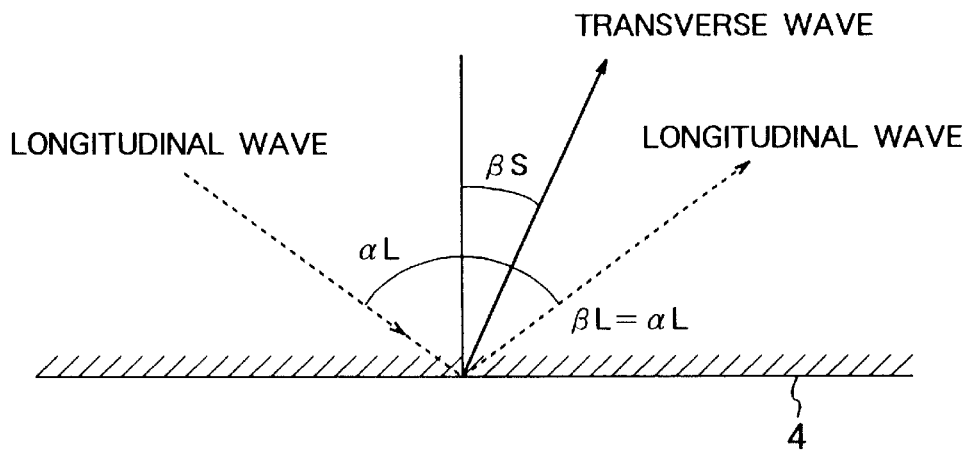
FIG. 34 is a diagram showing a propagation path of an ultrasonic beam for describing the operation of the ultrasonic flaw detection apparatus according to the third embodiment of the present invention.
Figure 52:
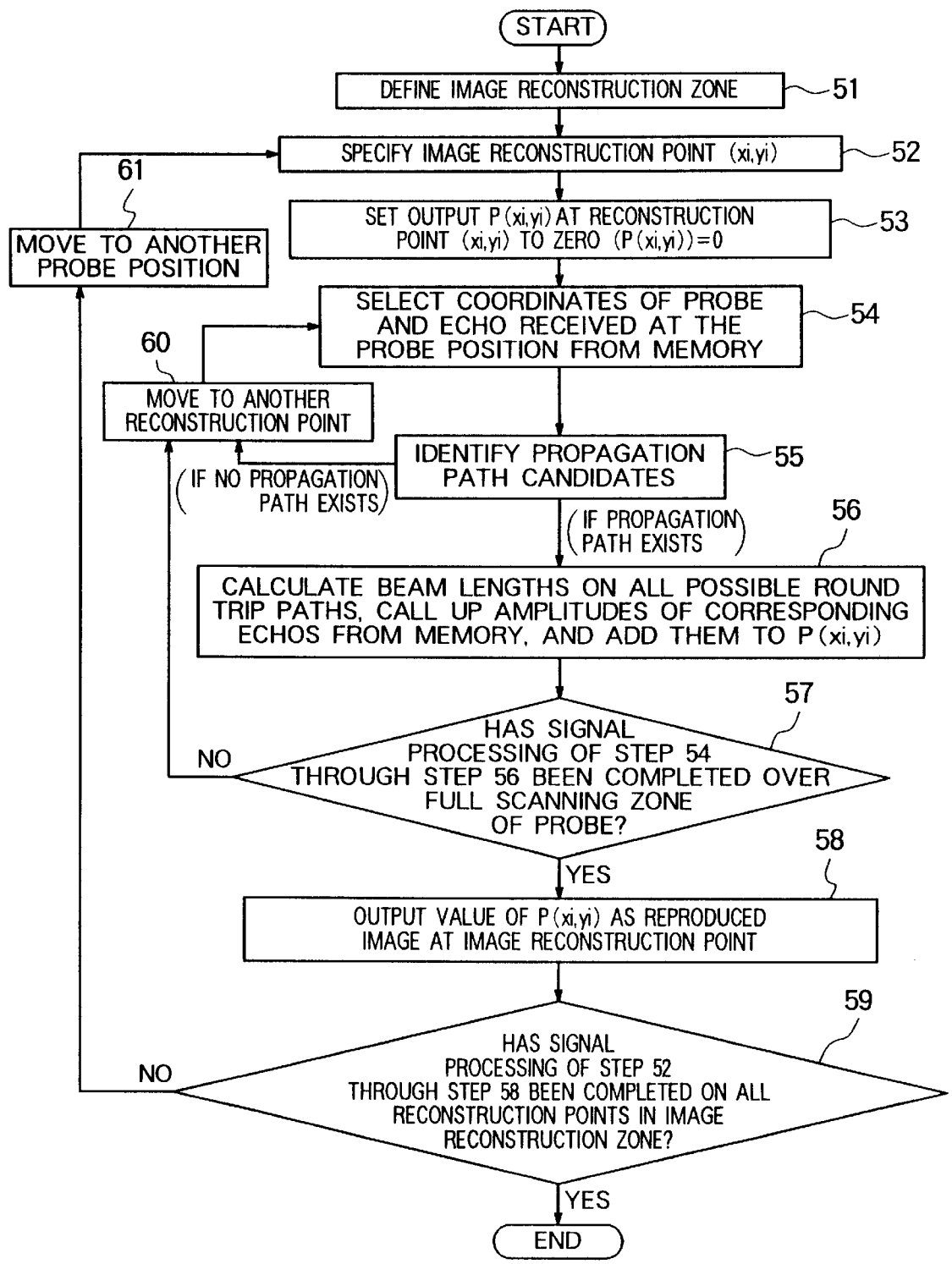
FIG. 52 is a flowchart for describing the signal processing of the ultrasonic flaw detection apparatus according to the third embodiment of the present invention.
Figure 53:
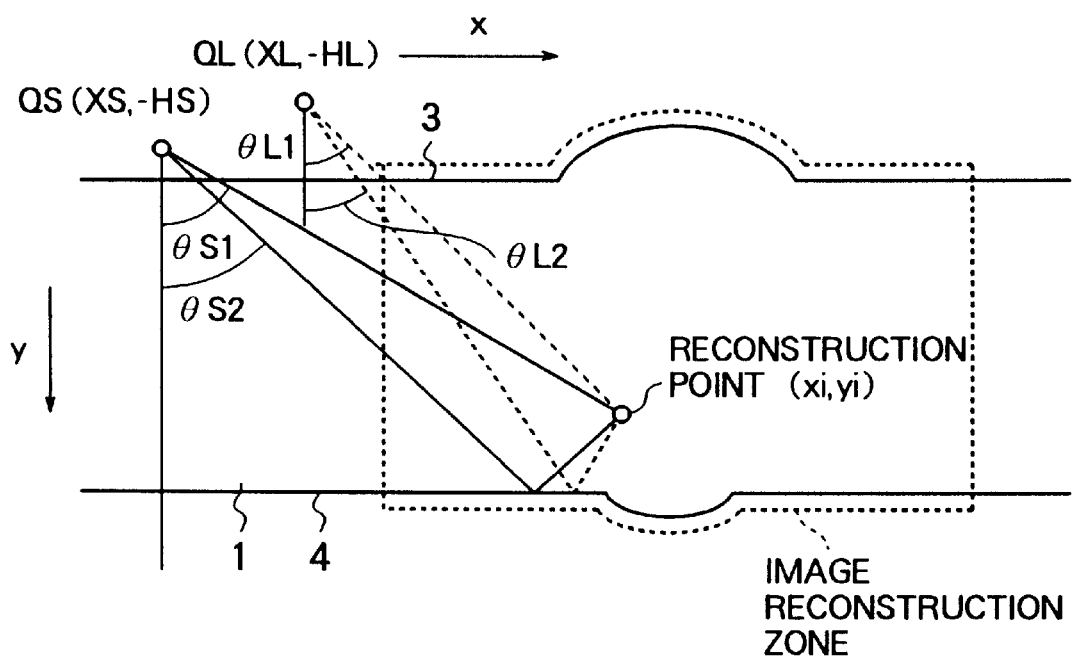
FIG. 53 is a beam propagation path for describing the signal processing of the ultrasonic flaw detection apparatus according to the third embodiment of the present invention.

FIG. 32, FIG. 33, and FIG. 34 are diagrams for describing the characteristics concerning the reflection of ultrasonic waves on the boundary surface between a test object and air. FIG. 35 through FIG. 51 are diagrams illustrating the ultrasonic beam propagation paths for describing the operation of the ultrasonic flaw detection apparatus according to the third embodiment. FIG. 52 is a flowchart for describing the signal processing of the ultrasonic flaw detection apparatus according to the third embodiment. Further, FIG. 53 is a diagram illustrating the beam propagation path for describing the flowchart of the signal processing shown in FIG. 52.

A transmission signal such as a burst signal which has a certain carrier frequency or a pulse having a narrow time width which may be regarded as an impulse is generated and transmitted from a transmitter 82 of a transmitter-receiver 8B to a probe 7. The probe 7 is driven by the transmission signal, and it transmits the ultrasonic pulse at an angle with respect to the test surface of a test object 1, namely, a surface 3 of the test object 1. In this embodiment, the description will be given, taking the surface as the test surface as an example. The test surface, however, is not limited to a surface; and instead may be a bottom or side. The ultrasonic pulse propagates in the test object 1 and is reflected, scattered, and diffracted by a defect 6. The term "reflection" herein is handled as a term which includes such physical phenomena as scattering and diffraction in addition to reflection. This means that the term "reflection" should be interpreted as a term which includes all phenomena wherein ultrasonic waves are affected by the defect 6 and therefore behave differently in propagation from a case where no defect 6 exists. The description will be given, assuming that a distal end diffraction echo or a tip echo which is known to occur at a tip of the defect 6 is also included in the echos reflected by the defect 6. The reflected, scattered and diffracted ultrasonic pulse propagates through the test object 1 and it is received by the probe 7. The received echo is amplified by a receiver 83 before it is sent to a signal processor 84B.

The information on the spatial position of the probe 7 is detected by a scanner 9 and is sent to a position detector 85. The information on the spatial position of the probe 7 is sent from the position detector 85 to the signal processor 84B. The signal processor 84B stores the information on the spatial position of the probe 7 and the received echo.

Then, the probe 7 is moved by the scanner 9 to another spatial position (coordinates). An ultrasonic pulse is transmitted from the probe 7 by the transmission signal, and the echo received from the defect 6 and the information on the spatial position of the probe 7 are transmitted to and stored in the signal processor 84B in the same manner as described above.

This series of operations is conducted over a predetermined scanning zone of the probe 7. After that, the signal processing to be discussed later is carried out in the signal processor 84B.

Before describing the signal processing procedure in the signal processor 84B, the characteristic concerning the reflection of an ultrasonic wave on the boundary surface between the test object 1 and air will be described with reference to FIG. 32, FIG. 33, and FIG. 34. In these drawings, the solid lines with arrows correspond to transverse waves; the directions indicated by the arrows show the directions of propagation. The dotted lines with arrows correspond to longitudinal waves; the directions indicated by the arrows show the directions of propagation. In the description of the third embodiment, in order to distinguish longitudinal waves from transverse waves, the transverse waves will be denoted by the solid lines, while the longitudinal waves will be denoted by the dotted lines in all drawings of the third embodiment. The directions of propagation will be indicated by the arrows for both longitudinal waves and transverse waves. The bottom 4 of the test object 1 will be cited as an example of the boundary surface between the test object 1 and air. It is needless to say that the characteristics related to the reflection of ultrasonic waves to be discussed below are based on the Snell's law of reflection.

FIG. 32 and FIG. 33 illustrate the reflection of a transverse wave which is launched aslant to the bottom 4 after having propagated through the test object 1. FIG. 32 is different from FIG. 33 in that the incident angle denoted by a symbol "α s" in FIG. 32 is larger than that in FIG. 33. As shown in FIG. 32, when the incident angle α s of the transverse waves is large, the ultrasonic waves generated by the reflection on the bottom 4 include only transverse waves. As shown in FIG. 33, however, if the incident angle α s of the transverse waves becomes smaller than a certain value, then the reflection on the bottom 4 produces both transverse waves and longitudinal waves except when α s is zero, that is, when the waves are launched perpendicularly. In FIG. 32 and FIG. 33, the reflection angle of transverse waves which is denoted by a symbol "β s" is equal to the incident angle α s. In FIG. 33, the reflection angle of longitudinal waves which is denoted by a symbol "β L" is larger than the reflection angle β s of transverse waves.

FIG. 34 illustrates the reflection of a longitudinal wave which is launched aslant to the bottom 4 after having propagated through the test object 1. In the drawing, the angle denoted by a symbol "α L" is the incident angle of the longitudinal wave. The angle denoted by a symbol "β L" is the reflection angle of the longitudinal wave; the angle denoted by a symbol "β s" indicates the reflection angle of a transverse wave. When the longitudinal wave is launched aslant on the bottom 4, the reflection thereof on the bottom 4 produces both transverse wave and longitudinal wave regardless of whether the incident angle α L is large or small except when it is zero, that is, when the wave is launched perpendicularly. The reflection angle β L of the longitudinal wave is equal to the incident angle α L of the longitudinal wave. The reflection angle β s of the transverse wave is smaller than the reflection angle β L of the longitudinal wave.

Considering the foregoing characteristics concerned with the reflection of ultrasonic waves which have been described with reference to FIG. 32, FIG. 33, and FIG. 34, the propagation characteristics of the ultrasonic beams in the test object 1 will be described. Firstly, the propagation paths of ultrasonic beams will be discussed with reference to FIG. 35. In the drawing, the horizontal direction is taken on the x-axis, while the vertical direction is taken on the y-axis.

It is assumed that a point reflection source which corresponds to the defect 6 is located at (x0, y0). Consideration will be given to a case where the ultrasonic wave launched into the test object 1 is a transverse wave. The transverse ultrasonic beam transmitted from the apparent transducer 72A diverges due to diffraction. In the drawing, the thick solid line indicates the centerline of the beam. The thin solid lines indicate the lines which connect the points at which the sound pressure is −3 dB in, for example, from the sound pressure on the centerline in the ultrasonic beams in transmission or reception. In other words, the zone defined by the two thin solid lines corresponds to an effective beam width in the transmission of transverse waves or the reception of transverse waves. The refraction angles corresponding to the two thin solid lines are denoted as $\Theta$ sL and $\Theta$ sH as shown in the drawing. In this embodiment, the beam width of −3 dB is used, but it is not limited thereto; it may be −6 dB, −9 dB, or −12 dB according to the application or purpose, or other value may be used to define the effective beam width.

Figure 35:
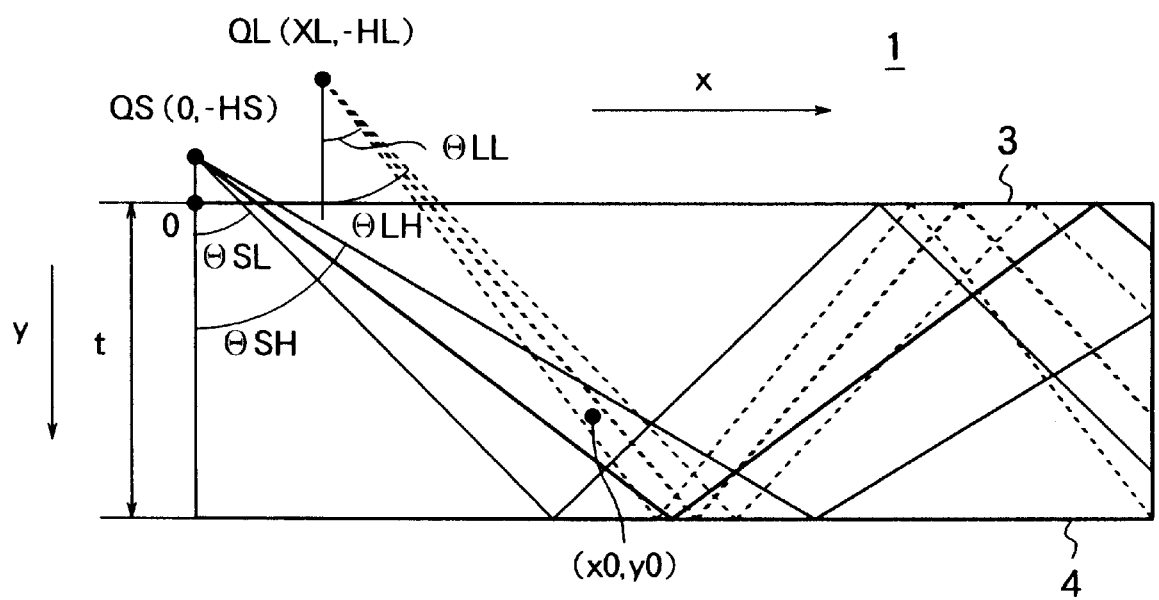
FIG. 35 is a diagram showing a propagation path of an ultrasonic beam for describing the operation of the ultrasonic flaw detection apparatus according to the third embodiment of the present invention.

Further, in FIG. 35, the thick dotted line indicates the centerline of the beam related to a longitudinal wave. The thin dotted lines indicate the lines which connect the points at which the sound pressure is −3 dB in, for example, from the sound pressure on the centerline in the longitudinal ultrasonic beams in transmission or reception. In other words, the zone defined by the two thin dotted lines corresponds to an effective beam width in the transmission of longitudinal waves or the reception of longitudinal waves. The angles corresponding to the two thin dotted lines are denoted as $\Theta$ LL and $\Theta$ LH as shown in the drawing. These angles correspond to the refraction angles $\Theta$ sL and $\Theta$ sH, respectively, for the transverse wave. In this embodiment, the beam width of −3 dB is used, but is not limited thereto. Instead may be −6 dB, −9 dB, or −12 dB according to the application or purpose, or an other value may be used to define the effective beam width.

Referring now to FIG. 36 through FIG. 51, the sound rays in the foregoing beam widths will be discussed. In FIG. 36 through FIG. 51, an origin (0, 0) of the coordinates is established at a point where the center of the apparent transducer 72A is projected onto the surface 3 of the test object 1 along the y-axis as in the case of FIG. 31. Point Qs denotes the center of the apparent transducer 72A; the coordinates thereof is (0, −Hs). A blank circle mark located at (x0, y0) denotes a reflection source which corresponds to the defect 6.

Figure 36:
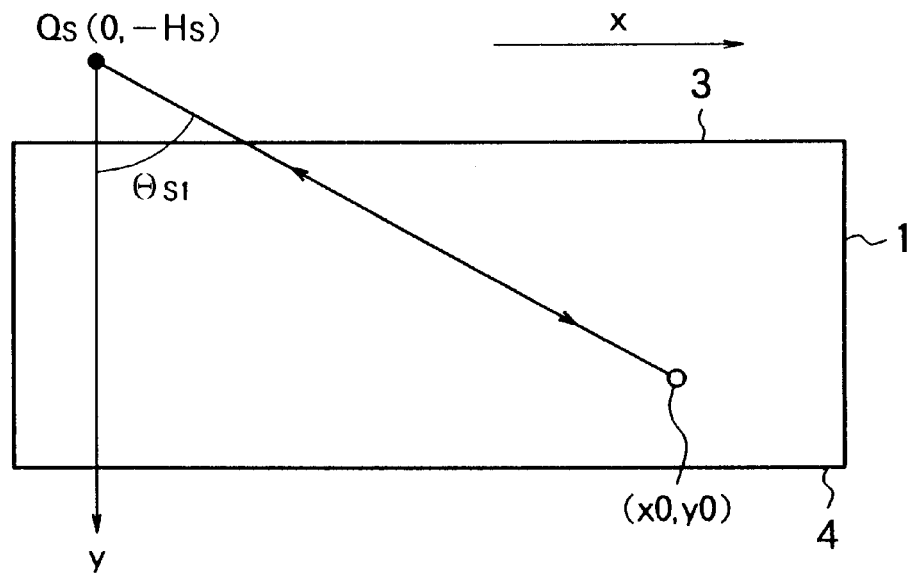
FIG. 36 is a diagram showing a propagation path of an ultrasonic beam for describing the operation of the ultrasonic flaw detection apparatus according to the third embodiment of the present invention.

As shown in FIG. 36, if a sound ray equivalent to refraction angle $\Theta$ s1 exists in the foregoing beam width, that is, if $\Theta$ sL $\leq \Theta$ s1 $\leq \Theta$ sH, then the propagation path of the ultrasonic beam indicated by the solid line with arrows may exist. At this time, the transverse ultrasonic wave transmitted from the probe 7 and launched into the test object 1 is directly applied to the defect 6 and directly reflected by the defect 6 as a transverse wave, then received as an echo by the probe 7.

Figure 37:
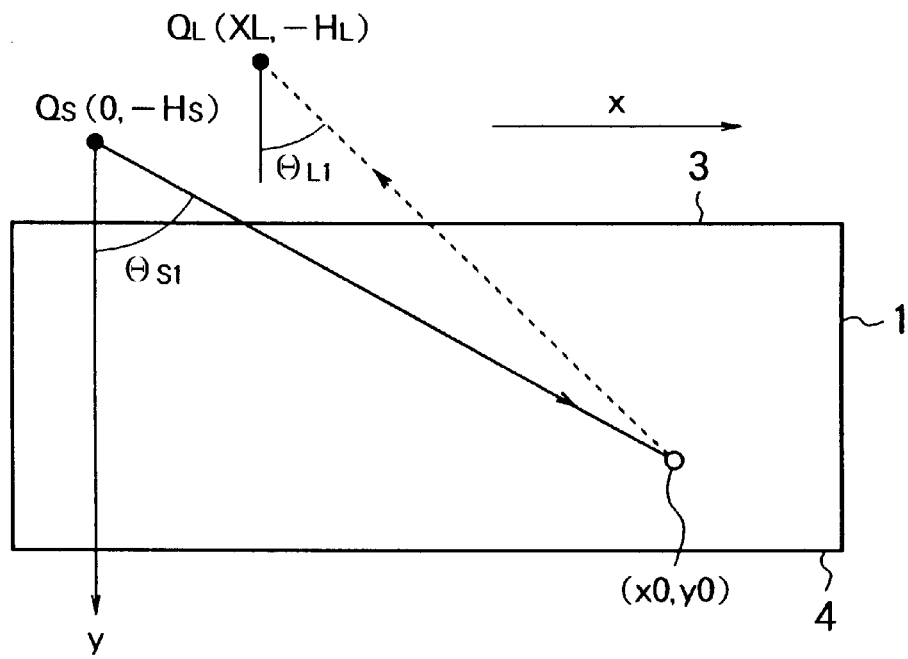
FIG. 37 is a diagram showing a propagation path of an ultrasonic beam for describing the operation of the ultrasonic flaw detection apparatus according to the third embodiment of the present invention.

In FIG. 37, the transverse ultrasonic wave directly applied to the defect 6 may develop a component which is mode-converted to a longitudinal wave and reflected as a longitudinal wave, depending on the properties of the defect 6.

The reflected longitudinal ultrasonic wave is directly received as an echo by the probe 7, although at a low level, if the angle denoted by a symbol "Θ L1" in the drawing exists in the effective beam width for the reception of longitudinal waves as shown by the dotted line with an arrow in the drawing, i.e. if Θ LL≦Θ L1≦Θ LH. In the drawing, point QL denotes the center of the apparent transducer for longitudinal waves. Point QL is, in practice, located in the vicinity of point Qs; however, for easier understanding, these two points QL and Qs are drawn far apart from each other in FIG. 37. The same will apply to the following description.

Figure 38:
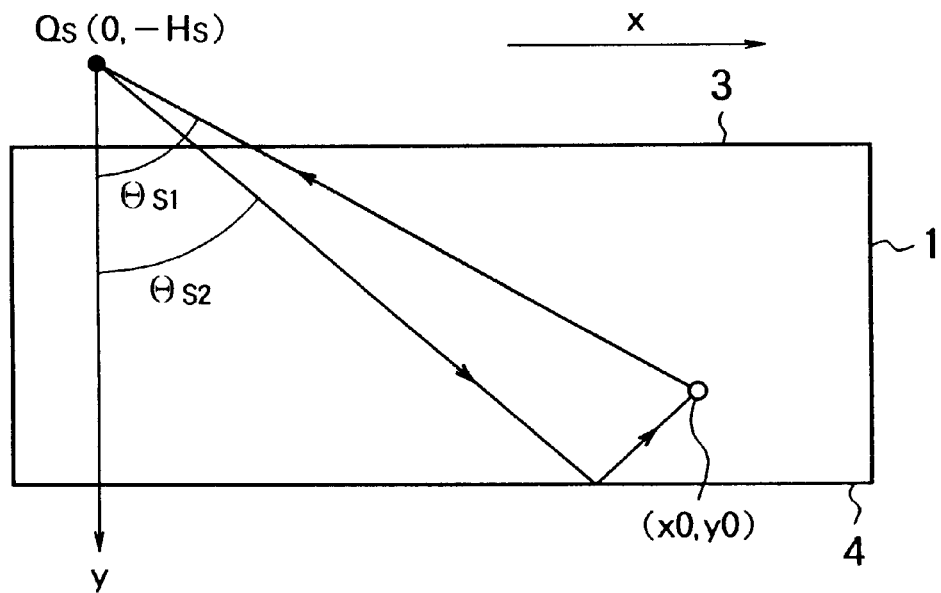
FIG. 38 is a diagram showing a propagation path of an ultrasonic beam for describing the operation of the ultrasonic flaw detection apparatus according to the third embodiment of the present invention.

As shown in FIG. 38, if a sound ray equivalent to refraction angle Θ s1 exists in the foregoing transverse beam width, and a sound ray equivalent to refraction angle Θ s2 also exists in the foregoing transverse beam width, that is, if Θ sL≦Θ s1≦Θ sH and also Θ sL≦Θ s2≦Θ sH, then a propagation path may exist wherein a transverse ultrasonic wave transmitted from the probe 7 into the test object 1 is reflected as a transverse ultrasonic wave once on the bottom 4, applied to the defect 6, reflected by the defect 6 as a transverse ultrasonic wave, then it directly reaches the probe 7 to be received as an echo as shown by the solid line with arrows.

Although not shown, it is possible that a propagation path opposite from the one described above exists. More specifically, the transverse ultrasonic wave transmitted from the probe 7 into the test object 1 directly hits the defect 6; is reflected as the transverse ultrasonic wave by the defect 6 and reflected as the transverse ultrasonic wave once on the bottom 4, then it reaches the probe 7 to be received as an echo.

Figure 39:
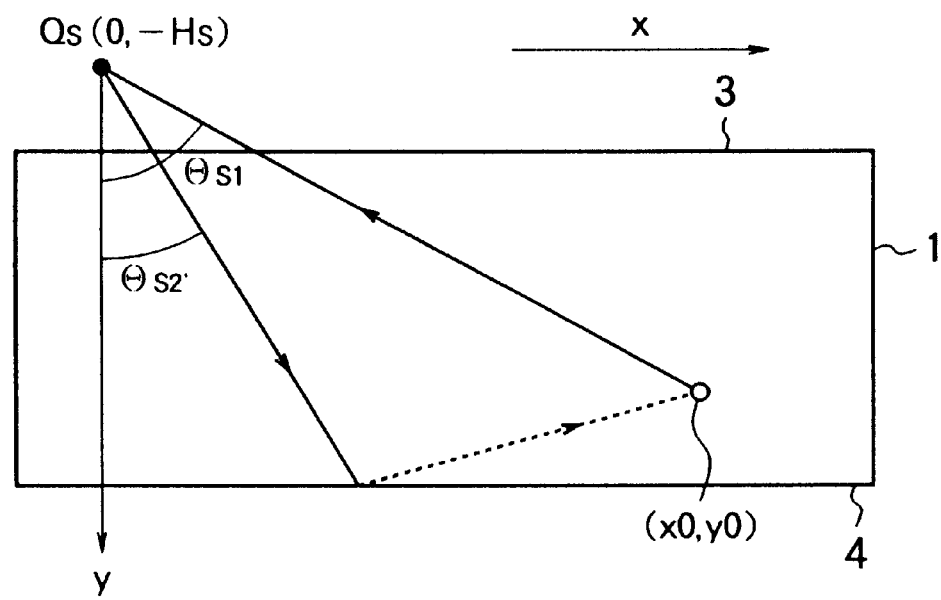
FIG. 39 is a diagram showing a propagation path of an ultrasonic beam for describing the operation of the ultrasonic flaw detection apparatus according to the third embodiment of the present invention.

Further, if Θ sL≦Θ s1≦Θ sH and also Θ sL≦Θ s2'≦Θ sH at the same time, then there is a likelihood that a propagation path shown in FIG. 39 exists. Specifically, the propagation path may exist wherein a transverse ultrasonic wave transmitted from the probe 7 into the test object 1 as indicated by the solid line with an arrow is reflected as a longitudinal ultrasonic wave once on the bottom 4, applied to the defect 6, mode-converted and reflected by the defect 6 as a transverse ultrasonic wave as indicated by the dotted line with an arrow, then it directly reaches the probe 7 to be received as an echo as shown by the solid line with arrows.

Although not shown, it is possible that a propagation path opposite from the one shown in FIG. 39 exists. More specifically, the transverse ultrasonic wave transmitted from the probe 7 into the test object 1 is mode-converted and reflected by the defect 6 as a longitudinal ultrasonic wave, and is reflected once on the bottom 4 as the transverse ultrasonic wave by the defect 6, then is reflected once on the bottom 4 as the transverse ultrasonic wave before reaching the probe 7 to be received as an echo.

Furthermore, if Θ sL≦Θ s1≦Θ sH, and Θ sL≦Θ s2≦Θ sH, and Θ sL≦Θ s2'≦Θ sH, and Θ LL≦Θ L1≦Θ LH, and Θ LL≦Θ L2≦Θ LH, and Θ LL≦Θ L2'≦Θ LH at the same time, then there is a likelihood that the propagation paths shown in FIG. 40 through FIG. 43 exist.

Figure 40:
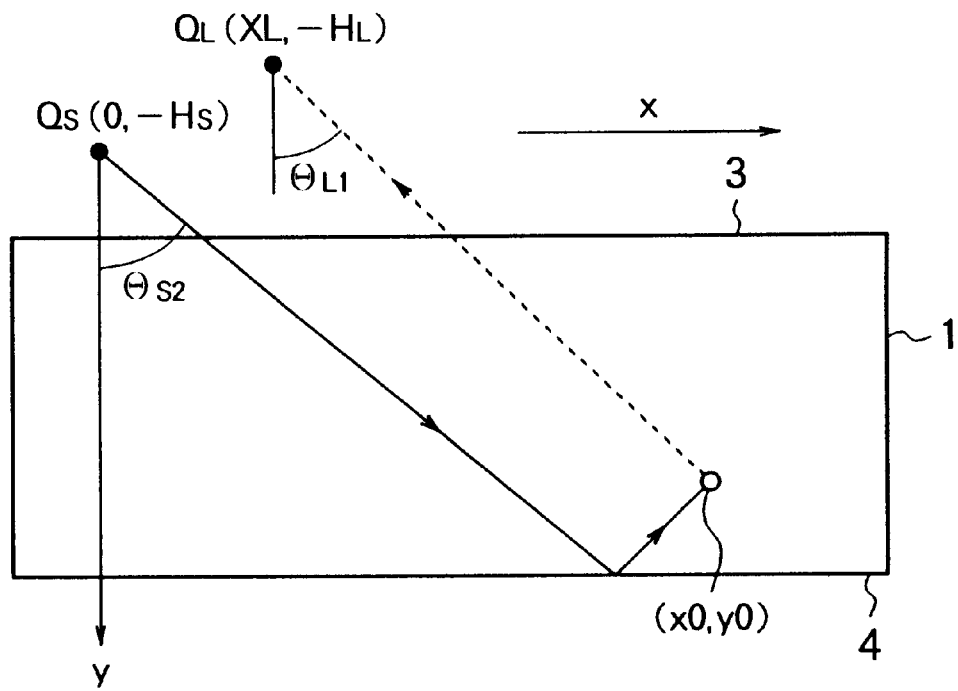
FIG. 40 is a diagram showing a propagation path of an ultrasonic beam for describing the operation of the ultrasonic flaw detection apparatus according to the third embodiment of the present invention.

In FIG. 40, a transverse ultrasonic wave transmitted from the probe 7 into the test object 1 as indicated by the solid line with the arrow is reflected once as the transverse ultrasonic wave on the bottom 4 as indicated by the solid line with the arrow, then hits the defect 6 and is mode-converted by the defect 6 and reflected as a longitudinal ultrasonic wave as indicated by the dotted line with the arrow before directly reaching the probe 7 to be received as an echo.

Figure 41:
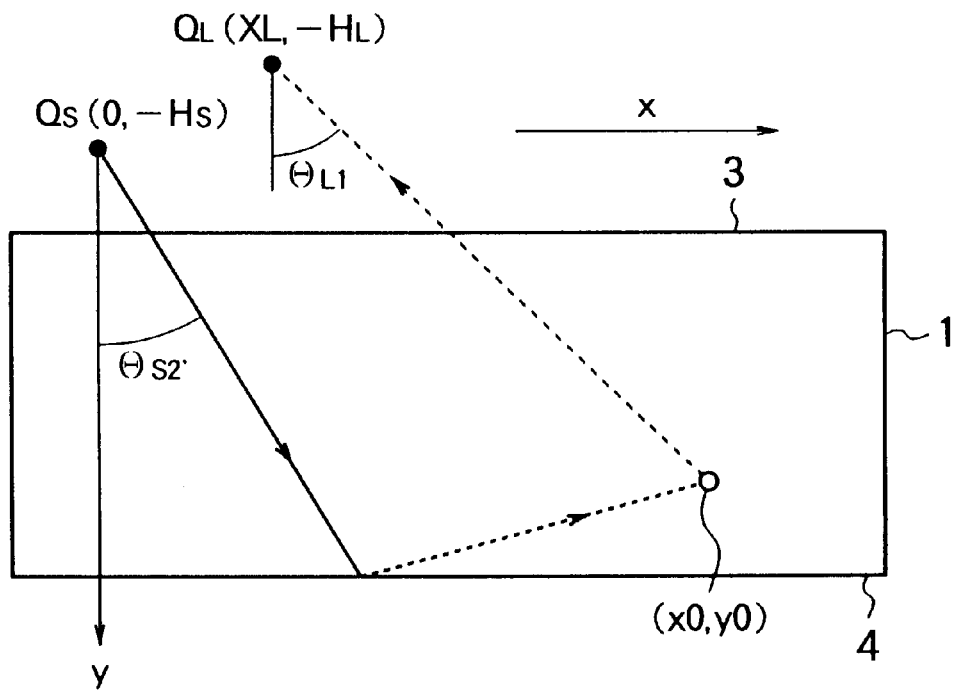
FIG. 41 is a diagram showing a propagation path of an ultrasonic beam for describing the operation of the ultrasonic flaw detection apparatus according to the third embodiment of the present invention.

In FIG. 41, a transverse ultrasonic wave transmitted from the probe 7 into the test object 1 as indicated by the solid line with the arrow is reflected once as the longitudinal ultrasonic wave on the bottom 4 as indicated by the dotted line with the arrow, then hits the defect 6 and it is reflected by the defect 6 as a longitudinal ultrasonic wave as indicated by another dotted line with the arrow before directly reaching the probe 7 to be received as an echo.

Figure 42:
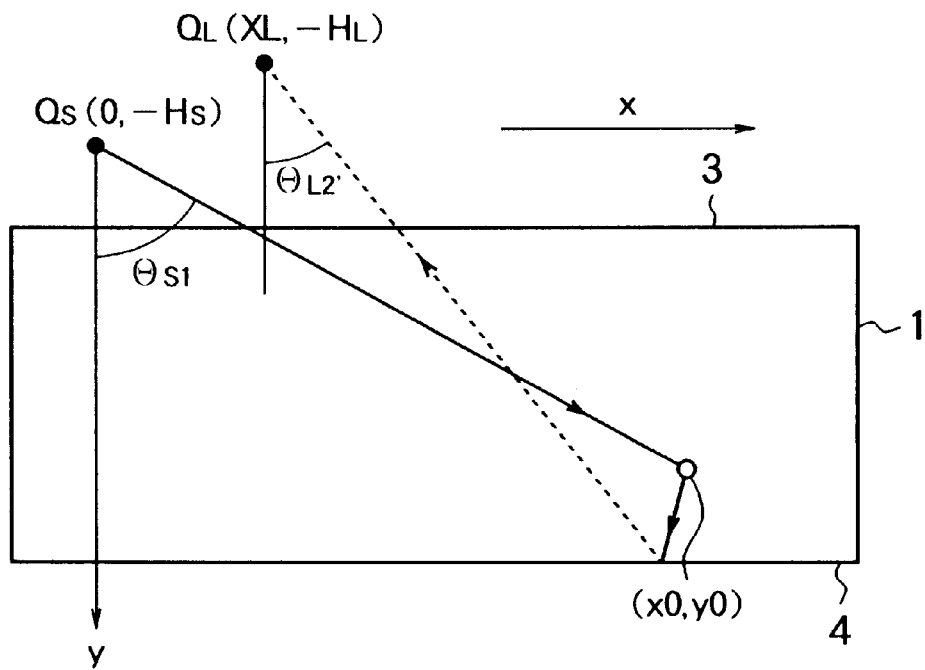
FIG. 42 is a diagram showing a propagation path of an ultrasonic beam for describing the operation of the ultrasonic flaw detection apparatus according to the third embodiment of the present invention.

In FIG. 42, a transverse ultrasonic wave transmitted from the probe 7 into the test object 1 as indicated by the solid line with the arrow directly hits the defect 6 and is reflected by the defect 6 as the transverse ultrasonic wave as indicted by another solid line with the arrow, then is reflected once on the bottom 4 as a longitudinal ultrasonic wave as indicated by the dotted line with an arrow before directly reaching the probe 7 to be received as an echo.

Figure 43:
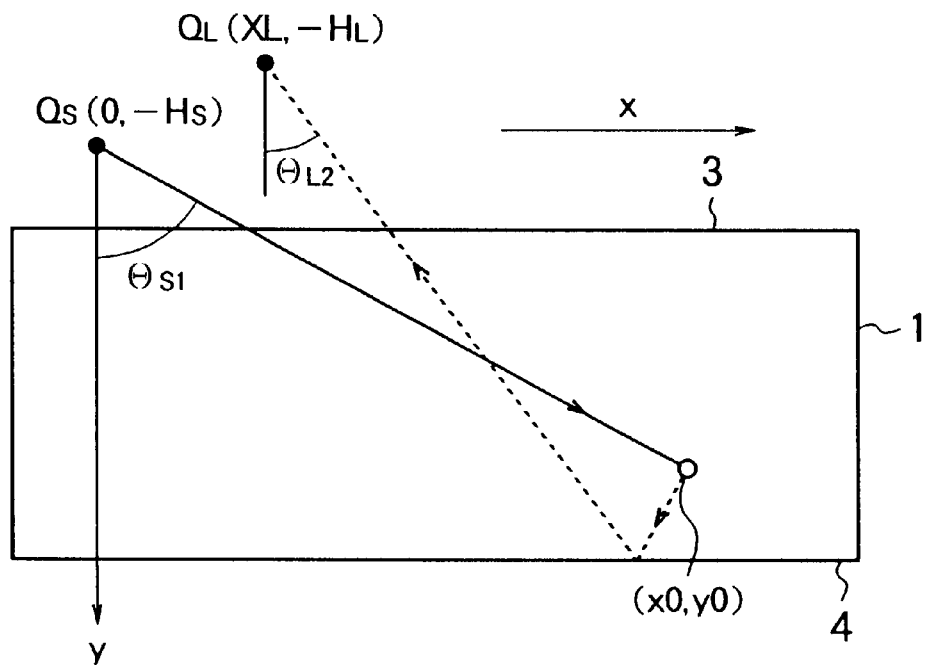
FIG. 43 is a diagram showing a propagation path of an ultrasonic beam for describing the operation of the ultrasonic flaw detection apparatus according to the third embodiment of the present invention.

In FIG. 43, a transverse ultrasonic wave transmitted from the probe 7 into the test object 1 as indicated by the solid line with the arrow directly hits the defect 6 as shown by another solid line with the arrow and is mode-converted and reflected by the defect 6 as a longitudinal ultrasonic wave as shown by the dotted line with the arrow. After that, it is reflected once on the bottom 4 as the longitudinal ultrasonic wave as indicated by another dotted line with the arrow before directly reaching the probe 7 to be received as an echo.

In the propagation paths shown in FIG. 40 through FIG. 43, the receiving level is low at the probe 7 dedicated to transverse waves as described above since the longitudinal waves which have propagated through the test object 1 are received by the probe 7 as in the case of the propagation path illustrated in FIG. 37.

Further, if Θ sL≦Θ s2≦Θ sH, and Θ sL≦Θ s2'≦Θ sH, and Θ LL≦Θ L2≦Θ LH, and Θ LL≦Θ L2'≦Θ LH at the same time, then there is a likelihood that the propagation paths shown in FIG. 44 through FIG. 51 exist.

Figure 44:
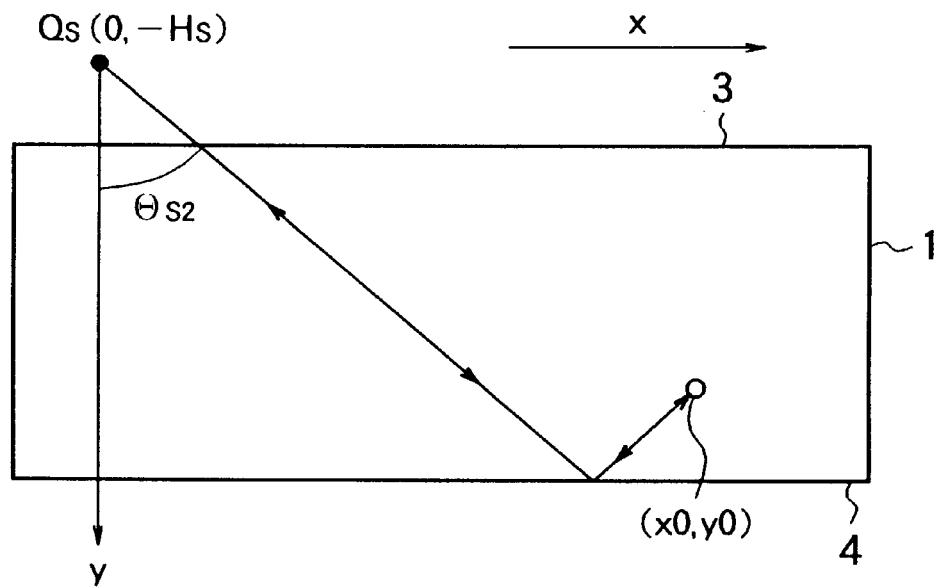
FIG. 44 is a diagram showing a propagation path of an ultrasonic beam for describing the operation of the ultrasonic flaw detection apparatus according to the third embodiment of the present invention.

In FIG. 44, a transverse ultrasonic wave transmitted from the probe 7 is reflected once as the transverse ultrasonic wave on the bottom 4 as indicated by the solid line with the arrow, then hits the defect 6 and is reflected as a transverse ultrasonic wave by the defect 6 as indicated by the solid line with the arrow. After that, it is reflected once as a transverse ultrasonic wave on the bottom 4 before it reaches the probe 7 to be received as an echo as indicated by the solid line with the arrow.

Figure 45:
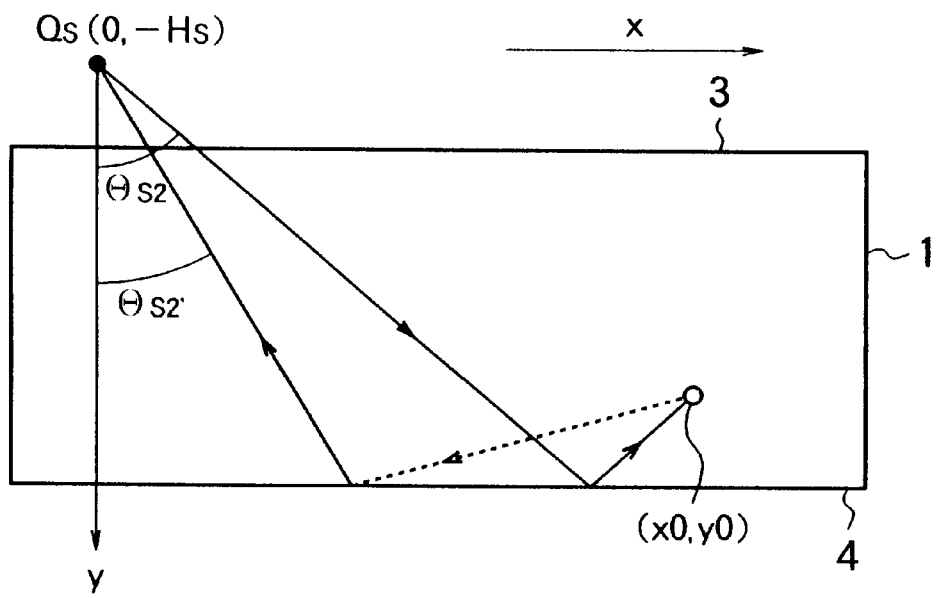
FIG. 45 is a diagram showing a propagation path of an ultrasonic beam for describing the operation of the ultrasonic flaw detection apparatus according to the third embodiment of the present invention.

In FIG. 45, a transverse ultrasonic wave transmitted from the probe 7 is reflected once as the transverse ultrasonic wave on the bottom 4 as indicated by the solid line with the arrow, then hits the defect 6 and is reflected as a longitudinal ultrasonic wave by the defect 6 as indicated by the dotted line with the arrow. After that, it is reflected once as a transverse ultrasonic wave on the bottom 4 before it reaches the probe 7 to be received as an echo as indicated by the solid line with the arrow.

Figure 46:
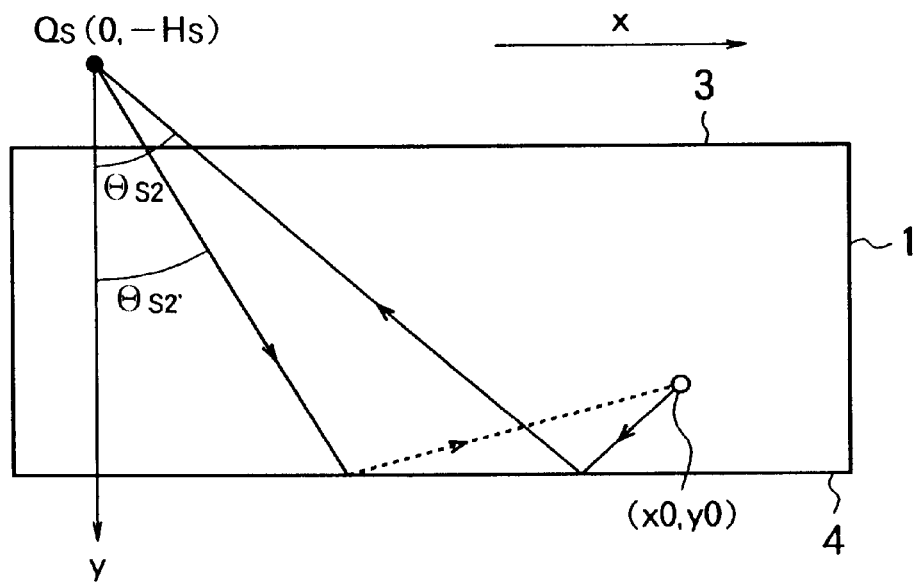
FIG. 46 is a diagram showing a propagation path of an ultrasonic beam for describing the operation of the ultrasonic flaw detection apparatus according to the third embodiment of the present invention.

In FIG. 46, a transverse ultrasonic wave transmitted from the probe 7 is reflected once as the longitudinal ultrasonic wave on the bottom 4 and hits the defect 6 as indicated by the dotted line with the arrow. Then it is reflected as a transverse ultrasonic wave by the defect 6 as indicated by the solid line with the arrow. After that, it is reflected once as a transverse ultrasonic wave on the bottom 4 before it reaches the probe 7 to be received as an echo as indicated by the solid line with the arrow.

Figure 47:
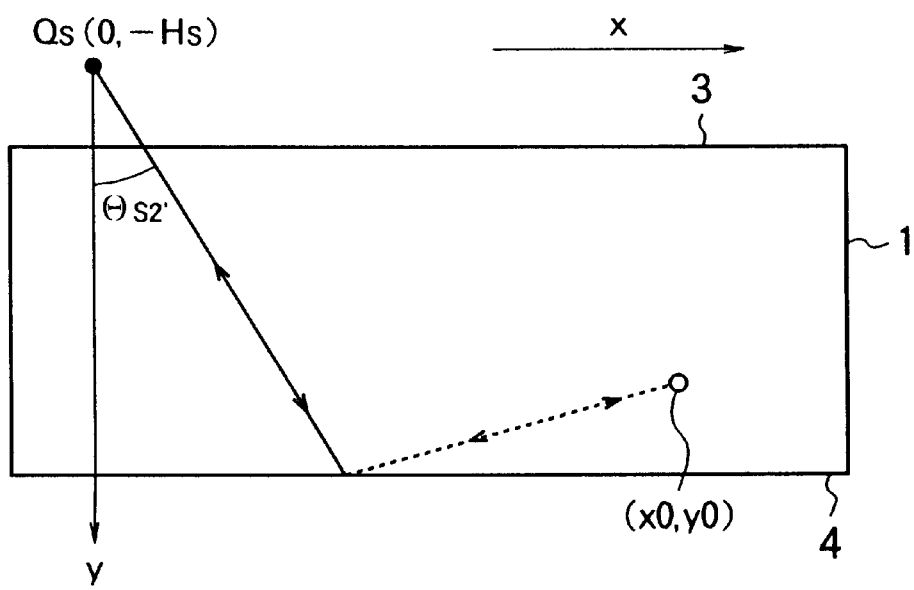
FIG. 47 is a diagram showing a propagation path of an ultrasonic beam for describing the operation of the ultrasonic flaw detection apparatus according to the third embodiment of the present invention.

In FIG. 47, a transverse ultrasonic wave transmitted from the probe 7 is reflected once as the longitudinal ultrasonic wave on the bottom 4 and hits the defect 6 as indicated by the dotted line with the arrow. Then it is reflected as a longitudinal ultrasonic wave by the defect 6 as indicated by the dotted line with the arrow. After that, it is reflected once as a transverse ultrasonic wave on the bottom 4 before it reaches the probe 7 to be received as an echo as indicated by the solid line with the arrow.

Figure 48:
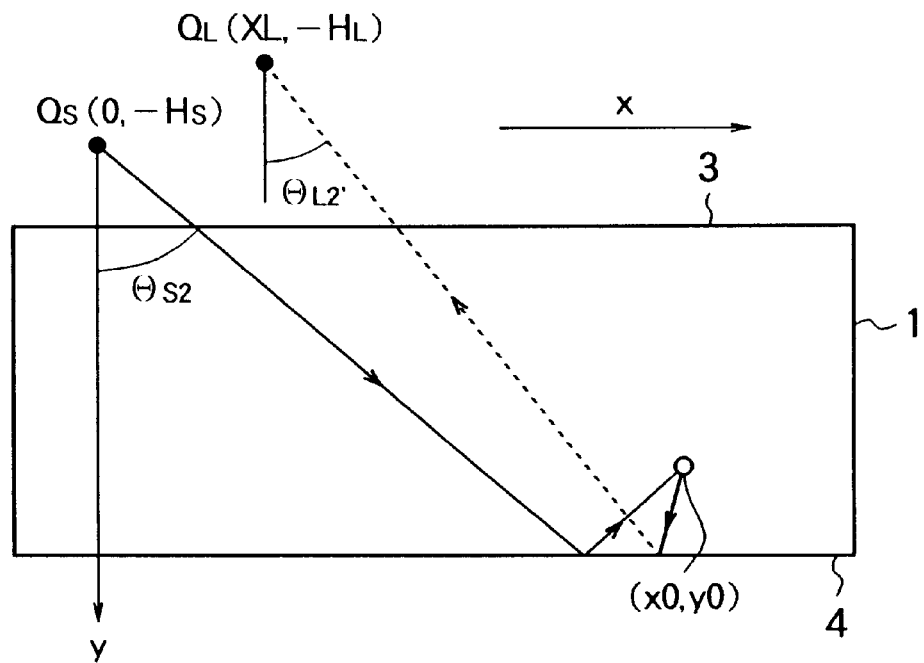
FIG. 48 is a diagram showing a propagation path of an ultrasonic beam for describing the operation of the ultrasonic flaw detection apparatus according to the third embodiment of the present invention.

In FIG. 48, a transverse ultrasonic wave transmitted from the probe 7 is reflected once as the transverse ultrasonic wave on the bottom 4 and hits the defect 6 as indicated by the solid line with the arrow. Then it is reflected as the transverse ultrasonic wave by the defect 6 as indicated by the solid line with the arrow. After that, it is reflected once as a longitudinal ultrasonic wave on the bottom 4 before it reaches the probe 7 to be received as an echo as indicated by the dotted line with the arrow.

Figure 49:
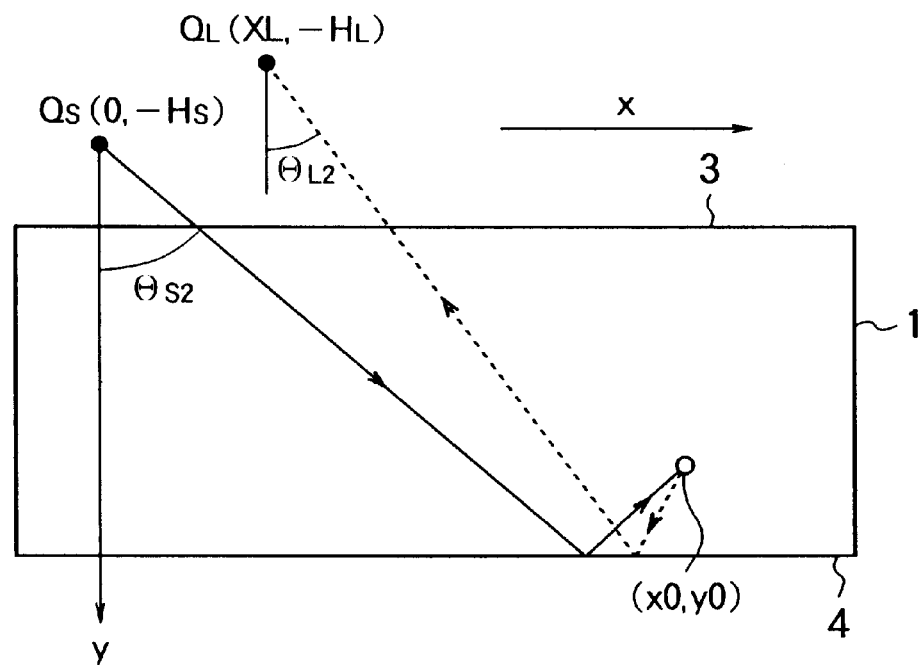
FIG. 49 is a diagram showing a propagation path of an ultrasonic beam for describing the operation of the ultrasonic flaw detection apparatus according to the third embodiment of the present invention.

In FIG. 49, a transverse ultrasonic wave transmitted from the probe 7 is reflected once as the transverse ultrasonic wave on the bottom 4 and hits the defect 6 as indicated by the solid line with the arrow. Then it is reflected as the longitudinal ultrasonic wave by the defect 6 as indicated by the dotted line with the arrow. After that, it is reflected once as a longitudinal ultrasonic wave on the bottom 4 as indicated by the dotted line with the arrow before it reaches the probe 7 to be received as an echo.

Figure 50:
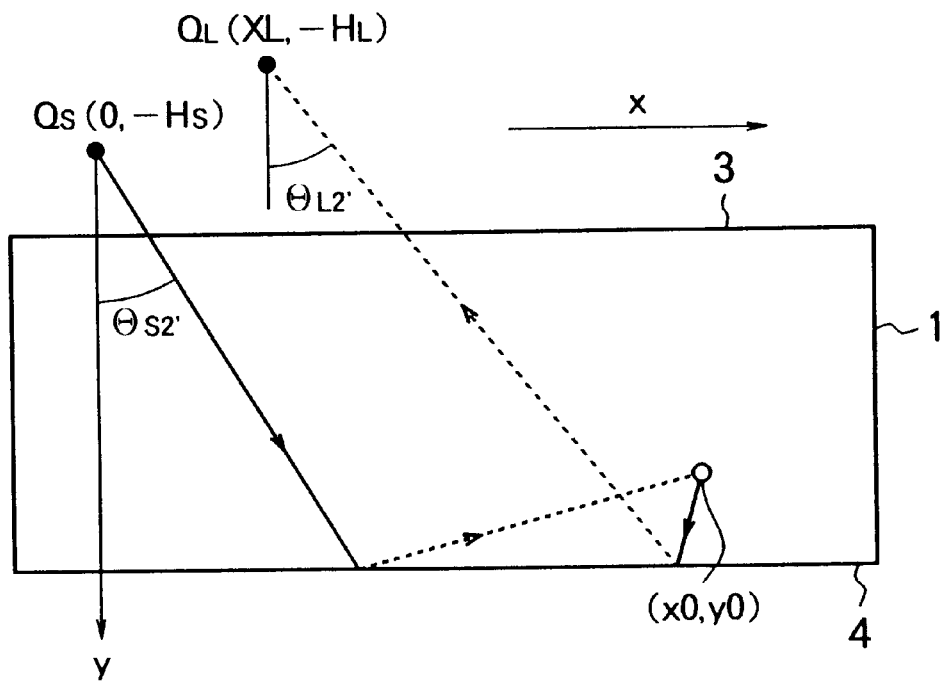
FIG. 50 is a diagram showing a propagation path of an ultrasonic beam for describing the operation of the ultrasonic flaw detection apparatus according to the third embodiment of the present invention.

In FIG. 50, a transverse ultrasonic wave transmitted from the probe 7 is reflected once as the longitudinal ultrasonic wave on the bottom 4 and hits the defect 6 as indicated by the dotted line with the arrow. Then it is reflected as the transverse ultrasonic wave by the defect 6 as indicated by the solid line with the arrow. After that, it is reflected once as a longitudinal ultrasonic wave on the bottom 4 as indicated by the dotted line with the arrow before it reaches the probe 7 to be received as an echo.

Figure 51:
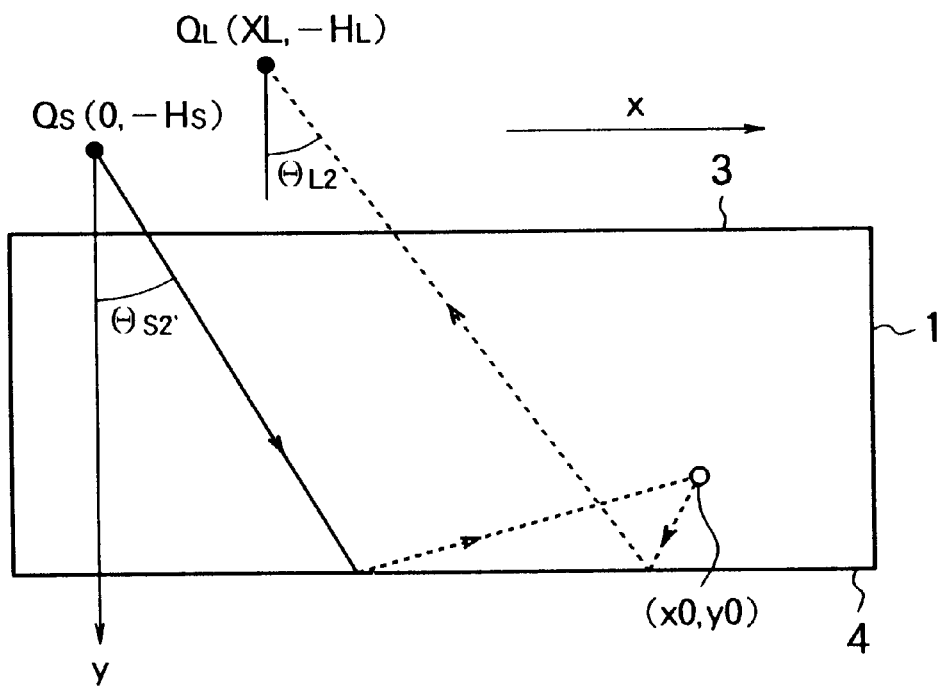
FIG. 51 is a diagram showing a propagation path of an ultrasonic beam for describing the operation of the ultrasonic flaw detection apparatus according to the third embodiment of the present invention.

In FIG. 51, a transverse ultrasonic wave transmitted from the probe 7 is reflected once as the longitudinal ultrasonic wave on the bottom 4 and hits the defect 6 as indicated by the dotted line with the arrow. Then it is reflected as the longitudinal ultrasonic wave by the defect 6 as indicated by the dotted line with the arrow. After that, it is reflected once as a longitudinal ultrasonic wave on the bottom 4 as indicated by the dotted line with the arrow before it reaches the probe 7 to be received as an echo.

In the propagation paths shown in FIG. 48 through FIG. 51, the receiving level is low at the probe 7 since it receives the longitudinal waves which have propagated through the test object 1.

The above discussion refers to the cases where only transverse waves are transmitted from the probe 7 into the test object 1. However, longitudinal waves are also transmitted, although in a smaller scale, from the probe 7 as mentioned above. Therefore, it is possible that the following propagation paths exist in addition to the foregoing beam propagation paths.

A case where $\Theta LL \leq \Theta L1 \leq \Theta LH$ will be discussed. In the following description, the mode shown in the leftmost position indicates the mode of the ultrasonic waves transmitted from the probe 7 into the test object 1, and the mode shown in the second position from the left via an arrow (the mode in the rightmost position) indicates the mode in which the ultrasonic wave is reflected by the defect 6 and directly received by the probe 7.

Longitudinal wave→Longitudinal wave

Longitudinal wave→Transverse wave

The beam paths which are conceivable when $\Theta LL \leq \Theta L1 \leq \Theta LH$ and $\Theta LL \leq \Theta L2 \leq \Theta LH$ will now be shown. In the following description, the mode shown in the leftmost position indicates the mode of the ultrasonic waves transmitted from the probe 7 into the test object 1; the mode shown in the second position from the left via an arrow indicates the mode after the ultrasonic wave, which has been transmitted from the probe 7 into the test object 1, is reflected on the bottom 4; and the mode shown in the third position from the left (the rightmost position) via another arrow indicates the mode in which the ultrasonic wave in the aforesaid mode which has been reflected on the bottom 4 hits the defect 6, and it is reflected by the defect 6 before directly received by the probe 7.

Longitudinal wave→Longitudinal wave→Longitudinal wave

Longitudinal wave→Transverse wave→Longitudinal wave

Longitudinal wave→Longitudinal wave→Transverse wave

Longitudinal wave→Transverse wave→Transverse wave

In addition, the following propagation paths are also conceivable. In the following description, the mode shown in the leftmost position indicates the mode of the ultrasonic waves transmitted from the probe 7 into the test object 1; the mode shown in the second position from the left via an arrow indicates the mode after the ultrasonic wave, which has been transmitted from the probe 7 into the test object 1, is reflected by the defect 6; and the mode shown in the third position from the left (the rightmost position) via another arrow indicates the mode in which the ultrasonic wave in the aforesaid mode which has been reflected by the defect 6 hits the bottom 4 and it is reflected by the bottom 4 before directly received by the probe 7.

Longitudinal wave→Transverse wave→Longitudinal wave

Longitudinal wave→Longitudinal wave→Transverse wave

Longitudinal wave→Transverse wave→Transverse wave

Furthermore, the following propagation paths are also conceivable. In the following description, the mode shown in the leftmost position indicates the mode of the ultrasonic waves transmitted from the probe 7 into the test object 1; the mode shown in the second position from the left via an arrow indicates the mode after the ultrasonic wave, which has been transmitted from the probe 7 into the test object 1, is reflected on the bottom 4; the mode shown in the third position from the left via another arrow indicates the mode after the ultrasonic wave in the aforesaid mode, which has been reflected on the bottom 4, is applied to the defect 6 and reflected by the defect 6; and the mode in the fourth position (the rightmost position) indicates the mode in which the ultrasonic wave in the foregoing mode which has been reflected by the defect 6 is reflected on the bottom 4, then received by the probe 7.

Longitudinal wave→Longitudinal wave→Longitudinal wave→Longitudinal wave

Longitudinal wave→Longitudinal wave→Transverse wave→Longitudinal wave

Longitudinal wave→Transverse wave→Longitudinal wave→Longitudinal wave

Longitudinal wave→Transverse wave→Transverse wave→Longitudinal wave

Longitudinal wave→Longitudinal wave→Longitudinal wave→Transverse wave

Longitudinal wave→Longitudinal wave→Transverse wave→Transverse wave

Longitudinal wave→Transverse wave→Longitudinal wave→Transverse wave

Longitudinal wave→Transverse wave→Transverse wave→Transverse wave

In the above, to make the description easier to understand, the cases where the sound rays up to those corresponding to refraction angle Θ s2 for transverse waves and refraction angle Θ L2 for longitudinal waves exist in the effective ultrasonic beam width have been discussed. Briefly speaking, the cases of beam paths which involve one reflection on the bottom 4 have been discussed.

If the beam width is greater than those discussed above, then more paths which are different from the propagation paths shown above may exist. Specifically, for example, if sound rays up to those corresponding to refraction angle Θ s3 concerning transverse waves and refraction angle Θ L3 concerning longitudinal waves are present in an effective ultrasonic beam width, then it is likely that a propagation path involving a total of two reflections, one reflection on the bottom 4 and one reflection on the surface 3 exists. In this case, there may be also various propagation paths which are established by taking into account the mode conversion from a transverse wave to a longitudinal wave and conversely from a longitudinal wave to a transverse wave at the bottom 4, the surface 3, and the defect 6, respectively.

As the beam width increases, it becomes necessary to consider paths up to those that include two reflections on the bottom 4 and one reflection on the surface 3 and also to consider mode conversion. If the beam width further increases, it is required to consider paths up to those that include two reflections on the bottom 4 and two reflections on the surface 3 and also to consider mode conversion.

Likewise, as the beam width grows greater, the number of reflections on the bottom 4 and the surface 3 increases in regard to the paths to be considered and it becomes necessary to take mode conversion for each reflection into account.

Thus, one of the considerable differences of the third embodiment from the conventional apparatuses and methods is that it provides a method and an apparatus for detecting a flaw at an angle by taking the spread of an ultrasonic beam into account. Further, the third embodiment is entirely different from the prior art disclosed in Japanese Unexamined Patent Publication No. 2-278149, Japanese Unexamined Patent Publication No. 2-248855, or Japanese Unexamined Patent Publication No. 5-172789 in that it also considers the reflections on the surface 3 and the bottom 4. The third embodiment further differs from the prior art in that it takes into account the mode conversion from a transverse wave to a longitudinal wave and the mode conversion from a longitudinal wave to a transverse wave for each reflection at the bottom 4, the surface 3, and the defect 6, respectively.

Based on the consideration results concerning the beam paths discussed above, the signal processing procedure in the signal processor 84B will be described with reference to FIG. 52 and FIG. 53. The coordinate origin in FIG. 52 may be different from those in FIG. 31, and FIG. 35 through FIG. 51. Obviously, the origin may be established anywhere. It is apparent that, if the origin is different from that when the probe 7 performs scanning, then the coordinate conversion must be performed accordingly.

As previously mentioned, the signal processor 84B stores the echo waveforms at respective spatial processor 84B stores the echo waveforms at respective spatial points in the scanning zone when the predetermined scanning zone was scanned with the probe 7 and the information on the spatial positions of the probe 7 at the time when the echo waveforms were received. The echo waveforms are stored as raw waveforms, i.e. AC waveforms which have not been subjected to such processing as rectification or detection.

In step 51 of FIG. 52, a predetermined image reconstruction zone is defined. More specifically, in FIG. 53, a zone wherein an image should be displayed as a result of flaw detection of the test object 1 is defined as indicated, for example, by the dotted line.

In step 52, an image reconstruction point is specified. The image reconstruction point is one point in the foregoing image reconstruction zone. The coordinates of this point are set to (xi, yi) as shown in FIG. 52.

In step 53, the output corresponding to the reconstruction point (xi, yi) is defined as P (xi, yi), and the value is set to zero. More specifically, the value is set so that P (xi, yi)=0.

In step 54, the spatial position, i.e. the coordinates, of the probe 7 and the echo waveform received at that position are selected from the memory. As shown in FIG. 53, the position of the probe 7 is represented by point Qs, and the coordinates are assumed to be (xs, −Hs) when the ultrasonic wave transmitted into the test object 1 is a transverse wave, or when a transverse wave which has propagated through the test object 1 is received by the probe 7. The meaning of point Qs is the same as in FIG. 31. Further, the position of the probe 7 is represented by point QL, and the coordinates are assumed to be (xL, −HL) when the ultrasonic wave transmitted into the test object 1 is a longitudinal wave, or when a longitudinal wave which has propagated through the test object 1 is received by the probe 7. The meaning of point QL is the same as in FIG. 31.

In step 55, a beam propagation path is identified in which, when the image reconstruction point is regarded as the defect 6, an ultrasonic wave is transmitted as a transverse wave from point Qs representing the probe 7 in an effective beam width for transverse wave, i.e. in a zone defined by Θ sL and Θ sH, and the ultrasonic wave reaches the defect 6, then it is reflected by the defect 6 and received as a transverse wave at point Qs representing the probe 7 in the effective beam width for transverse wave, i.e. in a zone defined by e sL and Θ sH.

Another beam propagation path is identified in which an ultrasonic wave is transmitted as a transverse wave from point Qs representing the probe 7 in an effective beam width for transverse wave, i.e. in a zone defined by Θ sL and Θ sH, and the ultrasonic wave reaches the defect 6, then it is reflected by the defect 6 and received as a longitudinal wave at point QL representing the probe 7 in the effective beam width for longitudinal wave, i.e. in a zone defined by Θ LL and Θ LH.

Still another beam propagation path is identified in which an ultrasonic wave is transmitted as a longitudinal wave from point QL representing the probe 7 in an effective beam width for longitudinal wave, i.e. in a zone defined by Θ LL and Θ LH, and the ultrasonic wave reaches the defect 6, then is reflected by the defect 6 and received as a longitudinal wave at point QL representing the probe 7 in the effective beam width for longitudinal wave, i.e. in a zone defined by Θ LL and Θ LH.

Moreover, all possible beam propagation paths are identified in which an ultrasonic wave is transmitted as a longitudinal wave from point QL representing the probe 7 in an effective beam width for longitudinal wave, i.e. in a zone defined by Θ LL and Θ LH, and the ultrasonic wave reaches the defect 6, then is reflected by the defect 6 and received as a transverse wave at point Qs representing the probe 7 in the effective beam width for transverse wave, i.e. in a zone defined by Θ sL and Θ sH.

The foregoing beam propagation paths are identified by taking into account all the mode conversions on the bottom 4 and the surface 3 of the test object 1 and also the mode conversions attributable to the reflection at the defect 6.

FIG. 53 shows only a few examples of the propagation paths because illustrating all the above propagation paths would make the diagram too complicated. There are cases where propagation paths do not exist. In such cases, the program proceeds to step 60. The description of step 60 will be given later.

In step 56, on each of all the beam propagation paths obtained in step 55, the time when the echo is to be received is determined according to the velocity of sound in the test object 1 and the velocity of sound of the transverse wave, and the amplitude of the echo corresponding to the time is called up. The echo means the echo waveform selected in step 54. Next, the amplitudes of the echos called up for the respective beam propagation paths are added, and the result of the addition is added to P (xi, yi).

In step 57, it is determined whether the signal processing from step 54 through step 56 has been completed over the entire scanning zone or a predetermined scanning zone of the probe 7. If the determination result is negative, then the program goes to step 60; if it is affirmative, then the program proceeds to step 58.

In step 58, the value of P (xi, yi) or an absolute value thereof or a square value of the absolute value or the like is output as a reconstructed image at the image reconstruction point (xi, yi).

In step 59, it is determined whether the signal processing from step 52 through step 58 has been completed on all reconstruction points or predetermined reconstruction points in a predetermined image reconstruction zone. If the determination result is negative, then the program goes to step 61; if it is affirmative, then it means that all signal processing in the signal processor 84B has been completed.

In step 60, another spatial position (coordinates) in the scanning zone of the probe 7 is specified, and the signal processing from step 54 to step 57 is continued.

In step 61, another predetermined image reconstruction point in the predetermined image reconstruction zone is specified, and the signal processing from step 52 to step 59 is repeated.

In step 56 of the signal processing shown above, the time when the echo is to be received has been determined for each of all the beam paths, and the amplitude of the echo corresponding to the time has been called up and added. When performing the adding operation, attention needs to be paid to the following.

When an ultrasonic wave is reflected once on the bottom 4, the phase thereof changes. Likewise, the phase also changes when the ultrasonic wave is reflected on the surface 3. Hence, the change of the phase attributable to such reflection must be corrected before adding. The following example will describe a case wherein the phase changes to a reversed phase (180 degrees) due to the reflection.

For instance, it is assumed that there is a path (first path) wherein the transverse ultrasonic pulse transmitted from the probe 7 directly hits the defect 6 and is reflected as a transverse wave by the defect 6, then received directly by the probe 7, a path (second path) wherein the transverse ultrasonic pulse transmitted from the probe 7 directly hits the defect 6 and is reflected as a transverse wave by the defect 6, then reflected once as a transverse wave on the bottom 4 before it is received by the probe 7, and a path (third path) wherein the transverse ultrasonic pulse transmitted from the probe 7 directly hits the defect 6 and is reflected as a transverse wave by the defect 6, reflected once as a transverse wave on the surface 3, then reflected once as a transverse wave on the bottom 4 before it is received by the probe 7.

In this case, in the second path, since the ultrasonic pulse is reflected once on the bottom 4, the phase is shifted 180 degrees in comparison with the first path. In the third path, since the ultrasonic pulse is reflected once on the surface 3 and also once on the bottom 4, the total shift of the phase amounts to 360 degrees in comparison with the first path, meaning that the phase is identical to that in the first path as a result. Hence, the amplitude of the echo corresponding to the first path and the amplitude of the echo corresponding to the third path are added as they are, whereas the value of the amplitude of the echo corresponding to the second path is multiplied by −1 to provide a value obtained by reversing the phase is to be added to the amplitudes which correspond to the first and second paths. The same consideration must be given to the changes in phase attributable to the reflection on the defect 6. Thus, it is required to make the same correction of the changes in phase before adding up the amplitudes of the echos for each of all beam paths.

In step 56 of the signal processing described above, if the amplitude of the echo of the time corresponding to a beam path has a value which is not more than a predetermined signal-to-noise ratio (S/N ratio), then processing with this amplitude taken as zero may, in some cases, reduce the influences by noises on a reconstructed image acquired as a final result. In such a case, only beam paths that have significant corresponding echo amplitudes are selected among all the possible beam paths which have been extracted in step 55, and the amplitudes of echos corresponding thereto are added and the addition result is added to P (xi, yi) to enable a preferable result to be obtained.

The method wherein a refraction angle is selected and a round trip beam propagation path is extracted according to the refraction angle is just one extracting method; other methods are possible. Further, it is not always necessary to identify all round trip beam propagation paths; obtaining several candidates is adequate.

As a result of the signal processing described above, the result of the inspection in the test object 1 has been acquired in terms of an image. The operation and advantage of the third embodiment will now be described.

Unlike the prior art, in the third embodiment, regarding the reflection of an ultrasonic wave on the bottom 4 and the surface 3 of the test object 1, consideration has been given to the mode conversion from a transverse wave to a longitudinal wave or from a longitudinal wave to a transverse wave resulting from reflection and also to the similar mode conversion at the defect 6 in order to obtain candidates of possible ultrasonic beam propagation paths, and the amplitudes of the echos in the time positions which correspond to the ultrasonic beam paths have been added. Further, the result of the addition has been added in relation to the echo corresponding to each position of the probe 7 in the scanning zone of the probe 7. The result of the addition has been output as an image at the image reconstruction point. This makes it possible to reproduce an image with consideration given to the propagation paths which were not considered in the past, thus providing an operation and advantage in that more accurate examination result can be obtained than that available with prior arts.

If the amplitude of the echo in the time position corresponding to the possible ultrasonic beam propagation path has a value which is not more than a predetermined signal-to-noise ratio, then only ultrasonic beam paths that have significant corresponding echo amplitude values are selected among the foregoing ultrasonic beam propagation paths, and only the amplitudes of echos corresponding thereto are added and the addition result is added to P (xi, yi), thus providing an operation and advantage in that sharper images can be obtained and therefore more accurate examination can be achieved.

Furthermore, if a beam width of −3 dB is used for the transmitted ultrasonic beam and the received ultrasonic beam, respectively, as the ultrasonic beam width specified by $\Theta$ sL and $\Theta$ sH concerned with transverse wave, then signal processing based on principal beam can be implemented, thus providing an operation and advantage in that sharper images can be obtained.

Likewise, if a beam width of −3 dB is used for the transmitted ultrasonic beam and the received ultrasonic beam, respectively, as the ultrasonic beam width specified by $\Theta$ LL and $\Theta$ LH concerned with transverse wave, then signal processing based on principal beam can be implemented, thus providing an operation and advantage in that sharper images can be obtained.

The third embodiment described above has referred to a case where an image is reproduced by signal processing by scanning with the probe 7 at a particular value of z on a z-axis perpendicular to the x-axis and the y-axis, i.e. within a section of (x, y) although it is not shown. However, the present invention is not limited thereto, and the information on the defect 6 along the z-axis can be also obtained by implementing the same scanning by using the probe 7 and signal processing along the z-axis, i.e. at diverse values of z, and by reproducing and displaying the final result in terms of a three-dimensional image in the test object 1, thus providing an operation and advantage which allow effective use for classifying, sorting, or the like of the defect 6.

The ultrasonic flaw detection apparatus and the ultrasonic flaw detection method in accordance with the third embodiment of the present invention further present an operation and advantage set forth below. For example, there is such a case as a weld bead wherein it is difficult to transmit and receive ultrasonic waves via the surface of a test object by scanning a probe close to a defect because the surface of the test object is badly uneven. In such a case, if there is a defect near the surface of the test object, then no echo from the defect may be obtained by direct scanning because of the aforesaid limitation on the scanning zone of the probe wherein ultrasonic waves can be transmitted and received properly. Another problem may be encountered: even if there is no such limitation in the scanning zone of the probe on the surface of the test object, the presence of a defect in the vicinity of the surface shortens the required time from the moment a transmission signal is sent to the moment the echo is received, whereas the transmission signal leaks into a receiving circuit, i.e. the receiver, so that the echo is buried in the leakage of the transmission signal, thus preventing the echo from being received properly. In this case, it is necessary to place the probe on the bottom of the test object to use the bottom as the test surface to carry out the flaw detecting examination. If, however, the test object is a part of a structure and the bottom cannot be accessed physically, then it is impossible to use the bottom as the test surface. Even in these cases where the scanning zone of the probe is limited because of the presence of a defect near the surface or where there is the problem of the leakage of a transmission signal, the ultrasonic flaw detection apparatus and the ultrasonic flaw detection method according to the present invention allow the foregoing limitation to be overcome, the foregoing problem to be solved, and the flaw detecting examination to be achieved since they employ the reflection of ultrasonic waves on a bottom and the reflection of ultrasonic waves on a surface as well in addition to direct scanning.

So far, the description has been given to the cases where the probe is brought in direct contact with the test surface of the test object to carry out the flaw detecting examination; the present invention, however, is not limited thereto. It may be applied to a so-called immersion method or immersion testing in which a test object is immersed in a liquid such as water, and the probe transmits and receives ultrasonic waves to and from the test object via the liquid. Or, the present invention may also be applied to a so-called local immersion testing wherein a water film is provided only on an acoustic transmitting and receiving surface which is the front surface of the probe, that is, only in the local space between the probe and the test surface of the test object, and ultrasonic waves are transmitted to and received from the test object. The same operations and advantages of the present invention described above can be obtained also in such immersion method, immersion testing, and local immersion testing.

In conjunction with FIG. 30, it has been described that the scanner 9 has the function for the spacial scanning of the probe 7, outputs the information on the spacial position of the probe 7, and supplies it to the position detector 85. However, the function for gathering and outputting the information on the spatial position of the probe 7 may be implemented by a position information generator provided independently of the scanner 9, that is, the information may be gathered and output by the position information generator, then supplied to the position detector 85. In this case, the scanner 9 is responsible only for the function for the spatial scanning of the probe 7. Further in this case, it is necessary to connect the position information generator to the controller 81 to exchange various types of signals with the controller 81.

Furthermore, in conjunction with FIG. 30, it has been described that the information on the spacial position of the probe 7 is output from the scanner 9 and applied to the position detector 85. However, since the information on the spatial scanning zone and the travel distance of the probe 7 is controlled and generated by the controller 81, the scanner 9 may be responsible only for the spacial scanning function, and the information on the scanning of the probe 7 from the controller 81 may be directly supplied to and stored in the signal processor 84B so as to obviate the need for providing the position detector 85.

Fourth Embodiment

Figure 54:
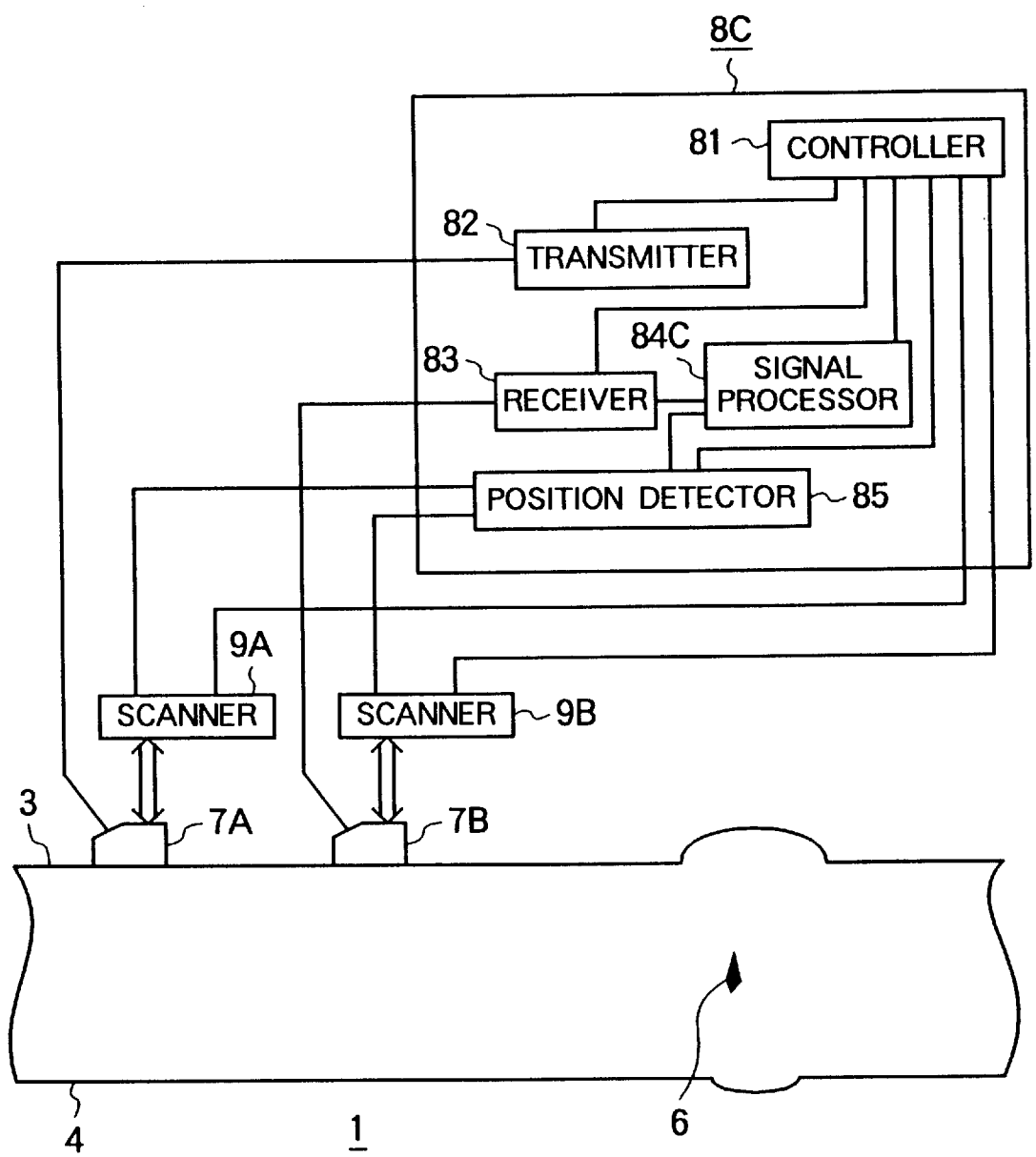
FIG. 54 is a diagram showing the configuration of an ultrasonic flaw detection apparatus according to a fourth embodiment of the present invention.
Figure 55:
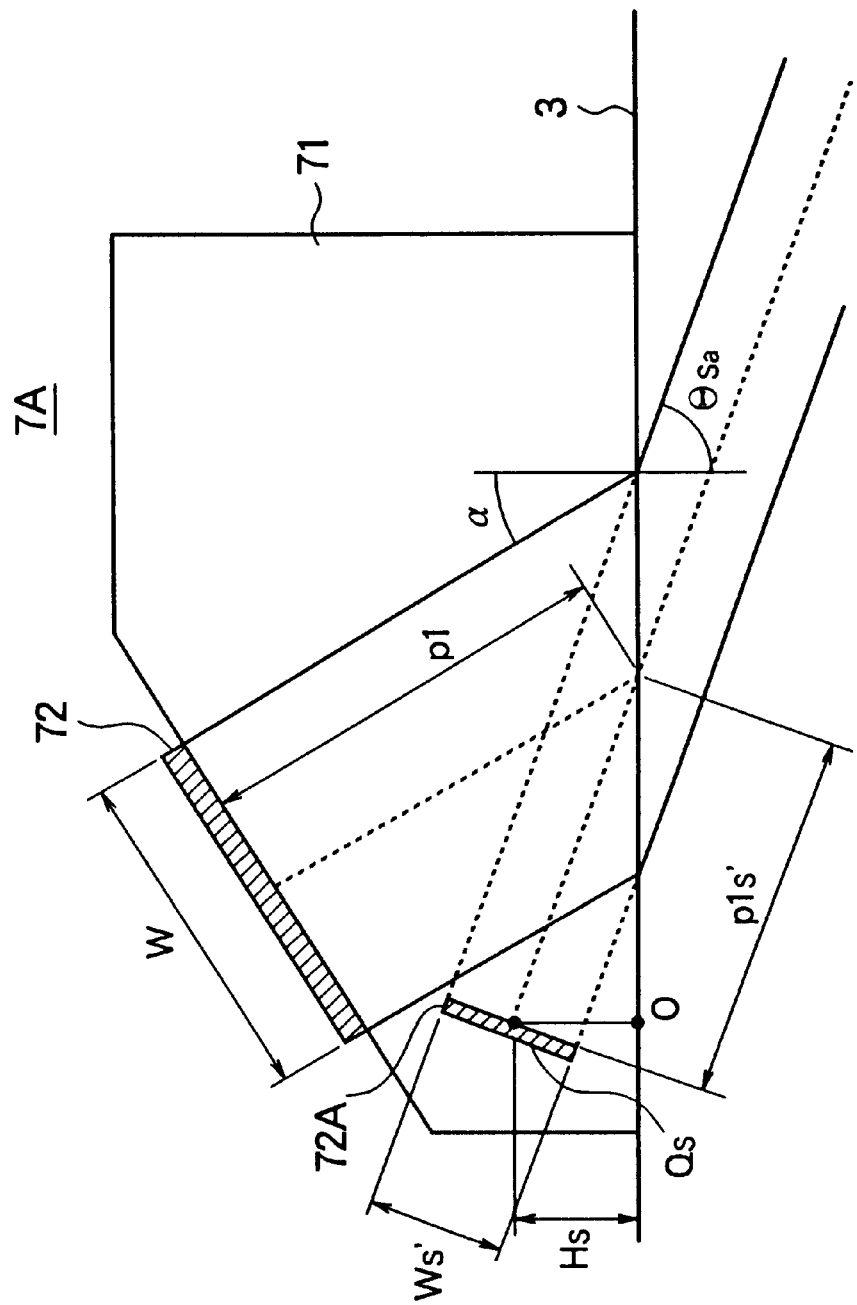
FIG. 55 is a diagram showing the configuration of a probe of the ultrasonic flaw detection apparatus according to the fourth embodiment of the present invention.

Referring to FIG. 54 and FIG. 55, the configuration of an ultrasonic flaw detection apparatus in accordance with a fourth embodiment will be described. FIG. 54 is a block diagram showing the configuration of the ultrasonic flaw detection apparatus according to the fourth embodiment of the present invention. FIG. 55 is a diagram illustrative of the configuration of the probe of the ultrasonic flaw detection apparatus according to the fourth embodiment of the invention. FIG. 55 presents a citation from literature B.

In FIG. 54, the ultrasonic flaw detection apparatus is equipped with: a transmitting probe 7A and a receiving probe 7B rested on a test object 1; a transmitter-receiver 8C connected to probes 7A and 7B; and scanners 9A and 9B for the transmitting probe 7A and the receiving probe 7B.

In the drawing, the transmitter-receiver 8C includes a controller 81, a transmitter 82, a receiver 83, a signal processor 84C, and a position detector 85 for detecting the positions of probes 7A and 7B. The scanners 9A and 9B include sensors for detecting the positions of the transmitting probe 7A and the receiving probe 7B.

In the drawing, the transmitting probe 7A and the receiving probe 7B are connected to the transmitter 82 and the receiver 83 by a signal conductor. The receiver 83 is connected to the signal processor 84C. The position detector 85 is connected to the signal processor 84C. The controller 81 is connected to the transmitter 82, the receiver 83, the signal processor 84C, the position detector 85, and the scanners 9A and 9B.

Further in the drawing, the scanners 9A and 9B are connected to the position detector 85. The output signals from the position detecting sensors of the scanners 9A and 9B are supplied to the position detector 85. The information on the positions of the probe 7A and the probe 7B detected by the position detector 85 is supplied to the signal processor 84C.

The signal processor 84C has an internal memory (not shown). Various results obtained by operations and calculations are stored in this memory in the signal processor 84C as necessary, and the input signals supplied to the signal processor 84C are also stored therein as necessary.

Furthermore, although not shown, the signal processor 84C furnishes signals which indicate processing states to the controller 81 as necessary. Based on the input signals, the controller 81 issues control signals to the transmitter 82, the receiver 83, the signal processor 84C, the position detector 85, and the scanners 9A and 9B to control them.

In FIG. 55, the transmitting probe 7A includes a wedge 71 composed of a material such as acrylic material, and a rectangular or circular transducer 72 composed of a piezoelectric material such as piezoelectric ceramic. The receiving probe 7B shares the same configuration with the transmitting probe 7A shown in FIG. 55.

The operation of the probe 7A (7B) will be described. In the ultrasonic angle beam flaw detection, transverse waves are employed as an extensively used mode of the ultrasonic waves transmitted from the probe 7A into the test object 1. The probe 7A exclusively designed for transverse waves transmits longitudinal ultrasonic waves from the transducer 72 into the wedge 71. It is designed so that the longitudinal ultrasonic waves transmitted into the wedge 71 are reflected and refracted on the boundary surface between the wedge 71 and the test object 1, namely, the surface 3 of the test object 1, according to the Snell's law of reflection and refraction. Therefore, only transverse ultrasonic waves are refracted and propagated into the test object 1. Specifically, the probe 7A is designed to have an incident angle "α" so that the longitudinal waves transmitted from the transducer 72 to the wedge 71 are refracted on the aforesaid boundary surface between the wedge 71 and the test object 1 according to the Snell's law of reflection and refraction and are not launched into the test object 1, only refracted transverse waves being allowed to be launched therein. The transverse ultrasonic waves which have propagated through the test object 1 are received in the reverse order from that described above; therefore, the probe 7A which has been designed specifically for transverse waves receives, design-wise, only the transverse ultrasonic waves which have propagated through the test object 1.

The operation of the probe 7A dedicated for transverse waves thus designed can be easily understood in the following way. In FIG. 55, reference numeral 72A denotes an apparent transducer; and "Hs" denotes the height from the surface 3 of the test object 1 to the center of the apparent transducer 72A. Further, "W" denotes the width of the transducer 72, "Ws'" denotes the width of the apparent transducer 72A, "p1" denotes the distance in the wedge, "p1s'" denotes the distance in the apparent wedge, "α" denotes the incident angle of an ultrasonic wave on the boundary surface between the wedge 71 and the surface 3 of the test object 1, and "θ s" denotes a transverse wave refraction angle.

For the purpose of descriptive convenience, the reference numerals and designations used in this specification (the fourth embodiment) are different from those used in literature B. The correspondence between this specification and literature B is as follows: the designations and reference numerals on the left side of an arrow (→) are those in literature B, while those on the right side thereof are used in the present specification. The height corresponding to that denoted by reference character H in the present specification is not contained in literature B. The position of origin 0 is different from that shown in literature B; it is defined as a point obtained by projecting the center of the apparent transducer 72A perpendicularly to the surface 3 of the test object 1 as shown in FIG. 55.

Height H of the transducer→Width W of the transducer 72

Apparent height HR of the transducer→Apparent width Ws' of the transducer 72

Distance l 1 in the wedge→Distance p1 in the wedge

Distance l 2 in the wedge converted to the distance in the test object→Apparent distance p1s' in the wedge The expression "apparent" has been used as shown above; this is because, as described in literature B, a longitudinal ultrasonic wave transmitted from the transducer 72 into the wedge 71 is refracted according to the Snell's law of refraction at the boundary surface with respect to the test object 1, namely, the surface 3. Therefore, width W of the transducer 72 observed from the test object 1 seemingly becomes Ws' equivalently, and distance pl in the wedge seemingly becomes p1s' equivalently when it is converted to the distance in the test object 1. Employing these apparent physical quantities enables various types of calculations and signal processing to be accomplished by handling the wedge 71 as if it were the test object 1. Thus, the following description will use the apparent transducer 72A, width Ws' thereof, apparent distance P1s' in the wedge, and height Hs related to the center of the apparent transducer 72A. In addition, point Qs is defined as the center of the apparent transducer 72A. The coordinates of point Qs are (0, −Hs).

Because width W of the transducer 72 of the probe 7A is finite, there are refracted longitudinal waves, although in a smaller scale than refracted transverse waves, also in the probe 7A which has been designed as the probe specifically designed for transverse waves extensively used for ultrasonic angle beam flaw detection. In other words, refracted longitudinal waves are transmitted, although in a small scale, into the test object 1. The reverse order from the aforesaid order is followed for receiving. Therefore, even the probe 7A designed exclusively for transverse waves undesirably receives the longitudinal waves which have propagated through the test object 1 although at a lower receiving level than the transverse waves which have propagated through the test object 1. Thus, the longitudinal waves are transmitted from the probe 7A into the test object 1, and the longitudinal waves which have propagated through the test object 1 are inevitably received by the probe 7A; regarding these transmitted longitudinal waves and received longitudinal waves, our (the inventors') experiments have revealed that the concept of the apparent distance in the wedge and the apparent transducer may reasonably be applied just as in the case of the transverse waves. Hence, the center of the apparent transducer with respect to longitudinal waves is denoted as point QL although it is not shown. The coordinates of point QL are generally different from those of point Qs for transverse waves. The coordinates of point QL are represented as (xL, −HL).

Refraction angle θ sa related to the transmitting probe 7A may be identical to or different from refraction angle θ sb which is related to the receiving probe 7B; if they are different, the capability for detecting the defect 6 can be further improved in some cases.

Referring now to FIG. 56 through FIG. 79, the operation of the ultrasonic flaw detection apparatus according to the fourth embodiment of the present invention will be described.

Figure 56:
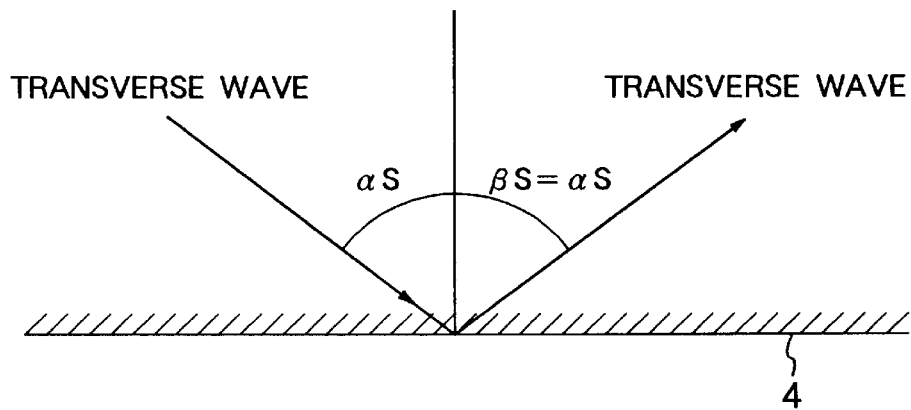
FIG. 56 is a diagram showing a propagation path of an ultrasonic beam for describing the operation of the ultrasonic flaw detection apparatus according to the fourth embodiment of the present invention.
Figure 57:
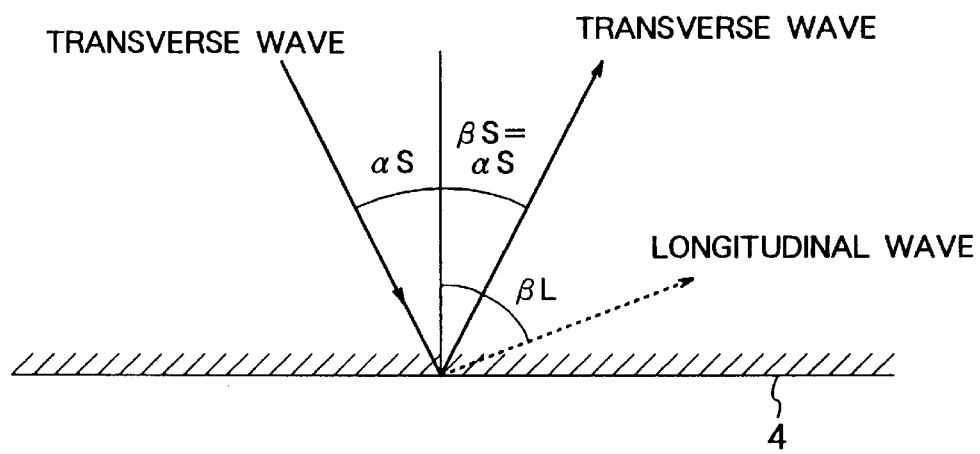
FIG. 57 is a diagram showing a propagation path of an ultrasonic beam for describing the operation of the ultrasonic flaw detection apparatus according to the fourth embodiment of the present invention.
Figure 58:
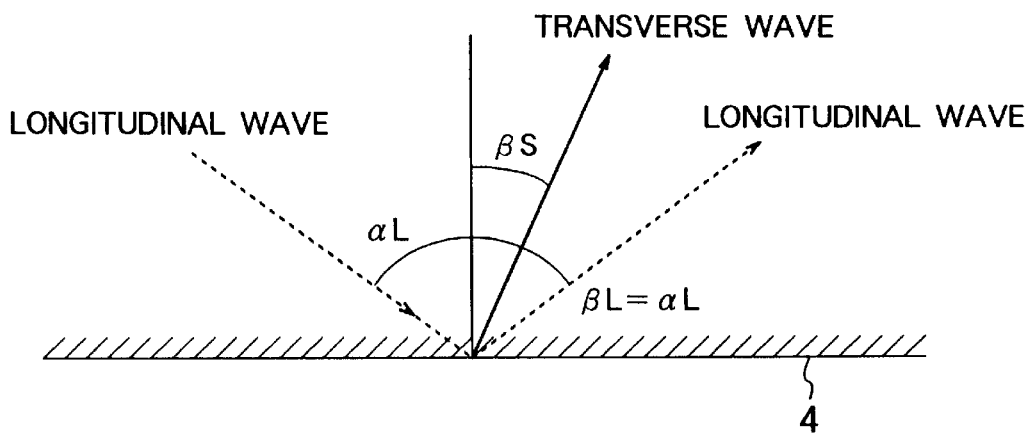
FIG. 58 is a diagram showing a propagation path of an ultrasonic beam for describing the operation of the ultrasonic flaw detection apparatus according to the fourth embodiment of the present invention.

FIG. 56, FIG. 57, and FIG. 58 are diagrams for describing the characteristics concerning the reflection of ultrasonic waves on the boundary surface between a test object and air. FIG. 59 through FIG. 74 are diagrams illustrating the ultrasonic beam propagation paths for describing the operation of the ultrasonic flaw detection apparatus according to the fourth embodiment. FIG. 75 is a flowchart for describing the signal processing of the ultrasonic flaw detection apparatus according to the fourth embodiment. Further, FIG. 76 through FIG. 79 are diagrams illustrating the beam propagation paths for describing the flowchart of the signal processing shown in FIG. 75.

A transmission signal such as a burst signal which has a certain carrier frequency or a narrow pulse which may be regarded as an impulse is generated and transmitted from a transmitter 82 of a transmitter-receiver 8C to the transmitting probe 7A. The transmitting probe 7A is driven by the transmission signal; it transmits the ultrasonic pulse at an angle with respect to the test surface of a test object 1, namely, a surface 3 of the test object 1. The ultrasonic pulse propagates in the test object 1 and it is reflected, scattered, and diffracted by a defect 6. The term "reflection" herein is handled as a term which includes such physical phenomena as scattering and diffraction in addition to reflection. This means that the term "reflection" should be interpreted as a term which includes all phenomena wherein ultrasonic waves are affected by the defect 6 and therefore behave differently in propagation from a case where no defect 6 exists. The description will be given, assuming that a distal end diffraction echo or a tip echo which is known to occur at a tip of the defect 6 is also included in the echos reflected by the defect 6. The reflected, scattered and diffracted ultrasonic pulse propagates through the test object 1 and it is received by the receiving probe 7B. The received echo is amplified by a receiver 83 before it is sent to a signal processor 84C.

The information on the spatial position of the transmitting probe 7A and the receiving probe 7B is detected by scanners 9A and 9B and it is sent to a position detector 85. The information on the spatial positions of the transmitting probe 7A and the receiving probe 7B is sent from the position detector 85 to the signal processor 84C.

The signal processor 84C stores the information on the spatial positions of the transmitting probe 7A and the receiving probe 7B and the received echos.

With the transmitting probe 7A and the receiving probe 7B both fixed in certain spatial positions, the operations described above are implemented, and the information on the spatial positions of the transmitting probe 7A and the receiving probe 7B and the information of the echos are stored.

Then, with the transmitting probe 7A fixed in a spatial position, the receiving probe 7B is moved by the scanner 9B to another spacial position. And an ultrasonic pulse is transmitted from the transmitting probe 7A by the transmission signal, and the echo received from the defect 6 and the information on the spatial positions of the transmitting probe 7A and the receiving probe 7B are transmitted to and stored in the signal processor 84C in the same manner as described above. This series of operations including the spacial scanning with the receiving probe 7B is carried out over a predetermined scanning zone of the receiving probe 7B.

Next the transmitting probe 7A is moved by the scanner 9A to another spacial position and fixed in the position. And an ultrasonic pulse is transmitted from the transmitting probe 7A by the transmission signal, and the echo received from the defect 6 and the information on the spacial positions of the transmitting probe 7A and the receiving probe 7B are transmitted to and stored in the signal processor 84C in the same manner as described above. This series of operations is carried out over a predetermined scanning zone of the receiving probe 7B.

This series of operations including the spatial scanning with the transmitting probe 7A and the receiving probe 7B is carried out over the predetermined scanning zones of the transmitting probe 7A and the receiving probe 7B.

Thus, the transmitting probe 7A has been moved over the spatially predetermined scanning zone and at every position of the transmitting probe 7A in the scanning zone, the receiving probe 7B has been moved over the predetermined scanning zone, and the information on the respective spatial positions of the transmitting probe 7A and the receiving probe 7B and the information on the echos in these positions have been stored in the signal processor 84C. After that, the signal processing, which will be discussed later, is carried out in the signal processor 84C.

Before describing the signal processing procedure in the signal processor 84C, the characteristic concerning the reflection of an ultrasonic wave on the boundary surface between the test object 1 and air will be described with reference to FIG. 56, FIG. 57, and FIG. 58. In these drawings, the solid lines with arrows correspond to transverse waves; the directions indicated by the arrows show the directions of propagation. The dotted lines with arrows correspond to longitudinal waves; the directions indicated by the arrows show the directions of propagation. In the description of the fourth embodiment, in order to distinguish longitudinal waves from transverse waves, the transverse waves will be denoted by the solid lines, while the longitudinal waves will be denoted by the dotted lines in all drawings of the fourth embodiment. The directions of propagation will be indicated by the arrows for both longitudinal waves and transverse waves. A bottom 4 of the test object 1 will be cited as an example of the boundary surface between the test object 1 and air. It is needless to say that the characteristics related to the reflection of ultrasonic waves to be discussed below are based on the Snell's law of reflection and refraction.

FIG. 56 and FIG. 57 illustrate the reflection of a transverse wave which is launched aslant to the bottom 4 after having propagated through the test object 1. FIG. 56 is different from FIG. 57 in that the incident angle denoted by a symbol "$\alpha$ s" in FIG. 56 is larger than that in FIG. 57. As shown in FIG. 56, when the incident angle $\alpha$ s of the transverse waves is large, the ultrasonic waves generated by the reflection on the bottom 4 include only transverse waves. If, however, the incident angle $\alpha$ s of the transverse waves becomes smaller than a certain value, then the reflection on the bottom 4 produces both transverse waves and longitudinal waves except when $\alpha$ s is zero, that is, when the waves are launched perpendicularly, as shown in FIG. 57. In FIG. 56 and FIG. 57, the reflection angle of transverse waves which is denoted by a symbol "$\beta$ s" is equal to the incident angle $\alpha$ s. In FIG. 57, the reflection angle of longitudinal waves which is denoted by a symbol "$\beta$ L" is larger than the reflection angle $\beta$ s of transverse waves.

FIG. 58 illustrates the reflection of a longitudinal wave which is launched aslant to the bottom 4 after having propagated through the test object 1. In the drawing, the angle denoted by a symbol "α L" is the incident angle of the longitudinal wave. The angle denoted by a symbol "β L" is the reflection angle of the longitudinal wave; the angle denoted by a symbol "β s" indicates the reflection angle of a transverse wave. When the longitudinal wave is launched aslant on the bottom 4, the reflection thereof on the bottom 4 produces both transverse wave and longitudinal wave regardless of whether the incident angle α L is large or small except when it is zero, that is, when the wave is launched perpendicularly. The reflection angle β L of the longitudinal wave is equal to the incident angle α L of the longitudinal wave. The reflection angle β s of the transverse wave is smaller than the reflection angle β L of the longitudinal wave.

Considering the foregoing characteristics concerned with the reflection of ultrasonic waves which have been described with reference to FIG. 56, FIG. 57, and FIG. 58, the propagation characteristics of the ultrasonic beams in the test object 1 will be described. Firstly, the propagation paths of ultrasonic beams will be discussed with reference to FIG. 59 and FIG. 60. In the drawings, the horizontal direction (the direction parallel to the surface 3 of the test object 1) is taken on the x-axis, while the vertical direction (the direction in the depth of the test object 1) is taken on the y-axis. It is assumed that a point reflection source which corresponds to the defect 6 is located at (x0, y0).

Figure 59:
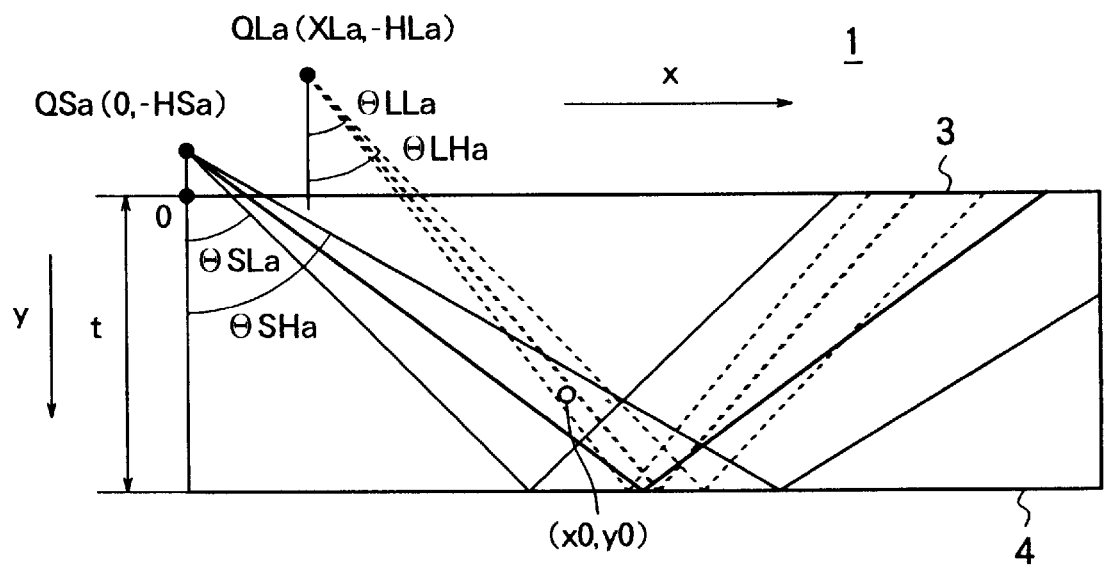
FIG. 59 is a diagram showing a propagation path of an ultrasonic beam for describing the operation of the ultrasonic flaw detection apparatus according to the fourth embodiment of the present invention.

FIG. 59 shows the ultrasonic beam propagation paths related to the ultrasonic beam transmitted from the transmitting probe 7A. In FIG. 59, point Qsa is the center of the apparent transducer 72A associated with the transverse waves of the transmitting probe 7A; the coordinates of the point are defined as (0, −Hsa), where "Hsa" denotes the height from the surface 3 of the test object 1 to the center of the apparent transducer 72A related to the transverse waves of the transmitting probe 7A. In FIG. 59, point QLa denotes the center of the apparent transducer related to the longitudinal waves of the transmitting probe 7A; the coordinates of the point are defined as (xLa, −HLa), where "xLa" denotes the distance between the center of the apparent transducer 72A related to the transverse waves of the transmitting probe 7A and the center of the apparent transducer related to the longitudinal waves in the direction of the x-axis. "HLa" denotes the height from the surface 3 of the test object 1 to the center of the apparent transducer related to the longitudinal waves of the transmitting probe 7A. In the drawing, point QLa representing the center of the apparent transducer related to the longitudinal waves of the transmitting probe 7A is, in practice, located in the vicinity of point Qsa representing the center of the apparent transducer 72A related to the transverse waves of the transmitting probe 7A; however, for easier understanding, these two points QLa and Qsa are drawn far apart from each other in FIG. 59. The same will apply to the following description.

In the description above, reference numeral 72A has been assigned to the apparent transducer related to the transverse waves of the transmitting probe 7A, while no particular reference numeral has been assigned to the apparent transducer related to longitudinal waves. The same will be applied to the following description. Likewise, in the description given below, reference characteristic 72B will be assigned to the apparent transducer related to transverse waves, while no particular reference numeral will be assigned to the apparent transducer related to longitudinal waves.

Referring to FIG. 59, consideration will be given to a case where the ultrasonic wave transmitted from the transmitting probe 7A and launched into the test object 1 is a transverse wave. The transmitted transverse ultrasonic beam transmitted from the apparent transducer 72A related to the transverse waves of the transmitting probe 7A diverges due to diffraction; in the drawing, the thick solid line indicates the centerline of the beam. The thin solid lines indicate the lines which connect the points at which the sound pressure is −3 dB in, for example, from the sound pressure on the centerline in the transmitted transverse ultrasonic beam. In other words, the zone defined by the two thin solid lines corresponds to an effective beam width of the transmitted transverse ultrasonic beam. The refraction angles corresponding to the two thin solid lines are denoted as Θ sLa and Θ sHa as shown in the drawing. In this embodiment, the beam width of −3 dB is used, but it is not limited thereto. Instead may be −6 dB, −9 dB, or −12 dB according to the application or purpose, or other value may be used to define the effective beam width. Further, the propagation mode comes in longitudinal waves and transverse waves; however, the terms "longitudinal ultrasonic waves" and "transverse ultrasonic waves" are employed to mean the ultrasonic waves which propagate in the longitudinal wave mode and the ultrasonic waves which propagate in the transverse wave mode, respectively.

Referring to FIG. 59, consideration will be given to a case where the ultrasonic wave transmitted from the transmitting probe 7A and launched into the test object 1 is a longitudinal wave. The transmitted longitudinal ultrasonic beam sent from the apparent transducer 72A related to the longitudinal waves of the transmitting probe 7A diverges due to diffraction; in FIG. 59, the thick dotted line indicates the centerline of the beam. The thin dotted lines indicate the lines which connect the points at which the sound pressure is −3 dB in, for example, from the sound pressure on the centerline in the transmitted longitudinal ultrasonic beam. In other words, the zone defined by the two thin solid lines corresponds to an effective beam width of the transmitted longitudinal ultrasonic beam. The refraction angles corresponding to the two thin dotted lines are denoted as Θ LLa and Θ LHa as shown in the drawing. These angles respectively correspond to the refraction angles Θ sLa and Θ sHa related to transverse waves. In this case also, the beam width of −3 dB is used, but it is not limited thereto; it may be −6 dB, −9 dB, or −12 dB according to the application or purpose, or other value may be used to define the effective beam width.

Figure 60:
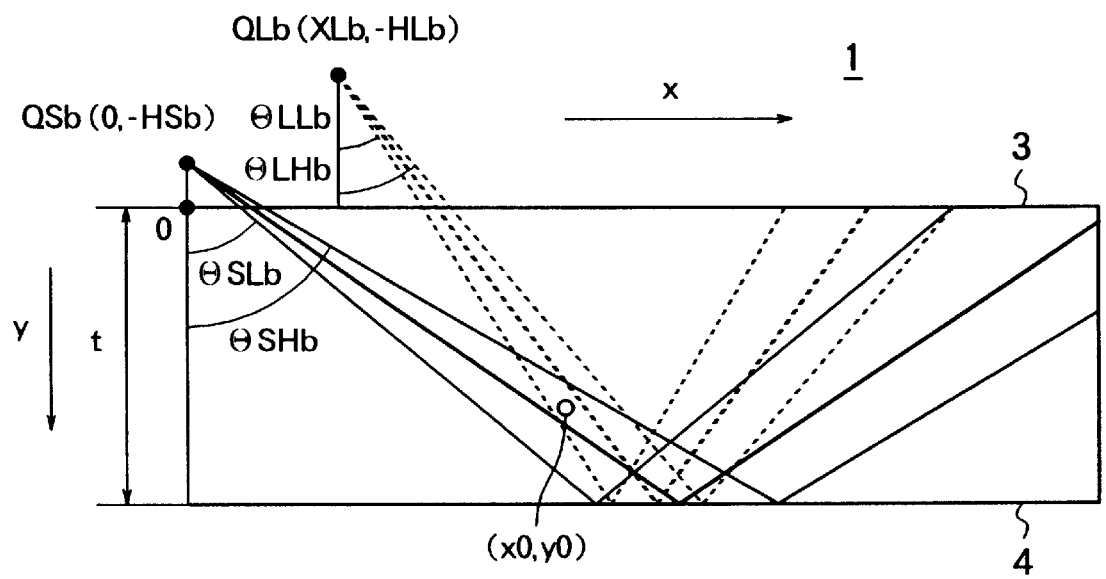
FIG. 60 is a diagram showing a propagation path of an ultrasonic beam for describing the operation of the ultrasonic flaw detection apparatus according to the fourth embodiment of the present invention.

FIG. 60 shows the ultrasonic beam propagation paths related to the ultrasonic beam when receiving ultrasonic waves by the receiving probe 7B. In FIG. 60, point Qsb is the center of the apparent transducer 72B associated with the transverse waves of the receiving probe 7B; the coordinates of the point are defined as (0, −Hsb), where "Hsb" denotes the height from the surface 3 of the test object 1 to the center of the apparent transducer 72B related to the transverse waves of the receiving probe 7B. In FIG. 60, point QLb denotes the center of the apparent transducer related to the longitudinal waves of the receiving probe 7B; the coordinates of the point are defined as (xLb, −HLb), where "xLb" denotes the distance between the center of the apparent transducer 72B related to the transverse waves of the receiving probe 7B and the center of the apparent transducer related to the longitudinal waves in the direction of the x-axis. "HLb" denotes the height from the surface 3 of the test object 1 to the center of the apparent transducer related to the longitudinal waves of the receiving probe 7B. In the drawing, point QLb representing the center of the apparent transducer related to the longitudinal waves of the receiving probe 7B is, in practice, located in the vicinity of point Qsb representing the center of the apparent transducer 72B related to the transverse waves of the receiving probe 7B. However, for easier understanding, these two points QLb and Qsb are drawn far apart from each other in FIG. 60. The same will apply to the following description.

Referring to FIG. 60, consideration will be given first to a case where the ultrasonic wave is a transverse wave when it is received by the receiving probe 7B. The transverse ultrasonic wave received by the apparent transducer 72B related to the transverse waves of the receiving probe 7B is received over a certain diverging angle, taking the diffraction of the ultrasonic wave into account. Therefore, the beam of the received transverse ultrasonic wave diverges over a certain angle range; in the drawing, the thick solid line indicates the centerline of the received transverse ultrasonic beam. The thin solid lines indicate the lines which connect the points at which the sound pressure is −3 dB, for example, from the sound pressure on the centerline in the received transverse ultrasonic beam. In other words, the zone defined by the two thin solid lines corresponds to an effective beam width of the received transverse ultrasonic beam. The refraction angles corresponding to the two thin solid lines are denoted as $\Theta$ sLb and $\Theta$ sHb as shown in the drawing. In this case also, the beam width of −3 dB is used, but it is not limited thereto. Instead may be −6 dB, −9 dB, or −12 dB according to the application or purpose, or other value may be used to define the effective beam width.

Referring to FIG. 60, consideration will now be given to a case where the ultrasonic wave, when it is received by the receiving probe 7B, is a longitudinal wave. The longitudinal ultrasonic beam received by the apparent transducer related to the longitudinal waves of the receiving probe 7B also diverges due to diffraction; in FIG. 60, the thick dotted line indicates the centerline of the beam. The thin dotted lines indicate the lines which connect the points at which the sound pressure is −3 dB, for example, from the sound pressure on the centerline in the received longitudinal ultrasonic beam. In other words, the zone defined by the two thin dotted lines corresponds to an effective beam width of the received longitudinal ultrasonic beam. The angles corresponding to the two thin dotted lines shown in the drawing are denoted as $\Theta$ LLb and $\Theta$ LHb. These angles respectively correspond to refraction angles $\Theta$ sLb and $\Theta$ sHb related to transverse waves. In this case also, the beam width of −3 dB is used, but it is not limited thereto; it may be −6 dB, −9 dB, or −12 dB according to the application or purpose, or other value may be used to define the effective beam width.

Referring now to FIG. 61 through FIG. 74, the sound rays in the transmitted transverse ultrasonic beam width, the transmitted longitudinal ultrasonic beam width, the received transverse ultrasonic beam width, and the received longitudinal ultrasonic beam width will be discussed. In FIG. 61 through FIG. 74, an origin (0, 0) of the coordinates is established at a point where the center of the apparent transducer 72A is projected onto the surface 3 of the test object 1 along the y-axis as in the case of FIG. 59. Point Qsa denotes the center of the apparent transducer 72A related to the transverse waves of the transmitting probe 7A; the coordinates thereof are (0, −Hsa). Point QLa denotes the center of the apparent transducer related to the longitudinal waves of the transmitting probe 7A; the coordinates thereof are (xLa, −HLa). Point Qsb indicates the center of the apparent transducer 72B related to the transverse waves of the receiving probe 7B; the coordinates thereof are (xr, −Hsb). Point QLb indicates the center of the apparent transducer related to the longitudinal waves of the receiving probe 7B; the coordinates thereof are (xr+xLb, −HLb). A blank circle mark located at (x0, y0) denotes a reflection source which corresponds to the defect 6.

Firstly, the description will be given with reference to FIG. 61 through FIG. 64.

Figure 61:
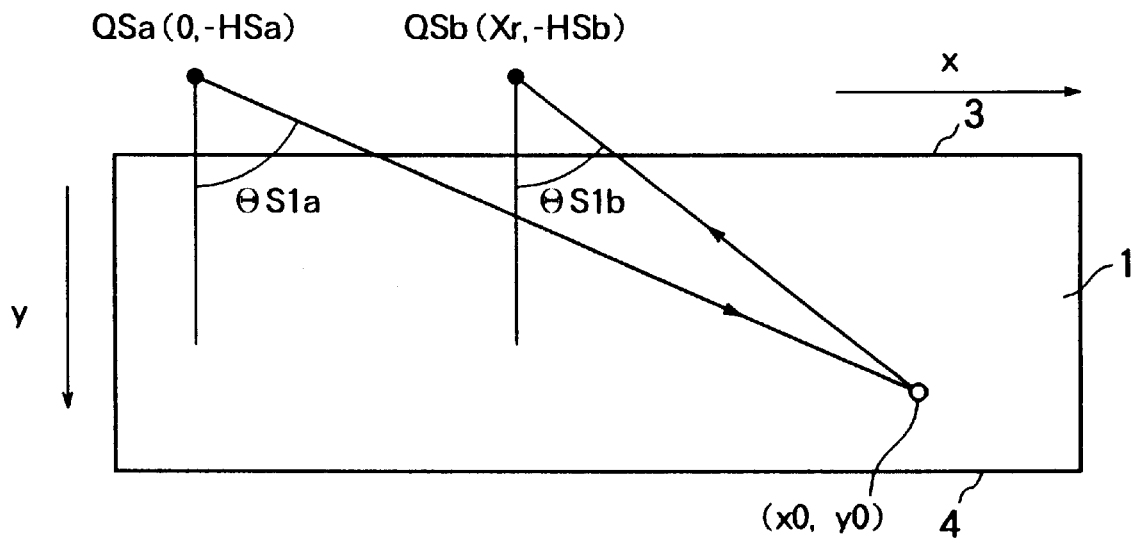
FIG. 61 is a diagram showing a propagation path of an ultrasonic beam for describing the operation of the ultrasonic flaw detection apparatus according to the fourth embodiment of the present invention.

As shown in FIG. 61, if a sound ray equivalent to refraction angle $\Theta$ s1a exists in the effective beam width of the foregoing transmitted transverse ultrasonic beam and a sound ray equivalent to refraction angle $\Theta$ s1b exists in the effective beam width of the foregoing received transverse ultrasonic beam at the same time, that is, if $\Theta$ sLa $\Theta$ s1a$\leq\Theta$ sHa and also $\Theta$ sLb $\Theta$ s1b $\Theta$ sHb at the same time, then the propagation path of the ultrasonic beam indicated by the solid line with arrows in the drawing may exist. At this time, the transverse wave transmitted from the transmitting probe 7A to the test object 1 is directly applied to the defect 6 and directly reflected by the defect 6 as a transverse wave, then received directly by the receiving probe 7B as an echo.

Figure 62:
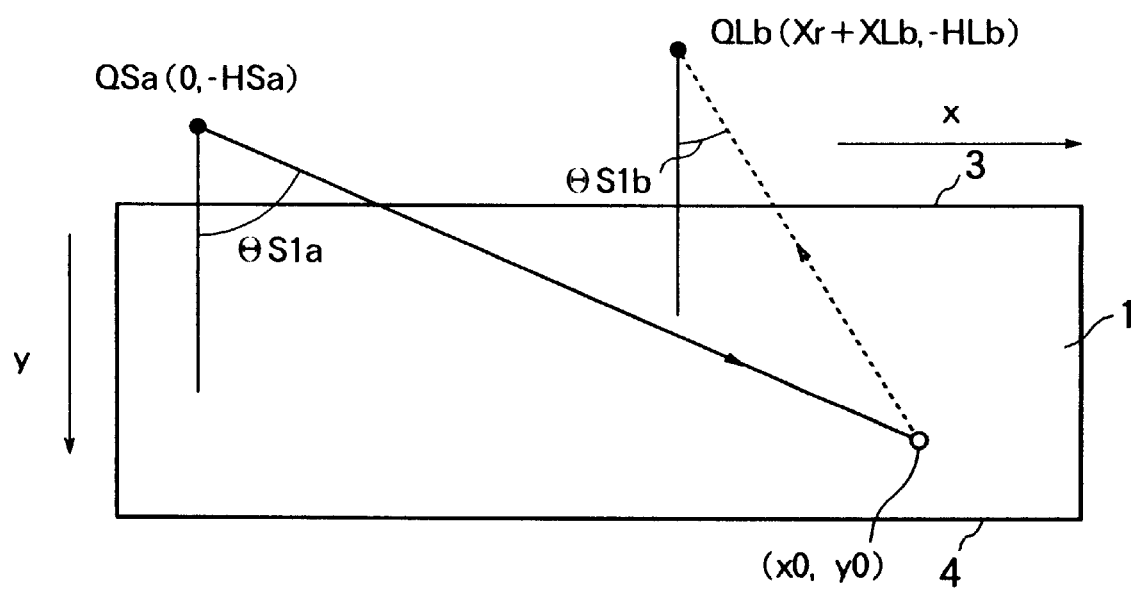
FIG. 62 is a diagram showing a propagation path of an ultrasonic beam for describing the operation of the ultrasonic flaw detection apparatus according to the fourth embodiment of the present invention.

As shown in FIG. 62, if a sound ray equivalent to refraction angle $\Theta$ s1a exists in the effective beam width of the foregoing transmitted transverse ultrasonic beam and a sound ray equivalent to refraction angle $\Theta$ L1b exists in the effective beam width of the foregoing received longitudinal ultrasonic beam at the same time, that is, if $\Theta$ sLa$\leq\Theta$ s1a $\leq\Theta$ sHa and also $\Theta$ LLb $\Theta$ L1b $\Theta$ LHb at the same time, then the propagation path of the ultrasonic wave indicated by the solid line with an arrow and a dotted line with an arrow in the drawing may exist. Specifically, the transverse wave transmitted from the transmitting probe 7A to the test object 1 is directly applied to the defect 6 as shown by the solid line with the arrow in the drawing. The transverse wave directly applied to the defect 6 may develop a component which is mode-converted to a longitudinal wave and reflected as the longitudinal wave, depending on the properties of the defect 6. The reflected longitudinal wave is received directly by the receiving probe 7B as an echo, although in a low level, as indicated by the dotted line with the arrow.

Figure 63:
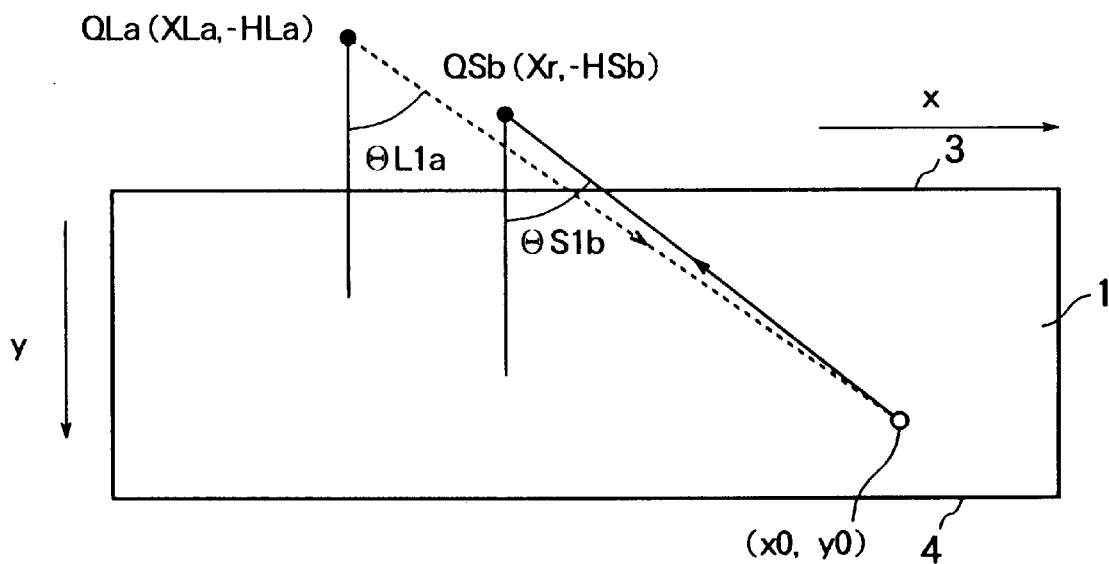
FIG. 63 is a diagram showing a propagation path of an ultrasonic beam for describing the operation of the ultrasonic flaw detection apparatus according to the fourth embodiment of the present invention.

As shown in FIG. 63, if a sound ray equivalent to refraction angle $\Theta$ L1a exists in the effective beam width of the foregoing transmitted longitudinal ultrasonic beam and a sound ray equivalent to refraction angle $\Theta$ s1b exists in the effective beam width of the foregoing received transverse ultrasonic beam at the same time, that is, if $\Theta$ LLa$\leq\Theta$ L1a$\leq\Theta$ LHa and also $\Theta$ sLb$\leq\Theta$ s1b$\leq\Theta$ sHb at the same time, then the propagation path of the ultrasonic wave indicated by a dotted line with an arrow and a solid line with an arrow in the drawing may exist. Specifically, a longitudinal wave is transmitted from the transmitting probe 7A to the test object 1 although at a smaller level than a transverse wave component. The transmitted longitudinal wave is directly applied to the defect 6 as shown by the dotted line with the arrow in the drawing. The longitudinal wave directly applied to the defect 6 may develop a component which is mode-converted to a transverse wave and reflected as the transverse wave, depending on the properties of the defect 6. The reflected transverse wave is received directly by the receiving probe 7B as an echo as indicated by the solid line with the arrow.

Figure 64:
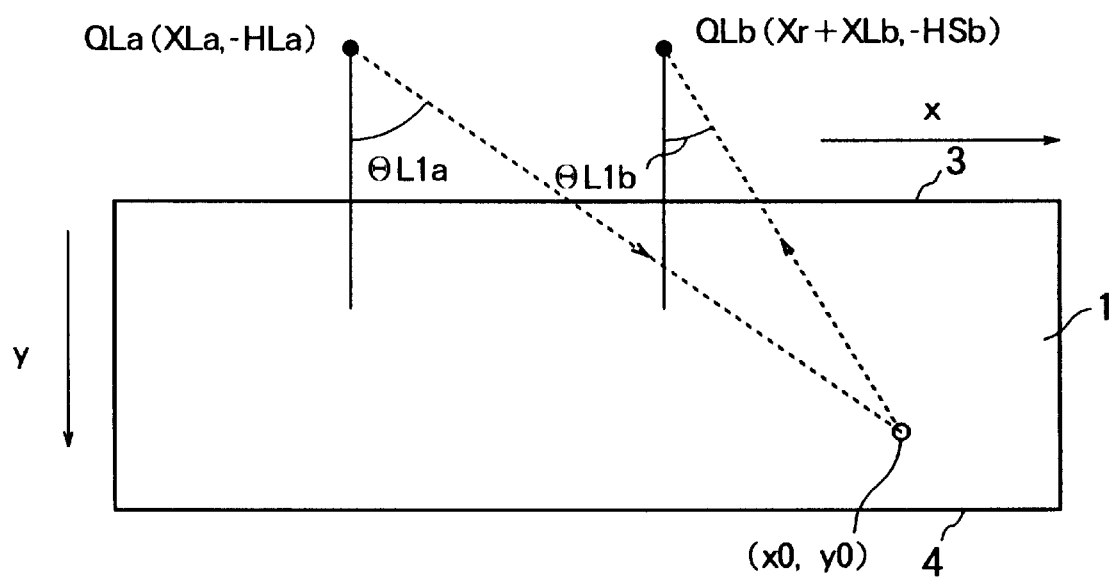
FIG. 64 is a diagram showing a propagation path of an ultrasonic beam for describing the operation of the ultrasonic flaw detection apparatus according to the fourth embodiment of the present invention.

As shown in FIG. 64, if a sound ray equivalent to refraction angle $\Theta$ L1a exists in the effective beam width of the foregoing transmitted longitudinal ultrasonic beam and a sound ray equivalent to refraction angle $\Theta$ L1b exists in the effective beam width of the foregoing received longitudinal ultrasonic beam at the same time, that is, if $\Theta$ LLa$\leq\Theta$ L1a$\leq\Theta$ LHa and also $\Theta$ LLb$\leq\Theta$ L1b$\leq\Theta$ LHb at the same time, then the propagation path of the ultrasonic wave indicated by the dotted lines with arrows in the drawing may exist. Specifically, a longitudinal wave is transmitted from the transmitting probe 7A to the test object 1 although at a smaller level than a transverse wave component. The transmitted longitudinal wave is directly applied to the defect 6 and reflected as a longitudinal wave by the defect 6 before it is received directly by the receiving probe 7B as an echo.

So far, the consideration has been given to the propagation paths wherein the ultrasonic wave transmitted from the transmitting probe 7A to the test object 1 directly hits the defect 6, and the ultrasonic wave reflected by the defect 6 is directly received by the receiving probe 7B.

Referring now to FIG. 65 through FIG. 68, other conceivable propagation paths will be considered.

Figure 65:
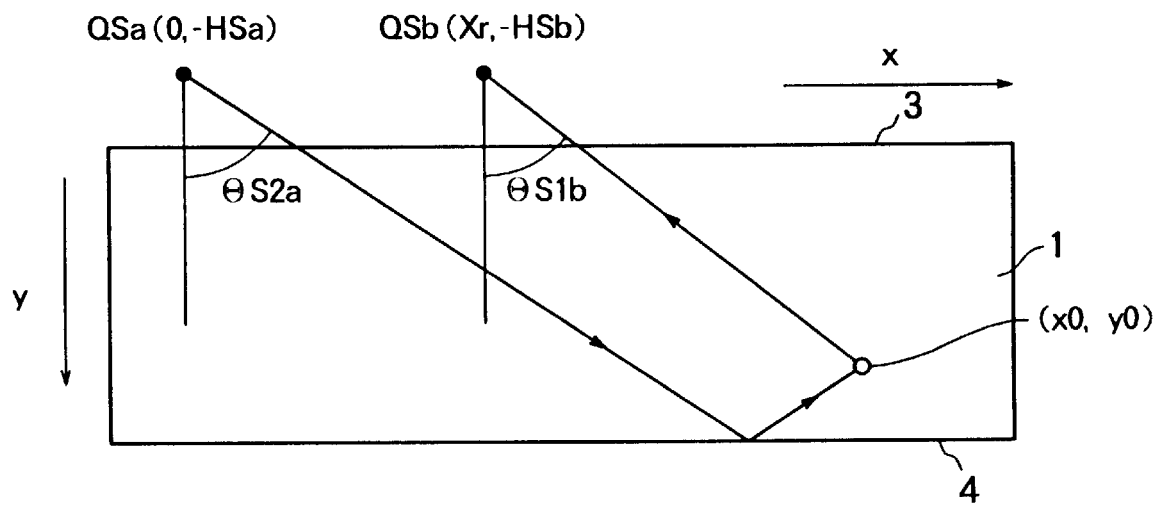
FIG. 65 is a diagram showing a propagation path of an ultrasonic beam for describing the operation of the ultrasonic flaw detection apparatus according to the fourth embodiment of the present invention.

As shown in FIG. 65, if a sound ray equivalent to refraction angle $\Theta$ s2$a$ exists in the effective beam width of the foregoing transmitted transverse ultrasonic beam and a sound ray equivalent to refraction angle $\Theta$ s1$b$ exists in the effective beam width of the foregoing received transverse ultrasonic beam at the same time, that is, if $\Theta$ sLa$\leq\Theta$ s2$a\leq\Theta$ sha and also $\Theta$ sLb$\leq\Theta$ s1$b\leq\Theta$ sHb at the same time, then the propagation path of the ultrasonic wave indicated by the solid lines with arrows in the drawing may exist. Specifically, the transverse ultrasonic wave transmitted from the transmitting probe 7A to the test object 1 is reflected once on the bottom 4 as a transverse ultrasonic wave, then it hits the defect 6 and it is reflected by the defect 6 as a transverse ultrasonic wave before directly reaching the receiving probe 7B to be received as an echo as indicated by the solid lines with arrows.

Figure 66:
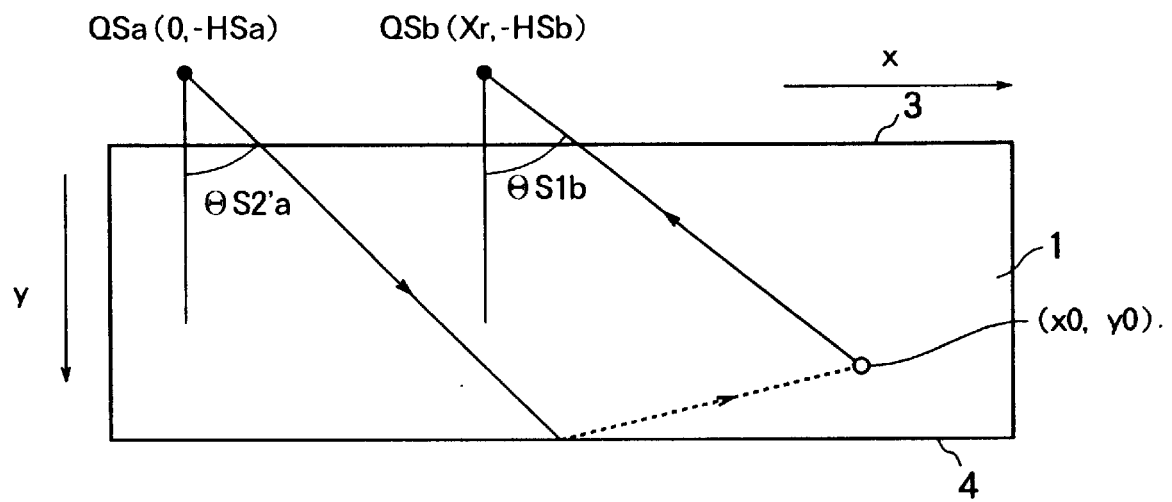
FIG. 66 is a diagram showing a propagation path of an ultrasonic beam for describing the operation of the ultrasonic flaw detection apparatus according to the fourth embodiment of the present invention.

As shown in FIG. 66, if a sound ray equivalent to refraction angle $\Theta$ s2'$a$ exists in the effective beam width of the foregoing transmitted transverse ultrasonic beam and a sound ray equivalent to refraction angle $\Theta$ s1$b$ exists in the effective beam width of the foregoing received transverse ultrasonic beam at the same time, that is, if $\Theta$ sLa$\leq\Theta$ s2'$a\leq\Theta$ sha and also $\Theta$ sLb$\leq\Theta$ s1$b\leq\Theta$ sHb at the same time, then the propagation path of the ultrasonic wave indicated by a solid line with an arrow, a dotted line with an arrow which continues therefrom, and a solid line with an arrow which further follows therefrom in the directions shown by the arrows in the drawing may exist. Specifically, the transverse wave transmitted from the transmitting probe 7A to the test object 1 is propagated toward the bottom 4 as indicated by the solid line with the arrow. After that, as shown by the dotted line with the arrow, the ultrasonic wave is reflected once on the bottom 4 as a longitudinal ultrasonic wave and propagated toward the defect 6. Then, the longitudinal ultrasonic wave hits the defect 6, and it is reflected by the defect 6 as a transverse ultrasonic wave. The reflected transverse ultrasonic wave directly reaches the receiving probe 7B as indicated by the solid line with the arrow and it is received as an echo.

Figure 67:
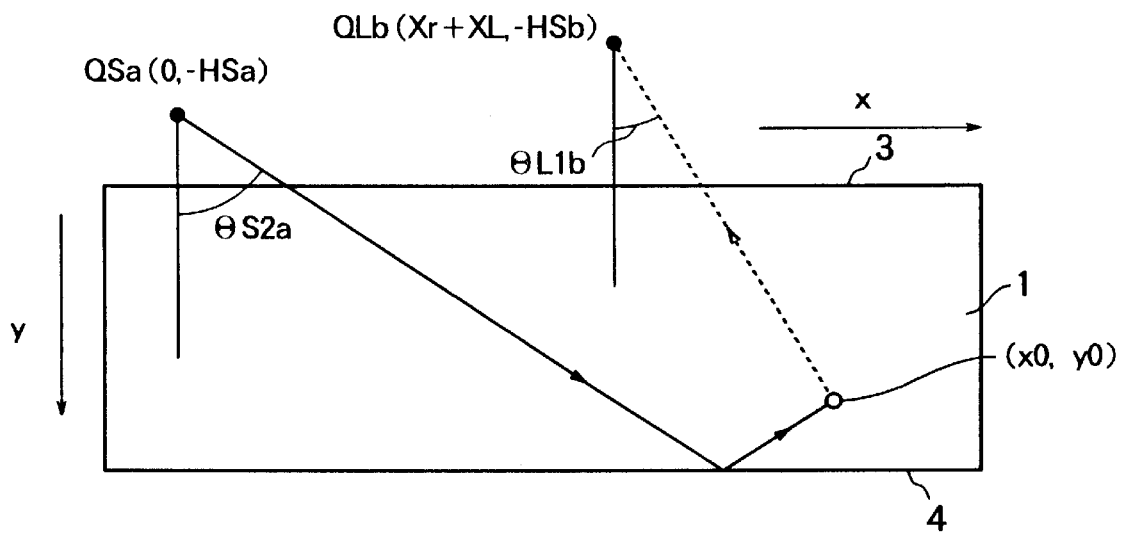
FIG. 67 is a diagram showing a propagation path of an ultrasonic beam for describing the operation of the ultrasonic flaw detection apparatus according to the fourth embodiment of the present invention.

As shown in FIG. 67, if a sound ray equivalent to refraction angle $\Theta$ s2$a$ exists in the effective beam width of the foregoing transmitted transverse ultrasonic beam and a sound ray equivalent to refraction angle $\Theta$ L1$b$ exists in the effective beam width of the foregoing received longitudinal ultrasonic beam at the same time, that is, if $\Theta$ sLa$\leq\Theta$ s2$a\leq\Theta$ sHa and also $\Theta$ LLb$\leq\Theta$ L1$b\leq\Theta$ LHb at the same time, then the propagation path of the ultrasonic wave indicated by a solid line with an arrow and a solid line with an arrow which continues therefrom, and a dotted line with an arrow which further continues therefrom in the directions shown by the arrows in the drawing may exist. Specifically, a transverse ultrasonic wave transmitted from the transmitting probe 7A to the test object 1 propagates toward the bottom 4 as indicated by the solid line with the arrow. After that, as shown by the solid line with the arrow, the ultrasonic wave is reflected once on the bottom 4 as a transverse ultrasonic wave and propagated toward the defect 6. Then, the transverse ultrasonic wave hits the defect 6, and is reflected by the defect 6 as a longitudinal ultrasonic wave. The reflected longitudinal ultrasonic wave directly reaches the receiving probe 7B as indicated by the dotted line with the arrow and it is received as an echo.

Figure 68:
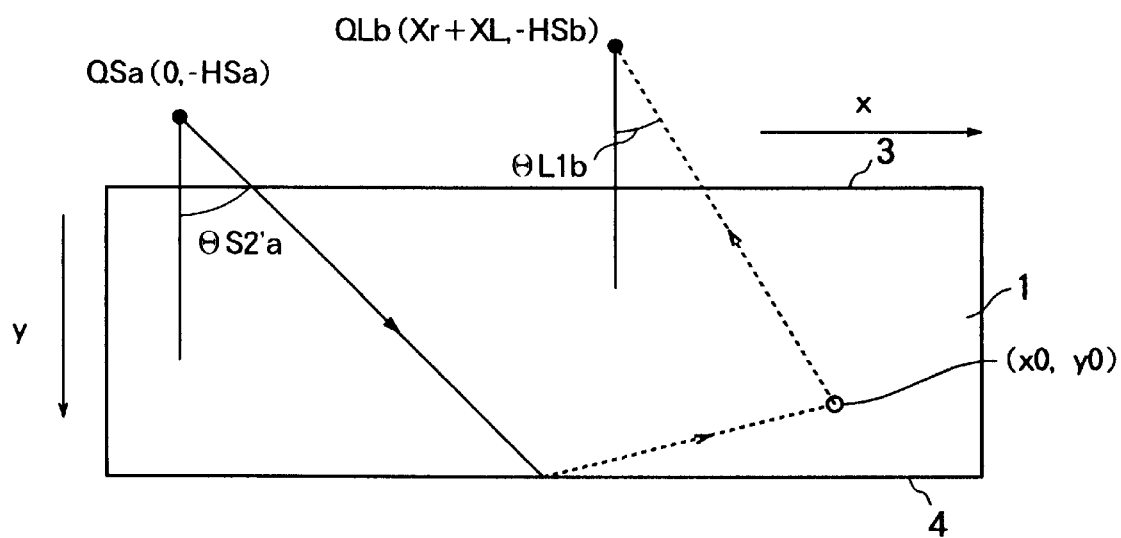
FIG. 68 is a diagram showing a propagation path of an ultrasonic beam for describing the operation of the ultrasonic flaw detection apparatus according to the fourth embodiment of the present invention.

As shown in FIG. 68, if a sound ray equivalent to refraction angle $\Theta$ s2'$a$ exists in the effective beam width of the foregoing transmitted transverse ultrasonic beam and a sound ray equivalent to refraction angle $\Theta$ L1$b$ exists in the effective beam width of the foregoing received longitudinal ultrasonic beam at the same time, that is, if $\Theta$ sLa$\leq\Theta$ s2'$a\leq\Theta$ sHa and also $\Theta$ LLb$\leq\Theta$ L1$b\leq\Theta$ LHb at the same time, then the propagation path of the ultrasonic wave indicated by a solid line with an arrow and a dotted line with an arrow which continues therefrom, and a dotted line with an arrow which further continues therefrom in the directions shown by the arrows in the drawing may exist. Specifically, a transverse ultrasonic wave transmitted from the transmitting probe 7A to the test object 1 propagates toward the bottom 4 as indicated by the solid line with the arrow. After that, as shown by the dotted line with the arrow, the ultrasonic wave is reflected once on the bottom 4 as a longitudinal ultrasonic wave and propagated toward the defect 6. Then, the longitudinal ultrasonic wave hits the defect 6, and is reflected by the defect 6 as a longitudinal ultrasonic wave. The reflected longitudinal ultrasonic wave directly reaches the receiving probe 7B as indicated by the dotted line with the arrow and it is received as an echo.

Thus, the consideration has been given to the cases wherein the ultrasonic waves transmitted from the transmitting probe 7A to the test object 1 are transverse ultrasonic waves, and to the propagation paths wherein the transverse waves are reflected on the bottom 4 of the test object 1 and propagated toward the defect 6, then reflected by the defect 6 before directly reaching the receiving probe 7B. In these cases, the mode conversions at the bottom 4 and the defect 6 have been taken into account.

Referring now to FIG. 69 through FIG. 72, other possible propagation paths will be considered.

Figure 69:
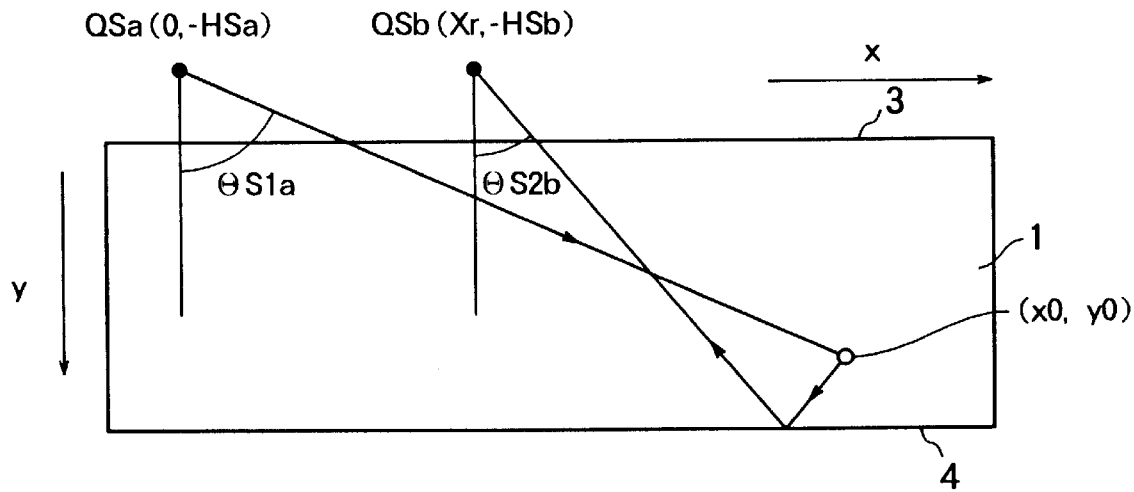
FIG. 69 is a diagram showing a propagation path of an ultrasonic beam for describing the operation of the ultrasonic flaw detection apparatus according to the fourth embodiment of the present invention.

As shown in FIG. 69, if a sound ray equivalent to refraction angle $\Theta$ s1$a$ exists in the effective beam width of the foregoing transmitted transverse ultrasonic beam and a sound ray equivalent to refraction angle $\Theta$ s2$b$ exists in the effective beam width of the foregoing received transverse ultrasonic beam at the same time, that is, if $\Theta$ sLa$\leq\Theta$ s1$a\leq\Theta$ sHa and also $\Theta$ sLb$\leq\Theta$ s2$b\leq\Theta$ sHb at the same time, then the propagation path of the ultrasonic wave indicated by the solid lines with arrows in the drawing may exist. Specifically, the transverse ultrasonic wave transmitted from the transmitting probe 7A to the test object 1 is directly applied to the defect 6, reflected by the defect 6 as a transverse ultrasonic wave, then it is reflected once on the bottom 4 as a transverse ultrasonic wave before reaching the receiving probe 7B to be received as an echo as indicated by the solid lines with arrows.

Figure 70:
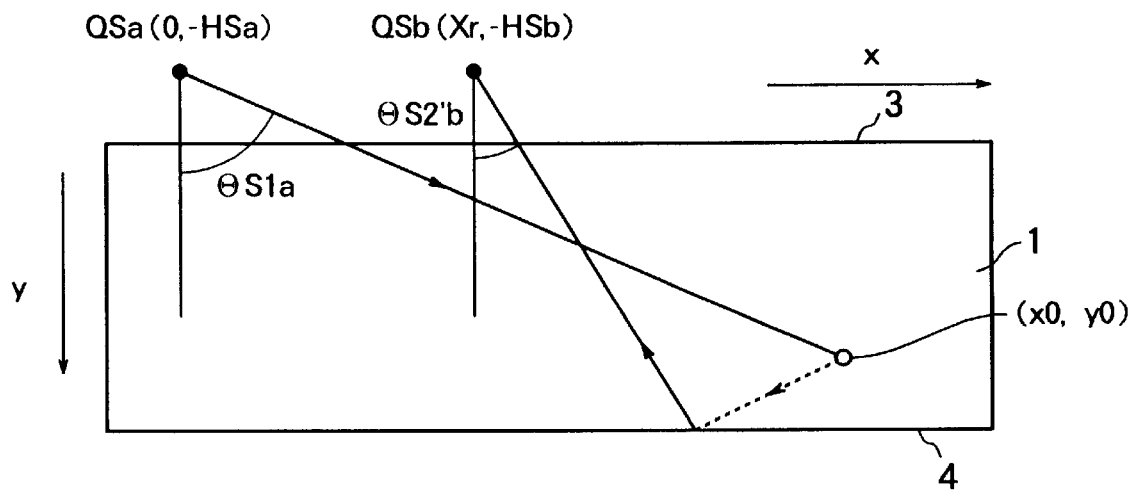
FIG. 70 is a diagram showing a propagation path of an ultrasonic beam for describing the operation of the ultrasonic flaw detection apparatus according to the fourth embodiment of the present invention.

As shown in FIG. 70, if a sound ray equivalent to refraction angle $\Theta$ s1$a$ exists in the effective beam width of the foregoing transmitted transverse ultrasonic beam and a sound ray equivalent to refraction angle $\Theta$ s2'$b$ exists in the effective beam width of the foregoing received transverse ultrasonic beam at the same time, that is, if $\Theta$ sLa$\leq\Theta$ s1$a\leq\Theta$ sHa and also $\Theta$ sLb$\leq\Theta$ s2'$b\leq\Theta$ sHb at the same time, then the propagation path of the ultrasonic wave indicated by a solid line with an arrow, a dotted line with an arrow which continues therefrom, and a solid line with an arrow which further follows therefrom in the directions shown by the arrows in the drawing may exist. Specifically, the transverse ultrasonic wave transmitted from the transmitting probe 7A to the test object 1 is propagated toward the defect 6 as indicated by the solid line with the arrow. After that, the transverse ultrasonic wave directly hits the defect 6, and is reflected by the defect 6 as a longitudinal ultrasonic wave. The reflected longitudinal ultrasonic wave then propagates toward the bottom 4 as shown by the dotted line with the arrow. The longitudinal ultrasonic wave is then reflected once on the bottom 4 as a transverse ultrasonic wave. The reflected transverse ultrasonic wave reaches the receiving probe 7B to be received as an echo as indicated by the solid line with the arrow.

Figure 71:
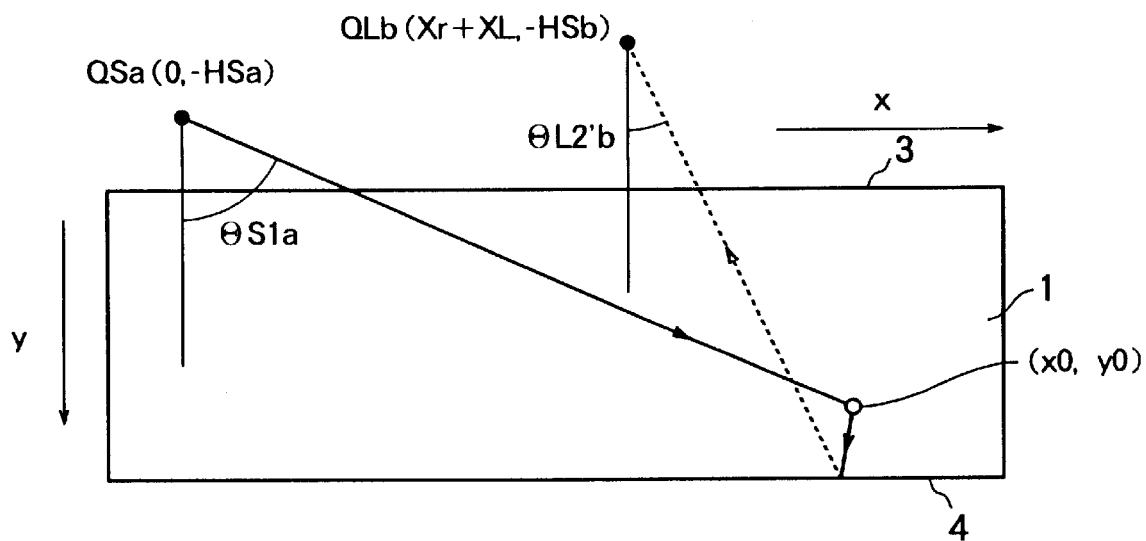
FIG. 71 is a diagram showing a propagation path of an ultrasonic beam for describing the operation of the ultrasonic flaw detection apparatus according to the fourth embodiment of the present invention.

As shown in FIG. 71, if a sound ray equivalent to refraction angle $\Theta$ s1$a$ exists in the effective beam width of the foregoing transmitted transverse ultrasonic beam and a sound ray equivalent to refraction angle $\Theta$ L2'$b$ exists in the effective beam width of the foregoing received longitudinal ultrasonic beam at the same time, that is, if $\Theta$ sL$a \leq \Theta$ s1$a \leq \Theta$ sHa and also $\Theta$ LLb$\leq \Theta$ L2'$b \leq \Theta$ LHb at the same time, then the propagation path of the ultrasonic wave indicated by a solid line with an arrow and a solid line with an arrow which continues therefrom, and a dotted line with an arrow which further continues therefrom in the directions shown by the arrows in the drawing may exist. Specifically, a transverse ultrasonic wave transmitted from the transmitting probe 7A to the test object 1 propagates toward the defect 6 as indicated by the solid line with the arrow. After that, the transverse ultrasonic wave hits the defect 6 and is reflected by the defect 6 as a transverse ultrasonic wave. The reflected transverse then propagates toward the bottom 4 as indicated by the solid line with the arrow. After that, the transverse ultrasonic wave is reflected once on the bottom 4 as a longitudinal ultrasonic wave. The reflected longitudinal ultrasonic wave then reaches the receiving probe 7B as indicated by the dotted line with the arrow and it is received as an echo.

Figure 72:
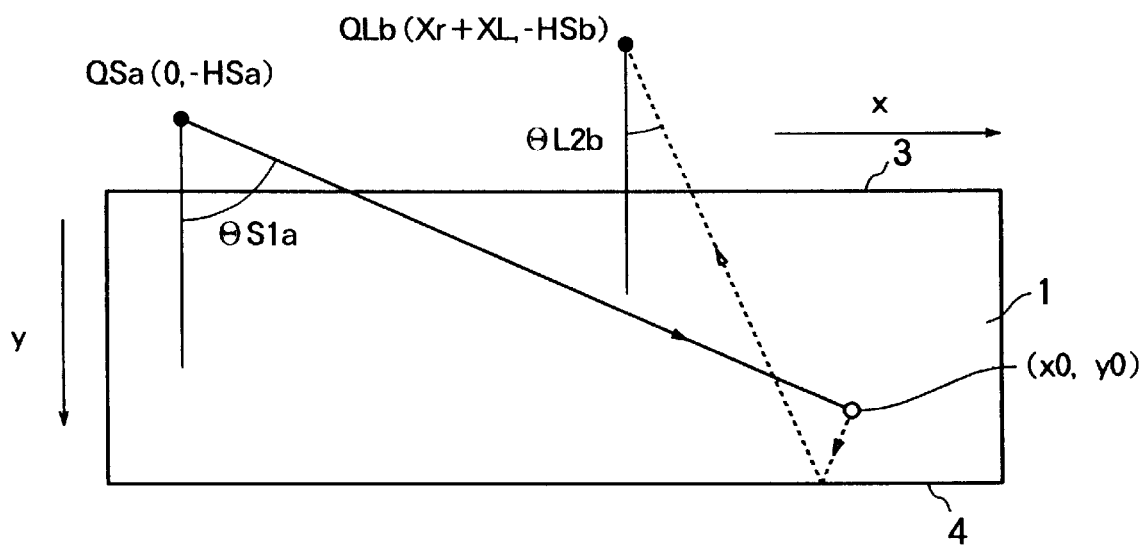
FIG. 72 is a diagram showing a propagation path of an ultrasonic beam for describing the operation of the ultrasonic flaw detection apparatus according to the fourth embodiment of the present invention.

As shown in FIG. 72, if a sound ray equivalent to refraction angle $\Theta$ s1$a$ exists in the effective beam width of the foregoing transmitted transverse ultrasonic beam and a sound ray equivalent to refraction angle $\Theta$ L2$b$ exists in the effective beam width of the foregoing received longitudinal ultrasonic beam at the same time, that is, if $\Theta$ sL$a \leq \Theta$ s1$a \leq \Theta$ sHa and also $\Theta$ LLb$\leq \Theta$ L2$b \leq \Theta$ LHb at the same time, then the propagation path of the ultrasonic wave indicated by a solid line with an arrow, a dotted line with an arrow which continues therefrom, and a dotted line with an arrow which further continues therefrom in the directions shown by the arrows in the drawing may exist. Specifically, a transverse ultrasonic wave transmitted from the transmitting probe 7A to the test object 1 propagates toward the defect 6 as indicated by the solid line with the arrow. After that, the transverse ultrasonic wave directly hits the defect 6 and is reflected by the defect 6 as a longitudinal ultrasonic wave. Then, the reflected longitudinal ultrasonic wave propagates toward the bottom 4 as shown by the dotted line with the arrow. The longitudinal ultrasonic wave is then reflected once on the bottom 4 as the longitudinal ultrasonic wave. The reflected longitudinal ultrasonic wave then reaches the receiving probe 7B as indicated by the dotted line with the arrow and is received as an echo.

The description above has been given to the cases where the ultrasonic waves transmitted from the transmitting probe 7A to the test object 1 are transverse waves and to the propagation paths wherein the transverse waves are directly applied to the defect 6, reflected by the defect 6, then reflected once on the bottom 4 before reaching the receiving probe 7B. At this time, the mode conversion at the defect 6 and the bottom 4 has been taken into account.

Referring now to FIG. 73 and FIG. 74, other cases where the ultrasonic waves transmitted from the transmitting probe 7A to the test object 1 are longitudinal ultrasonic waves will be discussed. Propagation path I through propagation path IV shown in FIG. 73 and propagation path V through propagation path VIII shown in FIG. 74 are other propagation paths which may exist when the ultrasonic waves transmitted from the transmitting probe 7A to the test object 1 are longitudinal waves.

In FIG. 73, propagation path I through propagation path IV are the paths wherein a longitudinal ultrasonic wave transmitted from the transmitting probe 7A propagates toward the bottom 4 of the test object 1, then it is reflected once on the bottom 4 before it propagates toward the defect 6; after that, it is reflected by the defect 6, then it directly propagates toward the receiving probe 7B to be received by the receiving probe 7B as an echo although the paths are not illustrated.

In propagation path I among these four propagation paths I through IV, the propagation mode from the transmitting probe 7A to the bottom 4 is the longitudinal wave mode; the ultrasonic wave is reflected on the bottom 4 as a transverse ultrasonic wave and the propagation mode from the bottom 4 to the defect 6 is the transverse wave mode, and it is reflected at the defect 6 as a transverse ultrasonic wave, then the propagation mode from the defect 6 to the receiving probe 7B is the transverse wave mode. In FIG. 73, in order to simplify propagation path I, only the propagation modes of the ultrasonic wave which propagates along propagation path I are given as representative characters. More specifically, the propagation modes in propagation path I are expressed as the longitudinal wave mode, the transverse wave mode, and the transverse wave mode in order from the left to the right in the table. This means that the mode given firstly corresponds to the propagation mode of the ultrasonic wave transmitted from the transmitting probe 7A to the test object 1; the mode given secondly corresponds to the propagation mode of the ultrasonic wave which is reflected on the bottom 4 and propagated from the bottom 4 to the defect 6; and the mode given thirdly corresponds to the propagation mode of the ultrasonic wave which is propagated from the defect 6 to the receiving probe 7B. For reference, the column next to the three modes in FIG. 73 shows the conditions under which propagation path I may exist, with respect to the effective beam width of the transmitted longitudinal ultrasonic beam, the effective beam width of the received transverse ultrasonic beam, and the effective beam width of the received longitudinal ultrasonic beam. For further reference, whether mode conversion results from the reflection on the bottom 4 and the reflection at the defect 6 is also shown in FIG. 73; "YES" means that mode conversion takes place, and "NO" means that no mode conversion takes place. The same applies to propagation paths II through IV in FIG. 73.

Propagation path II in FIG. 73 is a propagation path wherein the propagation mode from the transmitting probe 7A to the bottom 4 is the longitudinal wave mode; the ultrasonic wave is reflected on the bottom 4 as a longitudinal ultrasonic wave and the propagation mode from the bottom 4 to the defect 6 is the longitudinal wave mode, and it is reflected at the defect 6 as a transverse ultrasonic wave, then the propagation mode from the defect 6 to the receiving probe 7B is the transverse wave mode.

Propagation path III in FIG. 73 is a propagation path wherein the propagation mode from the transmitting probe 7A to the bottom 4 is the longitudinal wave mode; the ultrasonic wave is reflected on the bottom 4 as a transverse ultrasonic wave and the propagation mode from the bottom 4 to the defect 6 is the transverse wave mode, and it is reflected at the defect 6 as a longitudinal ultrasonic wave, then the propagation mode from the defect 6 to the receiving probe 7B is the longitudinal wave mode.

Propagation path IV in FIG. 73 is a propagation path wherein the propagation mode from the transmitting probe 7A to the bottom 4 is the longitudinal wave mode; the ultrasonic wave is reflected on the bottom 4 as a longitudinal ultrasonic wave, and the propagation mode from the bottom 4 to the defect 6 is the longitudinal wave mode, and it is reflected at the defect 6 as a longitudinal ultrasonic wave, then the propagation mode from the defect 6 to the receiving probe 7B is the longitudinal wave mode.

In FIG. 74, propagation path V through propagation path VIII are the paths wherein a longitudinal ultrasonic wave transmitted from the transmitting probe 7A propagates toward the defect 6, then it is reflected by the defect 6 and propagated toward the bottom 4; after that, it is reflected once on the bottom 4 and propagated toward the receiving probe 7B to be received by the receiving probe 7B as an echo although the paths are not illustrated.

In propagation path V among these four propagation paths V through VIII, the propagation mode from the transmitting probe 7A to the defect 6 is the longitudinal wave mode; the ultrasonic wave is reflected at the defect 6 as a transverse ultrasonic wave and the propagation mode from the defect 6 to the bottom 4 is the transverse wave mode, and it is reflected on the bottom 4 as a transverse ultrasonic wave, then the propagation mode from the bottom 4 to the receiving probe 7B is the transverse wave mode. In FIG. 74, in order to simplify propagation path V, only the propagation modes of the ultrasonic wave which propagates along propagation path V are given as representative characteristics. More specifically, the propagation modes in propagation path V are expressed as longitudinal wave, transverse wave, and transverse wave in order from the left to the right in the table. This means that the mode given firstly corresponds to the propagation mode of the ultrasonic wave transmitted from the transmitting probe 7A to the defect 6; the mode given secondly corresponds to the propagation mode of the ultrasonic wave which is reflected by the defect 6 and propagated from the defect 6 to the bottom 4; and the mode given thirdly corresponds to the propagation mode of the ultrasonic wave which is reflected on the bottom 4 and propagated from the bottom 4 to the receiving probe 7B. For reference, the column next to the three modes in FIG. 74 shows the conditions under which propagation path V may exist, with respect to the effective beam width of the transmitted longitudinal ultrasonic beam, the effective beam width of the received transverse ultrasonic beam, and the effective beam width of the received longitudinal ultrasonic beam. For further reference, whether mode conversion results from the reflection on the bottom 4 and the reflection at the defect 6 is also shown in FIG. 74; "YES" means that mode conversion takes place, and "NO" means that no mode conversion takes place. The same applies to propagation paths VI through VIII in FIG. 74.

Propagation path VI in FIG. 74 is a propagation path wherein the propagation mode from the transmitting probe 7A to the defect 6 is the longitudinal wave mode; the ultrasonic wave is reflected at the defect 6 as a longitudinal ultrasonic wave and the propagation mode from the defect 6 to the bottom 4 is the longitudinal wave mode, and it is reflected at the defect 6 as a longitudinal ultrasonic wave, then the propagation mode from the defect 6 to the bottom 4 is the longitudinal wave mode; the ultrasonic wave is further reflected on the bottom 4 as a transverse ultrasonic wave, and the propagation path from the bottom 4 to the receiving probe 7B is the transverse wave mode.

Propagation path VII in FIG. 74 is a propagation path wherein the propagation mode from the transmitting probe 7A to the defect 6 is the longitudinal wave mode; the ultrasonic wave is reflected at the defect 6 as a transverse ultrasonic wave and the propagation mode from the defect 6 to the bottom 4 is the transverse wave mode, and it is further reflected on the bottom 4 as a longitudinal ultrasonic wave, then the propagation mode from the bottom 4 to the receiving probe 7B is the longitudinal wave mode.

Propagation path VIII in FIG. 74 is a propagation path wherein the propagation mode from the transmitting probe 7A to the defect 6 is the longitudinal wave mode; the ultrasonic wave is reflected at the defect 6 as a longitudinal ultrasonic wave, and the propagation mode from the defect 6 to the bottom 4 is the longitudinal wave mode, and it is reflected on the bottom 4 as a longitudinal ultrasonic wave, then the propagation mode from the bottom 4 to the receiving probe 7B is the longitudinal wave mode.

Thus, in order to make the description easy to understand, the consideration has been given to the cases wherein the sound ray equivalent to refraction angle $\Theta$ s1$a$ related to the transverse ultrasonic wave transmitted from the transmitting probe 7A to the test object 1, the sound ray equivalent to refraction angle $\Theta$ s2$a$ related to the transverse ultrasonic wave, and the sound ray equivalent to refraction angle $\Theta$ s2'$a$ related to the transverse ultrasonic wave exist in the effective beam width of the transmitted transverse ultrasonic beam; the sound ray equivalent to refraction angle $\Theta$ L1$a$ related to the longitudinal ultrasonic wave transmitted from the transmitting probe 7A to the test object 1, the sound ray equivalent to refraction angle $\Theta$ L2$a$ related to the longitudinal ultrasonic wave, and the sound ray equivalent to refraction angle $\Theta$ L2'$a$ related to the longitudinal ultrasonic wave exist in the effective beam width of the transmitted longitudinal ultrasonic beam; the sound ray equivalent to refraction angle $\Theta$ s1$b$ related to the transverse ultrasonic wave received by the receiving probe 7B, the sound ray equivalent to refraction angle $\Theta$ s2$b$ related to the transverse ultrasonic wave, and the sound ray equivalent to refraction angle $\Theta$ s2'$b$ related to the transverse wave exist in the effective beam width of the received transverse ultrasonic beam; and the sound ray equivalent to refraction angle $\Theta$ L1$b$ related to the longitudinal ultrasonic wave received by the receiving probe 7A, the sound ray equivalent to refraction angle $\Theta$ L2$b$ related to the longitudinal ultrasonic wave, and the sound ray equivalent to refraction angle $\Theta$ L2'$b$ related to the longitudinal ultrasonic wave exist in the effective beam width of the received longitudinal ultrasonic beam. In other words, the cases wherein one reflection on the bottom 4 is involved in the ultrasonic beam propagation paths have been considered.

If the effective beam widths of the transmitted transverse ultrasonic beam, the transmitted longitudinal ultrasonic beam, the received transverse ultrasonic beam, and the received longitudinal ultrasonic beam, respectively, are greater than those discussed above, then more propagation paths which are different from the propagation paths shown above may exist. Specifically, for example, there may be a propagation path which involves a total of two reflection, i.e. one reflection on the bottom 4 and one reflection on the surface 3. In this case, there may be also various propagation paths which are established by taking into account the mode conversion from transverse wave to longitudinal wave and conversely from longitudinal wave to transverse wave at the bottom 4, the surface 3, and the defect 6, respectively.

As the beam width increases, it becomes necessary to consider paths up to those that include two bounces on the bottom 4 and one bounce on the surface 3 and also to consider mode conversion at each reflection. If the beam width further increases, it is required to consider paths up to those that include two bounces on the bottom 4 and two bounces on the surface 3 and also to consider mode conversion at each reflection.

Likewise, as the beam width grows greater, the number of reflections on the bottom 4 and the surface 3 increases in regard to the paths to be considered and it becomes necessary to take mode conversion at each reflection into account.

Thus, one of the considerable differences of the fourth embodiment from the conventional apparatuses and methods is that it provides a method and an apparatus for detecting a flaw at an angle by taking the divergence of transmitted ultrasonic beams and received ultrasonic beams into account. Further, another difference of the fourth embodiment from the prior arts is that the transmitted transverse ultrasonic beams and transmitted longitudinal ultrasonic beams are considered as the transmitted ultrasonic beams, and also the received transverse ultrasonic beams and the received longitudinal ultrasonic beams are considered as the received ultrasonic waves. Moreover, the fourth embodiment is entirely different from the prior art disclosed in Japanese Unexamined Patent Publication No. 2-278149, Japanese Unexamined Patent Publication No. 2-248855, or Japanese Unexamined Patent Publication No. 5-172789 in that it also considers the reflections on the surface 3 and the bottom 4. Furthermore, the fourth embodiment differs from the prior art in that it takes into account the mode conversion from a transverse wave to a longitudinal wave and the mode conversion from a longitudinal wave to a transverse wave for each reflection of the bottom 4, the surface 3, and the defect 6, respectively.

Based on the consideration results concerning the ultrasonic beam propagation paths discussed above, the signal processing procedure in the signal processor 84C will be described with reference to FIG. 75 through FIG. 79. The coordinate origins in FIG. 76 through FIG. 79 are different from those in FIG. 56, FIG. 57, and FIG. 61 through FIG. 72. Obviously, the origin may be established anywhere. It is apparent that, if the origin is different from that when the transmitting probe 7A and the receiving probe 7B perform scanning, then the coordinate conversion must be performed accordingly in the signal processing in the signal processor 8C.

As previously mentioned, there are stored in the signal processor 84C the echo waveforms at respective spacial points in the scanning zone which have been obtained when the predetermined scanning zone was scanned with the transmitting probe 7A and the receiving probe 7B and the information on the spacial positions of the transmitting probe 7A and the spacial positions of the receiving probe 7B at the time when the echo waveforms were received. The echo waveforms are stored as raw waveforms, i.e. AC (alternating current) waveforms which have not been subjected to such processing as rectification or detection.

The signal processing procedure implemented by the signal processor 84C will be described by taking a case, which involves one reflection on the bottom 4 of the test object 1, as an example to simplify the description in conjunction with FIG. 75. Cases where one or two or more reflections on the surface 3, and two or more reflections on the bottom 4 are to be considered can be fulfilled by expanding the signal processing procedure set forth below.

In step 71 shown in FIG. 75, a predetermined image reconstructing zone is defined. Specifically, in FIG. 76 through FIG. 79, a zone, wherein an image should be displayed as a flaw detection result of the test object 1, is defined as indicated, for example, by the dotted line.

In step 72, an image reconstructing point is specified. The image reconstructing point is one point in the foregoing image reconstructing zone. The coordinates of this point are set to (xi, yi) as shown in FIG. 76 through FIG. 79.

In step 73, the output corresponding to the image reconstructing point (xi, yi) is defined as P (xi, yi), and the value is set to zero. More specifically, the value is set as P (xi, yi)=0.

Figure 76:
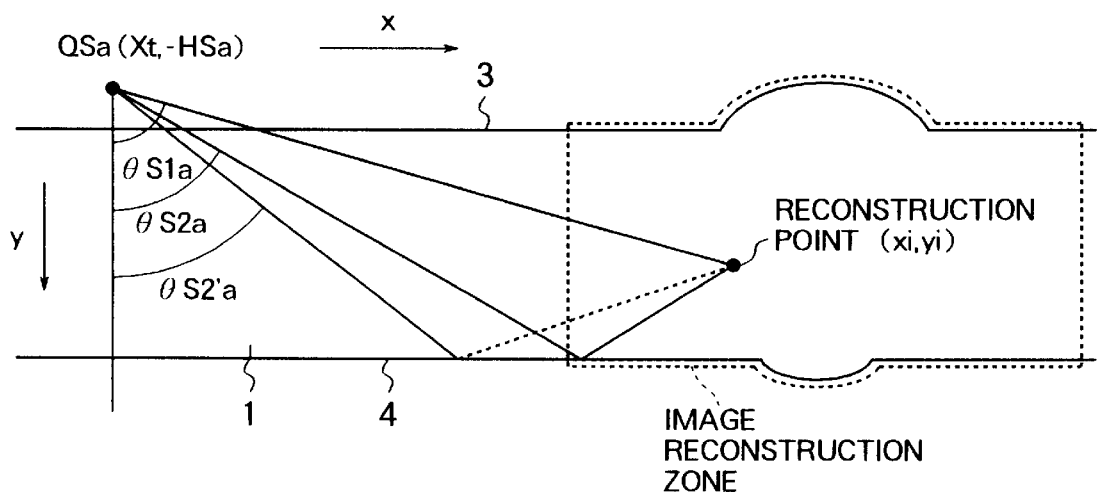
FIG. 76 is a diagram showing a propagation path of an ultrasonic beam for describing the signal processing of the ultrasonic flaw detection apparatus according to the fourth embodiment of the present invention.
Figure 77:
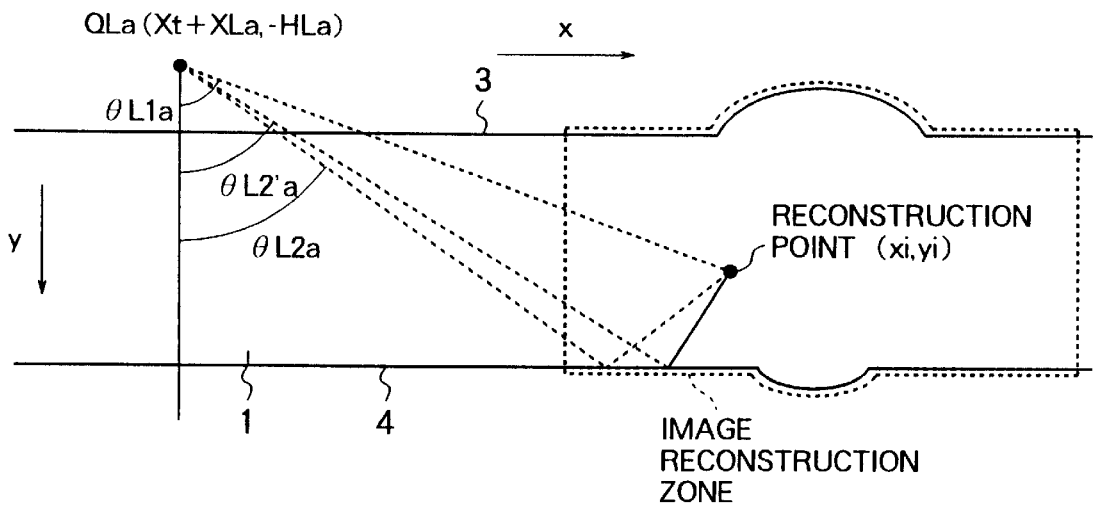
FIG. 77 is a diagram showing a propagation path of an ultrasonic beam for describing the signal processing of the ultrasonic flaw detection apparatus according to the fourth embodiment of the present invention.

In step 74, a spacial position of the transmitting probe 7A, at which an echo has been received, is selected in the scanning zone of the transmitting probe 7A. As shown in FIG. 76, the position of the transmitting probe 7A is represented by point Qsa which is the center of the apparent transducer 72A regarding the transverse waves of the transmitting probe 7A and the coordinates of the position are taken as (xt, −Hsa) when consideration is given concerning transmitted transverse ultrasonic beams. The meaning of point Qsa is the same as in FIG. 59 through FIG. 72. Further, as illustrated in FIG. 77, when consideration is given concerning transmitted longitudinal ultrasonic beams, the position of the transmitting probe 7A is represented by point QLa which is the center of the apparent transducer regarding the longitudinal waves of the transmitting probe 7A, and the coordinates of the position are taken as (xt+xLa, −HLa). The meaning of point QLa is the same as in FIG. 59 through FIG. 72.

In step 75, angles $\theta\, s1a$, $\theta\, s2a$, and $\theta\, s2'a$ shown in FIG. 76 and angles $\theta\, L1a$, $\theta\, L2a$, and $\theta\, L2'a$ shown in FIG. 77 are calculated.

If the image reconstructing point is tentatively regarded as the reflection source, and the beam propagation path wherein an ultrasonic wave transmitted from the transmitting probe 7A reaches the image reconstructing point (xi, yi) is applied, then these angles $\theta\, a1a$, $\theta\, s2a$, $\theta\, s2'a$, $\theta\, L1a$, $\theta\, L2a$, and $\theta\, L2'a$ will be as set forth below.

Angle $\theta\, s1a$ corresponds to a beam propagation path wherein a transverse ultrasonic wave transmitted from the transmitting probe 7A directly reaches the image reconstructing point (xi, yi). Hereinafter, this beam propagation path will be referred to as "the outbound propagation path corresponding to angle $\theta\, a1a$."

Angle $\theta\, s2a$ corresponds to a beam propagation path wherein a transverse ultrasonic wave transmitted from the transmitting probe 7A is reflected once on the bottom 4 as the transverse ultrasonic wave, then it reaches the image reconstructing point (xi, yi). Hereinafter, this beam propagation path will be referred to as "the outbound propagation path corresponding to angle $\theta\, s2a$."

Angle $\theta\, s2'a$ corresponds to a beam propagation path wherein a transverse ultrasonic wave transmitted from the transmitting probe 7A is reflected once on the bottom 4 as a longitudinal ultrasonic wave, then it reaches the image reconstructing point (xi, yi). Hereinafter, this beam propagation path will be referred to as "the outbound propagation path corresponding to angle $\theta\, s2'a$."

Angle $\theta\, L1a$ corresponds to a beam propagation path wherein a longitudinal ultrasonic wave transmitted from the transmitting probe 7A directly reaches the image reconstructing point (xi, yi). Hereinafter, this beam propagation path will be referred to as "the outbound propagation path corresponding to angle θ L1a."

Angle θ L2a corresponds to a beam propagation path wherein a longitudinal ultrasonic wave transmitted from the transmitting probe 7A is reflected once on the bottom 4 as the longitudinal ultrasonic wave, then it reaches the image reconstructing point (xi, yi). Hereinafter, this beam propagation path will be referred to as "the outbound propagation path corresponding to angle θ L2a."

Angle θ L2'a corresponds to a beam propagation path wherein a longitudinal ultrasonic wave transmitted from the transmitting probe 7A is reflected once on the bottom 4 as a transverse ultrasonic wave, then it reaches the image reconstructing point (xi, yi). Hereinafter, this beam propagation path will be referred to as "the outbound propagation path corresponding to angle θ L2'a."

In this example, only one reflection on the bottom 4 is considered and no reflection on the surface 3 is taken into account; only the foregoing six angles θ s1a, θ s2a, θ s2'a, θ L1a, θ L2a, and θ L2'a are calculated. If cases, where two or more reflections on the bottom 4 are involved, or one or two or more reflections on the surface 3 are involved, are to be taken into account, then it is necessary to calculate the angles corresponding to the outbound propagation paths along which the transverse ultrasonic waves and the longitudinal ultrasonic waves transmitted from the transmitting probe 7A reach the image reconstructing point (xi, yi) by also considering the reflections on the respective surfaces and the mode conversions resulting from the reflections in addition to the above six angles.

In step 76, it is determined whether angles θ s1a, θ s2a, and θ s2'a obtained in step 75 lie in the effective beam width of the transmitted transverse ultrasonic beam related to the transmitting probe 7A. Then, angles that lie within the effective beam width of the transmitted transverse ultrasonic beam are selected among angles θ s1a, θ s2a, and θ s2'a. Specifically, θ ska which satisfies the condition shown below is selected, k being 1, 2, and 2'.

$$\theta sLa \leq \theta ska \leq \theta sHa$$

The angles selected as θ ska satisfying the condition given above are denoted as θ spa through θ sqa, where p and q are integers existing among 1, 2, and 2'.

Further in step 76, it is determined whether angles θ L1a, θ L2a, and θ L2'a obtained in step 75 lie in the effective beam width of the transmitted longitudinal ultrasonic beam related to the transmitting probe 7A. Then, angles that lie within the effective beam width of the transmitted longitudinal ultrasonic beam are selected among angles θ L1a, θ L2a, and θ L2'a. Specifically, θ Lka which satisfies the condition shown below is selected, k being 1, 2, and 2'.

$$\theta LLa \leq \theta Lka \leq \theta LHa$$

The angles selected as θ Lka satisfying the condition given above are denoted as θ Lp'a through θ Lq'a, where p' and q' are integers existing among 1, 2, and 2'.

In step 76, the ultrasonic beam propagation paths (outbound propagation paths) have been extracted along which the ultrasonic wave transmitted from the transmitting probe 7A reaches the image reconstructing point (xi, yi) under the condition which involves one reflection on the bottom 4.

If neither θ ska nor θ Lka satisfying the above condition exists, then the program proceeds to step 86. This step 86 will be discussed later.

Figure 78:
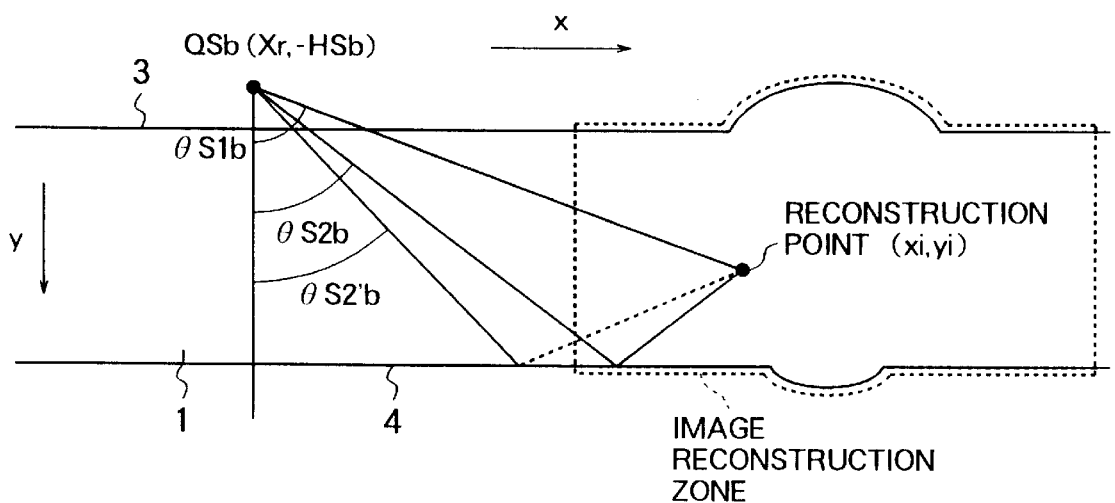
FIG. 78 is a diagram showing a propagation path of an ultrasonic beam for describing the signal processing of the ultrasonic flaw detection apparatus according to the fourth embodiment of the present invention.

In step 77, a spatial position of the receiving probe 7B, at which an echo has been received, is selected at the position of the transmitting probe 7A selected in step 74 in the scanning zone of the receiving probe 7B. As shown in FIG. 78, the position of the receiving probe 7B is represented by point Qsb which is the center of the apparent transducer 72B regarding the transverse waves of the receiving probe 7B and the coordinates of the position are taken as (xr, −Hsb) when consideration is given concerning received transverse ultrasonic beams. The meaning of point Qsb is the same as in FIG. 59 through FIG. 72. Further, as illustrated in FIG. 79, when consideration is given concerning received longitudinal ultrasonic beams, the position of the receiving probe 7B is represented by point QLb which is the center of the apparent transducer regarding the longitudinal waves of the receiving probe 7B, and the coordinates of the position are taken as (xr+xLb, −HLb) The meaning of point QLb is the same as in FIG. 59 through FIG. 72.

Figure 79:
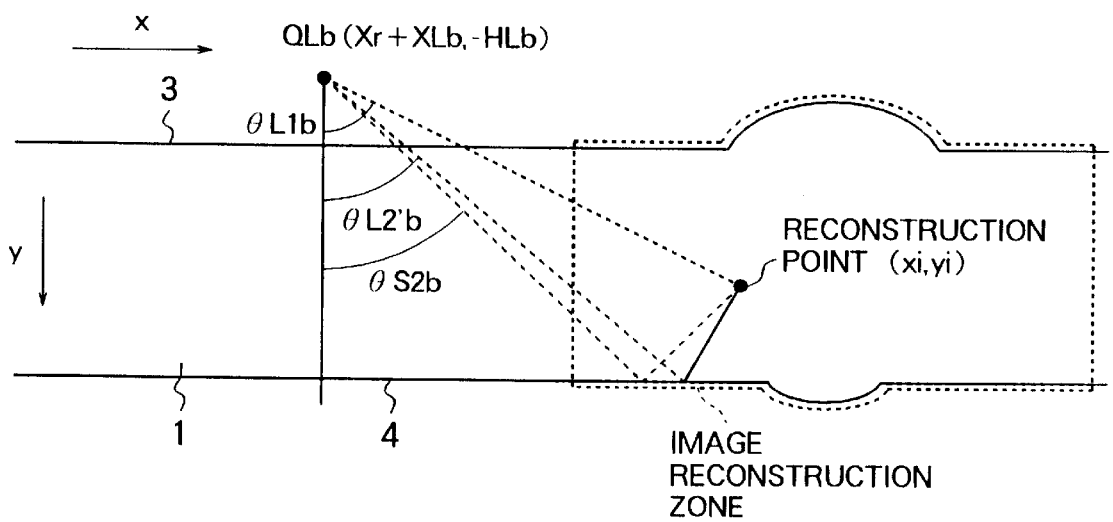
FIG. 79 is a diagram showing a propagation path of an ultrasonic beam for describing the signal processing of the ultrasonic flaw detection apparatus according to the fourth embodiment of the present invention.
Figure 80:
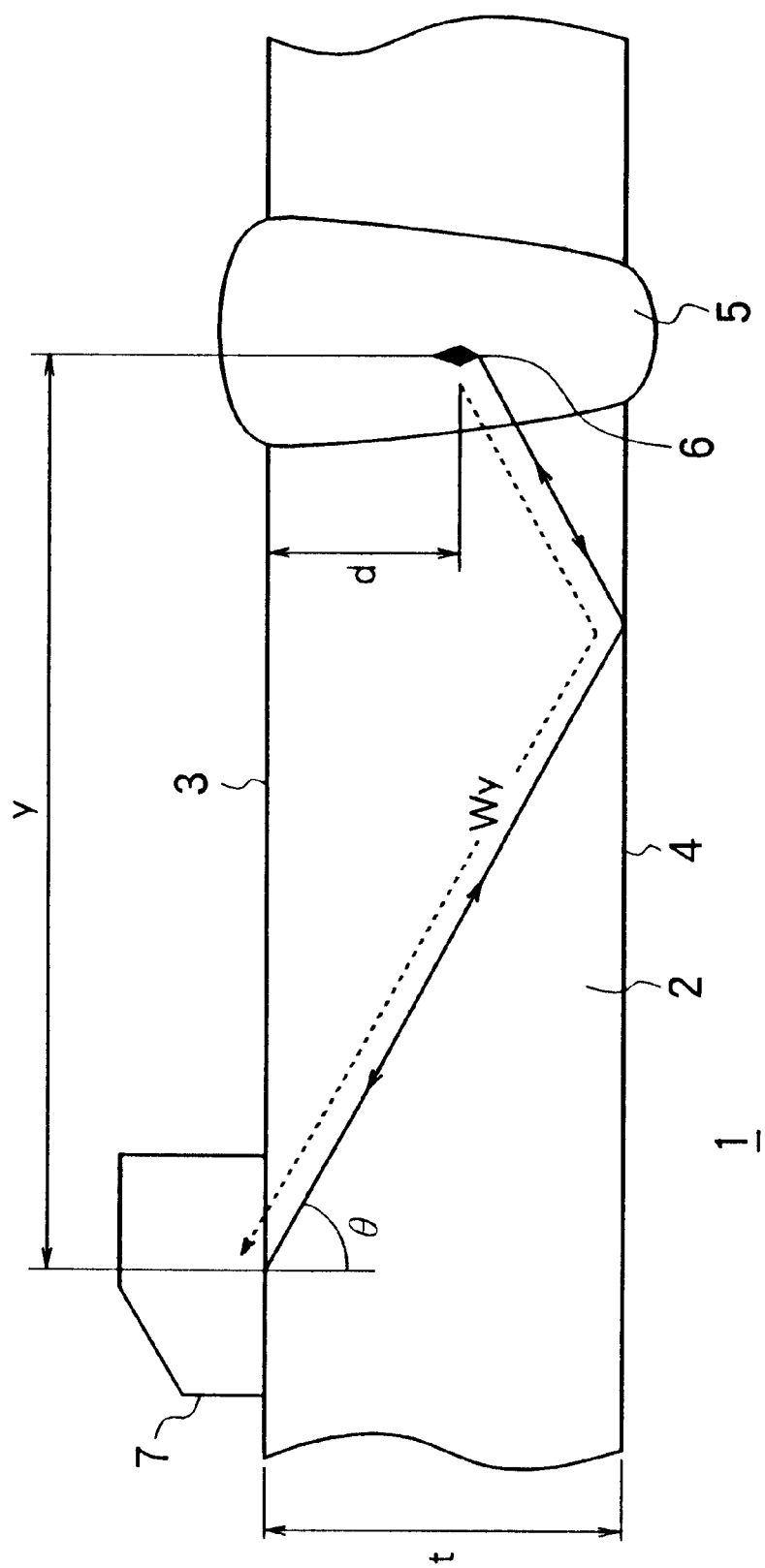
FIG. 80 is a diagram for describing a conventional ultrasonic angle-beam flaw detection technique.

In step 78, angles θ s1b, θ s2b, and θ s2'b shown in FIG. 78 and angles θ L1b, θ L2b, and θ L2'b shown in FIG. 79 are calculated.

If the image reconstructing point (xi, yi) is tentatively regarded as the reflection source, and the beam propagation path wherein an ultrasonic wave reflected from the point reflection source reaches the receiving probe 7B to be received as an echo is applied, then these angles θ s1b, θ s2b, θ s2'b, θ L1b, θ L2b, and θ L2'b will be as set forth below.

Angle θ s1b corresponds to a beam path wherein a transverse ultrasonic wave reflected at the image reconstructing point directly reaches the receiving probe 7B. Hereinafter, this beam propagation path will be referred to as "the inbound propagation path corresponding to angle θ s1b."

Angle θ s2b corresponds to a beam propagation path wherein a transverse ultrasonic wave reflected at the image reconstructing point is reflected once on the bottom 4 as the transverse ultrasonic wave, then it reaches the receiving probe 7B. Hereinafter, this beam propagation path will be referred to as "the inbound propagation path corresponding to angle θ s2b."

Angle θ s2'b corresponds to a beam propagation path wherein a longitudinal ultrasonic wave reflected at the image reconstructing point is reflected once on the bottom 4 as a transverse ultrasonic wave, then it reaches the receiving probe 7B. Hereinafter, this beam propagation path will be referred to as "the inbound propagation path corresponding to angle θ s2'b."

Angle θ L1b corresponds to a beam propagation path wherein a longitudinal ultrasonic wave reflected at the image reconstructing point directly reaches the receiving probe 7B. Hereinafter, this beam propagation path will be referred to as "the inbound propagation path corresponding to angle θ L1b."

Angle θ L2b corresponds to a beam propagation path wherein a longitudinal ultrasonic wave reflected at the image reconstructing point is reflected once on the bottom 4 as the longitudinal ultrasonic wave, then it reaches the receiving probe 7B. Hereinafter, this beam propagation path will be referred to as "the inbound propagation path corresponding to angle θ L2b."

Angle θ L2'b corresponds to a beam propagation path wherein a transverse ultrasonic wave reflected at the image reconstructing point is reflected once on the bottom 4 as a longitudinal ultrasonic wave, then it reaches the receiving probe 7B. Hereinafter, this beam propagation path will be referred to as "the inbound propagation path corresponding to angle θ L2'b."

In this example also, only one reflection on the bottom 4 is considered and no reflection on the surface 3 is taken into account in the inbound propagation paths of ultrasonic beams; only the foregoing six angles $\theta$ s1$b$, $\theta$ s2$b$, $\theta$ s2'$b$, $\theta$ L1$b$, $\theta$ L2$b$, and $\theta$ L2'$b$ are calculated. If cases where two or more reflections on the bottom 4 are involved, or one or two or more reflections on the surface 3 are involved are to be taken into account, then it is necessary to calculate the angles corresponding to the inbound propagation paths along which the transverse ultrasonic waves and the longitudinal ultrasonic waves reflected at the image reconstructing point reach the receiving probe 7B by also considering the reflections on the respective surfaces and the mode conversions resulting from the reflections in addition to the above six angles.

In step 79, it is determined whether angles s1$b$, $\theta$ s2$b$, and $\theta$ s2'$b$ obtained in step 78 lie in the effective beam width of the received transverse ultrasonic beam related to the receiving probe 7B. Then, angles that lie within the effective beam width of the received transverse ultrasonic beam are selected among angles $\theta$ s1$b$, $\theta$ s2$b$, and $\theta$ s2'$b$. Specifically, $\theta$ skb which satisfies the condition shown below is selected, k being 1, 2, and 2'.

$$\theta sLb \leq \theta skb \leq \theta sHb$$

The angles selected as $\theta$ skb satisfying the condition given above are denoted as $\theta$ sp"a through $\theta$ sq"a, where p" and q" are integers existing among 1, 2, and 2'.

Further in step 79, it is determined whether angles $\theta$ L1$b$, $\theta$ L2$b$, and $\theta$ L2'$b$ obtained in step 78 lie in the effective beam width of the received longitudinal ultrasonic beam related to the receiving probe 7B. Then, angles that lie within the effective beam width of the received longitudinal ultrasonic beam are selected among angles $\theta$ L1$b$, $\theta$ L2$b$, and $\theta$ L2'$b$. Specifically, $\theta$ Lkb which satisfies the condition shown below is selected, k being 1, 2, and 2'.

$$\theta LLb \leq \theta Lkb \leq \theta LHb$$

The angles selected as $\theta$ Lkb satisfying the condition given above are denoted as $\theta$ Lp'"b through $\theta$ Lq'"b, where p'"and q'" are integers existing among 1, 2, and 2'.

In step 79, the ultrasonic beam propagation paths (inbound propagation paths) have been extracted along which the ultrasonic wave reflected at the image reconstructing point reaches the receiving probe 7B under the condition which involves one reflection on the bottom 4.

If neither $\theta$ skb nor $\theta$ Lkb satisfying the above condition exists, then the program proceeds to step 87. This step 87 will be discussed later.

In step 80, based on the outbound propagation paths of ultrasonic beams extracted in step 76 and the inbound propagation paths extracted in step 79, all combinations of round trip propagation paths composed of the aforesaid outbound and inbound propagation paths are extracted. As previously mentioned, the outbound propagation paths refer to the propagation paths in which the ultrasonic wave transmitted from the transmitting probe 7A reaches the image reconstructing point (xi, yi) and the inbound propagation paths refer to the propagation paths in which the ultrasonic wave reflected at the image reconstructing point (xi, yi) reaches the receiving probe 7B. The outbound propagation path corresponds to one of angles $\theta$ spa through $\theta$ sqa and angles $\theta$ Lp'a through $\theta$ Lq'a, while the inbound propagation path corresponds to one of angles $\theta$ sp"b through $\theta$ sq"b and angles $\theta$ Lp'"b through $\theta$ Lq'"b. Thus, a variety of round trip propagation paths are likely to exist.

In step 81, on all the combinations of the round trip propagation paths extracted as mentioned above, the propagation time required for an ultrasonic wave to propagate along each of these round trip propagation paths (hereinafter referred to as "round trip propagation paths") are calculated. It is needless to say that, when calculating the round trip propagation time, if the round trip propagation path is composed of a propagation path involving longitudinal wave propagation and a propagation path involving transverse wave propagation, then the sound speed of longitudinal waves must be applied to the beam path length (distance) corresponding to the propagation path which involves longitudinal wave propagation and the sound speed of transverse waves must be applied to the beam path length corresponding to the propagation path which involves transverse wave propagation. Needles to say, if the round trip propagation path is composed only of propagation path involving longitudinal wave propagation, the round trip propagation time can be determined by applying the sound speed of longitudinal waves to the beam length. Likewise, if the round trip propagation path is composed only of propagation path involving transverse wave propagation, the round trip propagation time can be determined by applying the sound speed of transverse waves to the beam length. Thus, based on the round trip propagation time determined for each of the round trip propagation paths, the time when the echos should be received has been determined in the echo waveforms corresponding to the positions which combine the spacial positions of the transmitting probe 7A selected in step 74 and the spacial positions of the receiving probe 7B selected in step 77.

In step 81, the amplitudes of the echos corresponding to the time at which echos are to be received are called up for each of the round trip propagation paths thus determined. Further in step 81, the amplitudes of the echos called up for the respective round trip propagation paths are added, and the result of the addition is added to P (xi, yi).

In step 82, it is determined whether the signal processing from step 77 through step 81 has been completed over the entire scanning zone or a predetermined scanning zone of the receiving probe 7B. If the determination result is negative, then the program goes to step 87; if it is affirmative, then the program proceeds to step 83.

In step 87, the receiving probe 7B is moved to another spacial position and the signal processing from step 77 to step 82 is continued. Specifically, in step 77, a new spatial position (the position after the aforesaid movement) of the receiving probe 7B excluding the spatial positions selected previously is selected within the scanning zone of the receiving probe 7B and the signal processing up to step 82 is implemented.

In step 83, it is determined whether the signal processing from step 74 through step 82 has been completed over the entire scanning zone or a predetermined scanning zone of the transmitting probe 7A. If the determination result is negative, then the program goes to step 86; if it is affirmative, then the program proceeds to step 84.

In step 86, the transmitting probe 7A is moved to another spacial position and the signal processing from step 74 through step 83 is continued. Specifically, in step 74, a new spatial position (the position after the aforesaid movement) of the transmitting probe 7A excluding the spacial positions selected previously is selected within the scanning zone of the transmitting probe 7A and the signal processing up to step 83 is implemented.

In step 84, the value of P (xi, yi) or an absolute value thereof or a square value of the absolute value or the like is output as a reconstructed image at the image reconstructing point (xi, yi).

In step 85, it is determined whether the signal processing from step 72 to step 84 has been completed on all predetermined reconstruction points or established reconstruction points in the predetermined image reconstruction zone. If the determination result is negative, then the program proceeds to step 88. If the determination result is affirmative, then it means that all signal processing in the signal processor 84C has been completed.

In step 88, another predetermined image reconstruction point is specified in a predetermined image reconstruction zone, and the signal processing from step 72 to step 85 is repeated.

In order to simplify the description, the procedure for identifying the candidates of round trip propagation paths has been described by taking the examples wherein one reflection on the bottom 4 of the test object 1 is taken into account. If two or more reflections on the bottom 4 are involved, or one or two or more reflections on the surface 3 are involved, then the reflections on the bottom 4 or the surface 3 and the mode conversions resulting from the reflections are to be taken into account when identifying the candidates of the round trip propagation paths from the transmitting probe 7A via the image reconstruction point to the receiving probe 7B in steps 75 through 80.

Step 75 through step 80 indicate just one specific example of the signal processing procedure for identifying the candidates of the round trip propagation paths from the transmitting probe 7A via the image reconstruction point to the receiving probe 7B when the spacial position (coordinates) of the transmitting probe 7A, the spatial position of the receiving probe 7B, and the spatial position of the image reconstruction point are given. The candidates of such round trip propagation paths may be identified by following a different procedure than the signal processing procedure indicated by steps 75 through step 80. In short, a different procedure from that shown in FIG. 75 may be used as long as it is a procedure which makes it possible to identify the round trip propagation paths from the transmitting probe 7A via the image reconstruction point to the receiving probe 7B when the spatial position of the transmitting probe 7A, the spatial position of the receiving probe 7B, and the spatial position of the image reconstruction point are given. In identifying the aforesaid candidates of the round trip propagation paths, if it is required to assume the candidates of the round trip propagation paths involving the reflections of ultrasonic pulses on the bottom 4 and the surface 3, then it is of course necessary to also consider those involving the reflections on the bottom 4 and the surface 3.

Further, in step 81 of the signal processing shown above, the time when the echo is to be received has been determined on each of all the round trip propagation paths and the amplitude of the echo corresponding to the time has been called up and added; attention should be paid to the following when carrying out the addition. When the ultrasonic wave is reflected once on the bottom 4, the phase thereof changes. Likewise, when the ultrasonic wave is reflected on the surface 3, the phase thereof also changes. It is necessary, therefore, to correct the change in the phase involved in the reflection when performing the addition. A case wherein the phase change resulting from a reflection leads, for example, to a reversed phase (180 degrees) will be described. It is assumed, for instance, that there are such round trip beam paths as a path (first path) wherein a transverse ultrasonic pulse transmitted from the transmitting probe 7A directly hits the defect 6 and it is reflected by the defect 6 as the transverse wave, then received directly by the receiving probe 7B, a path (second path) wherein a transverse ultrasonic pulse transmitted from the transmitting probe 7A is directly applied to the defect 6 and reflected by the defect 6 as a transverse wave, then reflected once on the bottom 4 as the transverse wave before it is received by the receiving probe 7B, and a path (third path) wherein a transverse ultrasonic pulse transmitted from the transmitting probe 7A is directly applied to the defect 6 and reflected by the defect 6 as the transverse wave, then it is reflected once on the surface 3 as the transverse wave and further reflected once on the bottom 4 as the transverse wave before it is received by the receiving probe 7B. In this case, in the second path, since the ultrasonic pulse is reflected once on the bottom 4, the phase is shifted 180 degrees in comparison with the first path. In the third path, since the ultrasonic pulse is reflected once on the surface 3 and also once on the bottom 4, the total shift of the phase amounts to 360 degrees in comparison with the first path, meaning that the phase is identical to that in the first path as a result. Hence, the amplitude of the echo corresponding to the first path and the amplitude of the echo corresponding to the third path are added as they are, whereas the value of the amplitude of the echo corresponding to the second path is multiplied by −1 to provide a value obtained by reversing the phase is to be added to the amplitudes which correspond to the first and second paths. The same must be taken into account for the phase changes resulting from the reflections at the defect 6. The above description has been given to the cases wherein the phase shift is 180 degrees; for other angles, a certain reference phase should be determined so that the deviation of a phase change attributable to a reflection from the reference value can be corrected before carrying out the addition of the amplitudes of echos. This enables sharper reconstructed images to be achieved.

In step 81 of the signal processing described above, as in the cases of other embodiments, if the amplitude of the echo of the time corresponding to a round trip propagation path has a value which is not more than a predetermined signal-to-noise ratio, then processing with this amplitude taken as zero may, in some cases, reduce the influences by noises on a reconstructed image acquired as a final result. In such a case, only round trip propagation paths that have significant corresponding echo amplitudes are selected among all the possible round trip propagation paths which have been extracted in step 80, and the amplitudes of echos corresponding thereto are added and the addition result is added to P (xi, yi) to enable a preferable result to be obtained.

Further, in step 75 through step 80 of the signal processing described above, or in a procedure for the same purpose as that of these steps, that is, in the procedure for identifying the candidates of the round trip propagation paths, it is not always necessary to find all possible round trip propagation paths as the candidates. If there are possible round trip propagation paths that have been theoretically or experimentally found to provide no echos which are received as the echos having significant levels, then such paths may be eliminated beforehand from the candidates to simplify the determining procedure by concentrating efforts on identifying the remaining candidates. Alternatively, if there are round trip propagation paths that have been theoretically or experimentally found beforehand to provide echos received as the echos of high levels, then the signal processing procedure can be simplified by carrying out the signal processing by specifying the paths in advance. In this case, step 75, step 76, step 78, step 79, and step 80 are unnecessary. Based on the spatial position of the transmitting probe 7A selected in step 74 and the spatial position of the receiving probe 7B selected in step 77, step 81 is implemented on the foregoing specified round trip propagation paths. More specifically, in step 81, the round trip propagation paths specified above may be employed in place of the candidates which have been identified by the procedure of step 75 through step 80.

The method wherein a refraction angle is selected and a round trip beam propagation path is extracted according to the refraction angle is just one extracting method; other methods are possible. Further, it is not always necessary to identify all round trip beam propagation paths; obtaining several candidates is adequate.

As a result of the signal processing described above, the result of the inspection in the test object 1 has been acquired in terms of an image in the fourth embodiment. The operation and advantage of the fourth embodiment will now be described.

Unlike prior arts, in the fourth embodiment, the reflections of the ultrasonic waves on the bottom 4 and the surface 3 of the test object 1 have also been taken into account to identify the candidates of possible round trip propagation paths, and the amplitudes of the echos at the echo receiving time corresponding to these round trip propagation paths have been added. Furthermore, longitudinal waves have been considered in addition to transverse waves as the ultrasonic waves transmitted from the transmitting probe 7A to the test object 1, and longitudinal waves have been considered in addition to transverse waves as the ultrasonic waves received by receiving probe 7B to identify the candidates of the foregoing round trip propagation paths. Moreover, consideration has been given to the mode conversion from a transverse wave to a longitudinal wave on the bottom 4, the surface 3, and the defect 6 of the test object 1, and the mode conversion from a longitudinal wave to a transverse wave on the bottom 4, the surface 3, and the defect 6 in identifying the candidates of the foregoing round trip propagation paths. Further, the result of the addition of echo amplitudes at the echo receiving time corresponding to the round trip propagation paths selected as the candidates has been added in relation to the echos corresponding to the positions composed of the combinations of the respective positions of the transmitting probe 7A in the scanning zone of the transmitting probe 7A and the respective positions of the receiving probe 7B in the scanning zone of the receiving probe 7B. The result of the addition has been output as an image at the image reconstruction point. This makes it possible to reproduce an image with consideration given to the ultrasonic beam propagation paths which were not considered in the past, thus providing an operation and advantage in that more accurate examination result can be obtained than that available with the prior arts. Moreover, the receiving probe 7B as well as the transmitting probe 7A are moved for spatial scanning to increase the number of additions so as to provide an operation and advantage that more accurate inspection results can be acquired; and since the ultrasonic beam propagation paths which are not considered in other embodiments of the present invention are also taken into account to reproduce an image, an operation and advantage, which enable more accurate inspection results than those in other embodiments to be obtained, can be achieved.

If the amplitudes of the echos at the echo receiving time corresponding to round trip propagation paths in the aforesaid identified round trip propagation path candidates have values which are not more than a predetermined signal-to-noise ratio (as in other embodiments of the present invention), then only round trip propagation paths with significant values of amplitudes of corresponding echos are selected among the foregoing round trip propagation paths, and only the amplitudes of echos corresponding thereto are added and the addition result is added to P (xi, yi), thus providing an operation and advantage in that sharper images can be obtained and therefore more accurate examination can be achieved.

Furthermore, if a beam width of −3 dB is used in the transmitted transverse ultrasonic beam for the transmitted transverse ultrasonic beam width related to the transverse wave specified by θ sLa and θ sHa, and the a beam width of −3 dB is used in the received transverse ultrasonic beam for the received transverse ultrasonic beam width related to the transverse wave specified by θ sLb and θ sHb, then signal processing based on principal beam related to transverse waves can be implemented for both transmitting and receiving, thus providing an operation and advantage in that sharper images can be obtained.

Likewise, if a beam width of −3 dB is used in the transmitted longitudinal ultrasonic beam for the transmitted longitudinal ultrasonic beam width related to the longitudinal wave specified by θ LLa and θ LHa, and the beam width of −3 dB is used in the received longitudinal ultrasonic beam for the received longitudinal ultrasonic beam width related to the longitudinal wave specified by θ LLb and θ LHb, then signal processing based on principal beam related to longitudinal waves can be implemented for both transmitting and receiving, thus providing an operation and advantage in that sharper images can be obtained.

The fourth embodiment has referred to a case where an image is reproduced by signal processing by scanning with the transmitting probe 7A and the receiving probe 7B at a particular value of z on a z-axis perpendicular to the x-axis and the y-axis, i.e. within a section of (x, y) although it is not shown; however, the present invention is not limited thereto; the information on the defect 6 along the z-axis can be also obtained by implementing the same scanning by using the transmitting probe 7A and the receiving probe 7B and signal processing along the z-axis, i.e. at diverse values of z, and by reproducing and displaying the final result in terms of a three-dimensional image in the test object 1, thus providing an operation and advantage which allow effective use for classifying, sorting, or the like of the defect 6.

The fourth embodiment further provides the following operation and advantage. Depending on the shape of the defect 6, the characteristics of the reflection of the defect 6 indicate a spatial directivity. For instance, if the defect 6 has a planar shape, the ultrasonic pulse applied to the defect 6 exhibits a specular reflection or a reflection characteristic similar to the specular reflection when no mode conversion takes place from the reflection at the defect 6. In such a case, the ultrasonic wave launched to the defect 6 is not reflected in the incident direction; it is intensively reflected in a direction which is entirely different from the incident direction. If the reflection of the ultrasonic wave at the defect 6 involves the mode conversion from a transverse wave to a longitudinal wave or the mode conversion from a longitudinal wave to a transverse wave, then the mode-converted ultrasonic pulse exhibits the reflection characteristic wherein the incident angle at which the ultrasonic pulse is launched to the defect 6 is different from the angle of reflection as shown in FIG. 56 through FIG. 58 rather than the specular reflection or the reflection characteristic similar to the specular reflection. Further, an ultrasonic pulse of a different mode from the mode of the ultrasonic pulse launched to the defect 6 may be intensively reflected in some cases. Hence, when such mode conversion takes place, the ultrasonic wave launched to the defect 6 is not reflected in the incident direction; it may be intensively reflected in an entirely different direction from the incident direction in some cases. Thus, if the characteristic of the reflection from the defect 6 has spatial directivity, then the ultrasonic pulse reflected at the defect 6 may hardly come back to the transmitting probe 7A which has transmitted the ultrasonic pulse, and an ultrasonic wave of a different mode from the mode of the transmitted ultrasonic wave may be reflected at a high level from time to time.

Similarly, the reflection of an ultrasonic pulse on the bottom 4 or the surface 3 of the test object 1 also exhibits the specular reflection or a reflection characteristic similar to the specular reflection if no mode conversion is involved. If the reflection of an ultrasonic pulse on the bottom 4 or the surface 3 of the test object 1 involves mode conversion, then it shows the reflection characteristic wherein the incident angle of the ultrasonic pulse is different from the angle of reflection, and an ultrasonic wave of a different mode from the mode of the applied ultrasonic wave may be reflected at a high level in some cases. Thus, as in the case of the reflection at the defect 6, the reflection characteristic of an ultrasonic pulse which is reflected on the bottom 4 or the surface 3 of the test object 1 has spatial directivity. For this reason, there is a likelihood that the ultrasonic pulse transmitted from the transmitting probe 7A does not come back at a high level toward the transmitting probe 7A.

There is another likelihood that an ultrasonic wave of a different mode from the mode of the ultrasonic wave transmitted from the transmitting probe 7A may be reflected at a high level. As described above, the fourth embodiment is provided with the receiving probe 7B separately from the transmitting probe 7A so as to move the transmitting probe 7A and the receiving probe 7B for scanning to receive echos. Therefore, even if the characteristic of the reflection from the defect 6 has spatial directivity or even if the characteristic of reflection on the bottom 4 or the surface 3 of the test object 1 has spatial directivity, the fourth embodiment is capable of ensuring higher probability of receiving the ultrasonic pulses reflected by the defect 6 as transverse wave or longitudinal wave echos by the receiving probe 7B. This provides an operation and advantage for improving the capability of preventing oversight of the defect 6.

In the fourth embodiment, on the transverse wave or longitudinal wave echos which have been received at respective spatial positions of the transmitting probe 7A and the receiving probe 7B, the transmitting probe 7A and the receiving probe 7B are used for spatial scanning and the operation of addition is carried out on the echos by the signal processor 84C as described above. Therefore, the levels of the echos obtained as the results of the addition are enhanced. This provides an operation and advantage for achieving further improved capability of detecting the defect 6.

Using different refraction angles for the transmitting probe 7A and the receiving probe 7B, respectively, and also using various different combinations to implement the fourth embodiment on each of the combinations will provide an operation and advantage which permit still higher probability of detecting the defect 6 without overlooking it and thereby achieving sharper images even if the characteristic of reflection from the defect 6 has spatial directivity or the characteristic of reflection from the bottom 4, or the surface 3 of the test object 1 has spatial directivity as described above.

The ultrasonic flaw detection apparatus and the ultrasonic flaw detection method in accordance with the fourth embodiment of the present invention also provide the following operation and advantage. For example, there is such a case as a weld bead wherein it is difficult to transmit and receive ultrasonic waves via the surface of a test object by scanning the transmitting probe and the receiving probe close to a defect because the surface of the test object is badly uneven. In such a case, if there is a defect near the surface of the test object, then no echo from the defect may be obtained by direct scanning because of the aforesaid limitation in the scanning zones of the transmitting probe and the receiving probe wherein ultrasonic waves can be transmitted and received properly. In this case, the transmitting probe and the receiving probe must be disposed on the bottom of the test object to conduct the flaw detection test by using the bottom as the test surface, or the transmitting probe must be disposed on the surface and the receiving probe must be disposed on the bottom to carry out the flaw detection test. In a case, however, where the test object is a part of a structure and the bottom cannot be accessed physically, it is impossible to use the bottom as the test surface. Even in such a case where a defect is located near the surface, the ultrasonic flaw detection apparatus and the ultrasonic flaw detection method according to the present invention employ the reflection of ultrasonic waves on a bottom and the reflection of ultrasonic waves on a surface as well in addition to direct scanning. Therefore, they provide an operation and advantage which allow the foregoing limitation to be overcome and the flaw detecting examination to be achieved by making use of such reflections.

The fourth embodiment of the present invention has referred to the configuration wherein the transmitting probe and receiving probe are disposed on the surface of the test object. However, if the bottom of the test object is also used as a test surface, then either the transmitting probe or the receiving probe may be disposed on the surface and the other on the bottom to carry out the flaw detection test according to the same procedure as that of the fourth embodiment.

So far, the description has been given to the cases where the transmitting probe and the receiving probe are brought in direct contact with the test surface of the test object to carry out the flaw detecting examination. The present invention, however, is not limited thereto; it may also be applied to a so-called immersion method or immersion testing in which a test object is immersed in a liquid such as water and the transmitting probe and the receiving probe transmit and receive ultrasonic waves to and from the test object via the liquid. The present invention may also be applied to a so-called local immersion testing wherein a water film is provided only on the acoustic transmitting and receiving surfaces which are the front surfaces of the transmitting probe and the receiving probe, that is, only in the local space between the transmitting probe and the receiving probe and the test surface of the test object and ultrasonic waves are transmitted to and received from the test object. The same operations and advantages of the present invention described above can be obtained also in such immersion method, immersion testing, and local immersion testing.

In conjunction with FIG. 54, it has been described that the scanners 9A and 9B have the function for the spatial scanning of the transmitting probe 7A and the receiving probe 7B, output the information on the spatial positions of the transmitting probe 7A and the receiving probe 7B, and supply it to the position detector 85. However, the function for gathering and outputting the information on the spatial positions of the transmitting probe 7A and the receiving probe 7B may be implemented by a position information generator provided independently of the scanners 9A and 9B. This means that the information on the spatial positions of the transmitting probe 7A and the receiving probe 7B may alternatively be gathered and output by the position information generator, then supplied to the position detector 85. In this case, the scanners 9A and 9B are responsible only for the function for the spatial scanning of the transmitting probe 7A and the receiving probe 7B. Further, in this case, it is necessary to connect the position information generator to the controller 81 to exchange various types of signals with the controller 81.

Furthermore, in conjunction with FIG. 54, it has been described that the information on the spatial positions of the transmitting probe 7A and the receiving probe 7B is output from the scanners 9A and 98 and applied to the position detector 85. However, since the information on the spatial scanning zones and the travel distances of the transmitting probe 7A and the receiving probe 7B is controlled and generated by the controller 81, the scanners 9A and 9B may be responsible only for the spatial scanning function of the probe 7, and the information on the scanning of the transmitting probe 7A and the receiving probe 7B from the controller 81 may be directly supplied to and stored in the signal processor 84C so as to obviate the need for providing the position detector 85.

Industrial Applicability

As described above, the ultrasonic flaw detection apparatus in accordance with the present invention is equipped with: a probe which is driven by a transmission signal and which transmits an ultrasonic pulse at an angle with respect to a test surface of a test object and receives the ultrasonic pulse, which has been reflected by an acoustically discontinued portion in the test object, as an echo; scanning means for scanning the probe over a predetermined scanning zone on the test object and outputting a spatial position of the probe; and transmitting and receiving means for generating the transmission signal and outputting it to the probe, receiving the echo from the probe and storing it, receiving and storing the spatial position of the probe from the scanning means when the ultrasonic pulse was transmitted and when the echo was received, and detecting the acoustically discontinued portion according to the spatial position of the probe and the echo, taking the spread of an ultrasonic beam attributable to diffraction into account. Therefore, it provides an advantage in that the accuracy of the examination based on an ultrasonic wave through a test object can be improved and the capability of detection and the accuracy of measurement of the shape, size, and position of an acoustically discontinued portion or the like can be improved.

Further, as described above, the ultrasonic flaw detection apparatus in accordance with the present invention is equipped with: a probe which is driven by a transmission signal, and which transmits an ultrasonic pulse at an angle with respect to a test surface of a test object and receives the ultrasonic pulse, which has been reflected by an acoustically discontinued portion in the test object, as an echo; scanning means for scanning the probe over a predetermined scanning zone on the test object and outputting a spatial position of the probe; and transmitting and receiving means for generating the transmission signal and outputting it to the probe, receiving the echo from the probe and storing it, receiving and storing the spatial position of the probe from the scanning means when the ultrasonic pulse was transmitted and when the echo was received, and detecting the acoustically discontinued portion according to the spatial position of the probe and the echo with consideration given to the spread of an ultrasonic beam attributable to diffraction, and the mode conversion from a longitudinal wave to a transverse wave and the mode conversion from a transverse wave to a longitudinal wave when the ultrasonic beam reflects. Therefore, it provides an advantage in that the accuracy of the examination based on an ultrasonic wave through a test object can be improved and the capability of detection of and the accuracy of measurement of the shape, size, and position of an acoustically discontinued portion or the like can be improved.

As described above, the ultrasonic flaw detection method in accordance with the present invention includes: a step for scanning a probe over a predetermined scanning zone on a test object by scanning means; a step for generating a transmission signal and outputting it to the probe, and for transmitting an ultrasonic pulse at an angle with respect to a test surface of the test object by the probe; a step for receiving the ultrasonic pulse, which has been reflected by an acoustically discontinued portion in the test object, as an echo by the probe; a step for receiving the echo from the probe and storing it, and for receiving and storing the spatial position of the probe from the scanning means when the ultrasonic pulse was transmitted and when the echo was received; and a step for detecting the acoustically discontinued portion according to the spatial position of the probe and the echo with consideration given to the spread of an ultrasonic beam attributable to diffraction; therefore, it provides an advantage in that the accuracy of the examination based on an ultrasonic wave through a test object can be improved and the capability of detection of and the accuracy of measurement of the shape, size, and position of an acoustically discontinued portion or the like can be improved.

Furthermore, as described above, the ultrasonic flaw detection method in accordance with the present invention includes: a step for scanning a probe over a predetermined scanning zone on a test object by scanning means; a step for generating a transmission signal and outputting it to the probe, and for transmitting an ultrasonic pulse at an angle with respect to a test surface of the test object by the probe; a step for receiving the ultrasonic pulse, which has been reflected by an acoustically discontinued portion in the test object, as an echo by the probe; a step for receiving the echo from the probe and storing it, and for receiving and storing the spatial position of the probe from the scanning means when the ultrasonic pulse was transmitted and when the echo was received; and a step for detecting the acoustically discontinued portion according to the spatial position of the probe and the echo with consideration given to the spread of an ultrasonic beam attributable to diffraction, and the mode conversion from a longitudinal wave to a transverse wave and the mode conversion from a transverse wave to a longitudinal wave when the ultrasonic beam reflects; therefore, it provides an advantage in that the accuracy of the examination based on an ultrasonic wave through a test body can be improved and the capability of detection of and the accuracy of measurement of the shape, size, and position of an acoustically discontinued portion or the like can be improved.

We claim:

1. An ultrasonic flaw detection apparatus comprising:
   a probe which transmits an ultrasonic pulse at an angle with respect to a test surface of a test object and receives said ultrasonic pulse, which has been reflected by an acoustically discontinued portion in said test object, as an echo;
   scanning means for scanning said probe over a predetermined scanning zone on said test object and outputting a spatial position of said probe; and
   detecting means which accepts and stores said echo from said probe, and accepts and stores a spatial position of said probe from said scanning means, and detects said acoustically discontinued portion according to the spatial position of said probe and said echo, considering the spread of an ultrasonic beam attributable to diffraction so that values for multiple propagation paths between an origin and a reconstruction point are combined to indicate said acoustically discontinued portion, wherein said probe is driven by a transmission signal to transmit said ultrasonic pulse at a transmitting angle with respect to a test surface of a test object, and receives said ultrasonic pulse, which has been reflected by an acoustically discontinued portion in said test object, as an echo at a receiving angle, which is different from said transmitting angle, with respect to said test surface.

2. An ultrasonic flaw detection apparatus comprising:

a probe which transmits an ultrasonic pulse at an angle with respect to a test surface of a test object and receives said ultrasonic pulse, which has been reflected by an acoustically discontinued portion in said test object, as an echo;

scanning means for scanning said probe over a predetermined scanning zone on said test object and outputting a spatial position of said probe; and detecting means which accepts and stores said echo from said probe, and accepts and stores a spatial position of said probe from said scanning means, and detects said acoustically discontinued portion according to the spatial position of said probe and said echo, considering the spread of an ultrasonic beam attributable to diffraction so that values for multiple propagation paths between an origin and a reconstruction point are combined to indicate said acoustically discontinued portion, wherein said probe is driven by a transmission signal to transmit said ultrasonic pulse at a transmitting angle with respect to a test surface of a test object, and receives said ultrasonic pulse, which has been reflected by an acoustically discontinued portion in said test object, as an echo at a receiving angle, which is identical to said transmitting angle, with respect to said test surface.

3. An ultrasonic flaw detection apparatus comprising:

a probe which transmits an ultrasonic pulse at an angle with respect to a test surface of a test object and receives said ultrasonic pulse, which has been reflected by an acoustically discontinued portion in said test object, as an echo;

scanning means for scanning said probe over a predetermined scanning zone on said test object and outputting a spatial position of said probe; and detecting means which accepts and stores said echo from said probe, and accepts and stores a spatial position of said probe from said scanning means, and detects said acoustically discontinued portion according to the spatial position of said probe and said echo, considering the spread of an ultrasonic beam attributable to diffraction so that values for multiple propagation paths between an origin and a reconstruction point are combined to indicate said acoustically discontinued portion wherein said detecting means includes:

transmitting means for generating a transmission signal and outputting said transmission signal to said probe;

receiving means for accepting said received echo from said probe;

position detecting means for receiving a spatial position of said probe from said scanning means; and signal processing means for detecting said acoustically discontinued portion according to said stored spatial position of the probe and said stored echo, taking the spread of an ultrasonic beam attributable to diffraction into account.

4. An ultrasonic flaw detection apparatus according to claim 3, wherein said signal processing means includes:

raw data storing means for storing an echo received when said probe was scanned over a predetermined scanning zone, and coordinates of said probe corresponding to when said ultrasonic pulse was transmitted and when said echo was received;

candidate path identifying means for identifying a candidate of a transmitting and receiving round trip beam propagation path, which lies in an effective beam width of said probe, according to a fixed reconstruction point in a fixed image reconstruction zone of said test object and the coordinates of said probe stored in said raw data storing means;

amplitude adding means for determining the time at which an echo is to be received, obtaining the amplitude of an echo corresponding to said time from said raw data storing means, and adding each obtained echo amplitude on each candidate of said transmitting and receiving round trip beam propagation path; and image reconstruction means for outputting a value, which is obtained by adding said echo amplitudes over a fixed scanning zone of said probe, as a reconstructed image at said fixed reconstruction point.

5. An ultrasonic flaw detection apparatus according to claim 4, wherein said signal processing means outputs a reconstructed image at a fixed reconstruction point in said image reconstruction zone as a three-dimensional image.

6. An ultrasonic flaw detection apparatus according to claim 4 wherein, when the amplitude of the echo corresponding to said determined time has a significant value, said amplitude adding means adds said amplitude.

7. An ultrasonic flaw detection apparatus according to claim 4, wherein said effective beam width is a beam width of −3 dB.

8. An ultrasonic flaw detection apparatus according to claim 3, wherein said probe comprises a transmitting probe connected to said transmitting means and a receiving probe connected to said receiving means, and said scanning means comprises a transmission scanner provided for said transmitting probe and a reception scanner provided for said receiving probe.

9. An ultrasonic flaw detection apparatus comprising:

a probe which transmits an ultrasonic pulse at an angle with respect to a test surface of a test object and receives said ultrasonic pulse, which has been reflected by an acoustically discontinued portion in said test object, as an echo;

a scanning means for scanning said probe over a predetermined scanning zone on said test object and outputting a spatial position of said probe; and detecting means for accepting and storing said received echo from said probe, and receiving and storing the spatial position of said probe from said scanning means, and detecting said acoustically discontinued portion according to the spatial position of said probe and said echo, considering the spread of an ultrasonic beam attributable to diffraction so that values for multiple propagation paths between an origin and a reconstructed point are combined to indicate said acoustically discontinued portion, and further considering a mode conversion from a longitudinal wave to a transverse wave and a mode conversion from a transverse wave to a longitudinal wave when said ultrasonic pulse is reflected, wherein said probe is driven by a transmission signal to transmit said ultrasonic pulse at a transmitting angle with respect to a test surface of a test object, and receives said ultrasonic pulse, which has been reflected by an acoustically discontinued portion in said test object, as an echo at a receiving angle, which is different from said transmitting angle, with respect to said test surface.

10. An ultrasonic flaw detection apparatus comprising:

a probe which transmits an ultrasonic pulse at an angle with respect to a test surface of a test object and receives said ultrasonic pulse, which has been reflected by an acoustically discontinued portion in said test object, as an echo;

a scanning means for scanning said probe over a predetermined scanning zone on said test object and outputting a spatial position of said probe; and detecting means for
  accepting and storing said received echo from said probe, and receiving and storing the spatial position of said probe from said scanning means, and
  detecting said acoustically discontinued portion according to the spatial position of said probe and said echo, considering the spread of an ultrasonic beam attributable to diffraction so that values for multiple propagation paths between an origin and a reconstructed point are combined to indicate said acoustically discontinued portion, and further considering a mode conversion from a longitudinal wave to a transverse wave and a mode conversion from a transverse wave to a longitudinal wave when said ultrasonic pulse is reflected, wherein said probe is driven by a transmission signal to transmit an ultrasonic pulse at a transmitting angle with respect to a test surface of a test object, and receives said ultrasonic pulse, which has been reflected by an acoustically discontinued portion in said test object, as an echo at a receiving angle, which is identical to said transmitting angle, with respect to said test surface.

11. An ultrasonic flaw detection apparatus comprising:

a probe which transmits an ultrasonic pulse at an angle with respect to a test surface of a test object and receives said ultrasonic pulse, which has been reflected by an acoustically discontinued portion in said test object, as an echo;

a scanning means for scanning said probe over a predetermined scanning zone on said test object and outputting a spatial position of said probe; and detecting means for
  accepting and storing said received echo from said probe, and receiving and storing the spatial position of said probe from said scanning means, and
  detecting said acoustically discontinued portion according to the spatial position of said probe and said echo, considering the spread of an ultrasonic beam attributable to diffraction so that values for multiple propagation paths between an origin and a reconstructed point are combined to indicate said acoustically discontinued portion, and further considering a mode conversion from a longitudinal wave to a transverse wave and a mode conversion from a transverse wave to a longitudinal wave when said ultrasonic pulse is reflected, wherein said detecting means includes:
  transmitting means for generating a transmission signal and outputting said transmission signal to said probe,
  receiving means for accepting said received echo from said probe;
  position detecting means for receiving a spatial position of said probe from said scanning means; and
  signal processing means for detecting said acoustically discontinued portion according to said stored spatial position of the probe and said stored echo, considering the spread of an ultrasonic beam due to diffraction and a mode conversion from a longitudinal wave to a transverse wave and a mode conversion from a transverse wave to a longitudinal wave when said ultrasonic pulse is reflected.

12. An ultrasonic flaw detection apparatus according to claim 11, wherein said signal processing means includes:
  raw data storing means for storing an echo received when said probe was scanned over a predetermined scanning zone, and the coordinates of said probe when said ultrasonic pulse was transmitted and when said echo was received;
  candidate path identifying means for identifying a candidate of a transmitting and receiving round trip beam propagation path, which lies in an effective beam width of said probe, according to a fixed reconstruction point in a fixed image reconstruction zone of said test object and the coordinates of said probe stored in said raw data storing means;
  amplitude adding means for determining the time at which an echo is to be received, obtaining the amplitude of an echo corresponding to said time from said raw data storing means, and adding each obtained echo amplitude on each candidate of said transmitting and receiving round trip beam propagation path; and
  image reconstruction means for outputting a value, which is obtained by adding said echo amplitudes over a fixed scanning zone of said probe, as a reconstructed image at said fixed reconstruction point.

13. An ultrasonic flaw detection apparatus according to claim 12, wherein said signal processing means outputs a reconstructed image at a fixed reconstruction point in said image reconstruction zone as a three-dimensional image.

14. An ultrasonic flaw detection apparatus according to claim 12 wherein, when the amplitude of the echo corresponding to said determined time has a significant value, said amplitude adding means adds said amplitude.

15. An ultrasonic flaw detection apparatus according to claim 12, wherein said effective beam width is a beam width of −3 dB of an ultrasonic beam related to a transverse wave.

16. An ultrasonic flaw detection apparatus according to claim 12, wherein said effective beam width is a beam width of −3 dB of an ultrasonic beam related to a longitudinal wave.

17. An ultrasonic flaw detection apparatus according to claim 11, wherein
  said probe comprises a transmitting probe connected to said transmitting means and a receiving probe connected to said receiving means, and said scanning means comprises a transmission scanner provided for said transmitting probe and a reception scanner provided for said receiving probe.

18. An ultrasonic flaw detection method comprising:

scanning a probe over a predetermined scanning zone on a test object;

transmitting an ultrasonic pulse from said probe at an angle with respect to a test surface of said test object;

receiving, at said probe, said ultrasonic pulse, which has been reflected by an acoustically discontinued portion in said test object, as an echo;

accepting and storing said received echo from said probe, and receiving and storing the spatial position of said probe; and detecting said acoustically discontinued portion according to the spatial position of said probe and said echo considering the spread of an ultrasonic beam attributable to diffraction so that values for multiple propagation paths between an origin and a reconstruction point are combined to indicate said acoustically discontinued portion, wherein said transmitting step generates a transmission signal and outputs said transmission signal to said probe, then transmits an ultrasonic pulse at a transmitting angle with respect to a test surface of said test object, and said receiving step receives said ultrasonic pulse, which has been reflected by an acoustically discontinued portion in said test object, as an echo at a receiving angle, which is different from said transmitting angle, with respect to said test surface.

19. An ultrasonic flaw detection method comprising:

scanning a probe over a predetermined scanning zone on a test object;

transmitting an ultrasonic pulse from said probe at an angle with respect to a test surface of said test object;

receiving, at said probe, said ultrasonic pulse, which has been reflected by an acoustically discontinued portion in said test object, as an echo;

accepting and storing said received echo from said probe, and receiving and storing the spatial position of said probe; and detecting said acoustically discontinued portion according to the spatial position of said probe and said echo considering the spread of an ultrasonic beam attributable to diffraction so that values for multiple propagation paths between an origin and a reconstruction point are combined to indicate said acoustically discontinued portion, wherein said transmitting step generates a transmission signal and outputs said transmission signal to said probe, then transmits an ultrasonic pulse at a transmitting angle with respect to a test surface of said test object, and said receiving step receives said ultrasonic pulse, which has been reflected by an acoustically discontinued portion in said test object, as an echo at a receiving angle, which is identical to said transmitting angle, with respect to said test surface.

20. An ultrasonic flaw detection method comprising:

scanning a probe over a predetermined scanning zone on a test object;

transmitting an ultrasonic pulse from said probe at an angle with respect to a test surface of said test object;

receiving, at said probe, said ultrasonic pulse, which has been reflected by an acoustically discontinued portion in said test object, as an echo;

accepting and storing said received echo from said probe, and receiving and storing the spatial position of said probe; and detecting said acoustically discontinued portion according to the spatial position of said probe and said echo considering the spread of an ultrasonic beam attributable to diffraction so that values for multiple propagation paths between an origin and a reconstruction point are combined to indicate said acoustically discontinued portion, wherein said storing step stores an echo received when said probe was scanned over a predetermined scanning zone, and the coordinates of said probe when said ultrasonic pulse was transmitted and when said echo was received; and said detecting step includes the steps of:
identifying a candidate of a transmitting and receiving round trip beam propagation path which lies in an effective beam width of said probe according to a fixed reconstruction point in a fixed image reconstruction zone of said test object and said stored coordinates of said probe, determining the time at which an echo is to be received, obtaining the amplitude of an echo corresponding to said time, and adding each obtained echo amplitude on each candidate of said transmitting and receiving round trip beam propagation path; and outputting a value, which is obtained by adding said echo amplitude over a fixed scanning zone of said probe, as a reconstructed image at said fixed reconstruction point.

21. An ultrasonic flaw detection method according to claim 20, wherein said detecting step outputs a reconstructed image at a fixed reconstruction point in said image reconstruction zone as a three-dimensional image.

22. An ultrasonic flaw detection method according to claim 20 wherein, when the amplitude of the echo corresponding to said determined time has a significant value, said amplitude adding step adds said amplitude.

23. An ultrasonic flaw detection method according to claim 20, wherein said effective beam width is a beam width of −3 dB.

24. An ultrasonic flaw detection method comprising:

scanning a probe over a predetermined scanning zone on a test object;

transmitting an ultrasonic pulse from said probe at an angle with respect to a test surface of said test object;

receiving, at said probe, said ultrasonic pulse, which has been reflected by an acoustically discontinued portion in said test object, as an echo;

accepting and storing said received echo from said probe, and receiving and storing the spatial position of said probe; and detecting said acoustically discontinued portion according to the spatial position of said probe and said echo considering the spread of an ultrasonic beam attributable to diffraction so that values for multiple propagation paths between an origin and a reconstruction point are combined to indicate said acoustically discontinued portion, wherein said probe comprises a transmitting probe and a receiving probe, said scanning step is performed by a scanning means which comprises a transmission scanner provided for said transmitting probe and a reception scanner provided for said receiving probe, and the spatial position of said ultrasonic pulse transmitted by said transmitting probe is different from the spatial position of said echo received by said receiving probe.

25. An ultrasonic flaw detection method comprising:
scanning a probe over a predetermined scanning zone on a test object;
transmitting an ultrasonic pulse from said probe at an angle with respect to a test surface of said test object;
receiving said ultrasonic pulse, which has been reflected by an acoustically discontinued portion in said test object, as an echo;
accepting and storing said received echo from said probe, and receiving and storing the spatial position of said probe when said ultrasonic pulse was transmitted and when said echo was received; and
detecting said acoustically discontinued portion according to the spatial position of said probe and said echo, considering the spread of an ultrasonic beam attributable to diffraction so that values for multiple propagation paths between an origin and a reconstruction point are combined to indicate said acoustically discontinued point, and further considering a mode conversion from a longitudinal wave to a transverse wave and a mode conversion from a transverse wave to a longitudinal wave which take place when said ultrasonic pulse is reflected, wherein
said transmitting step generates a transmission signal and outputs said transmission signal to said probe, then transmits an ultrasonic pulse at a transmitting angle with respect to a test surface of said test object, and
said receiving step receives said ultrasonic pulse, which has been reflected by an acoustically discontinued portion in said test object, as an echo at a receiving angle, which is different from said transmitting angle, with respect to said test surface.

26. An ultrasonic flaw detection method comprising:
scanning a probe over a predetermined scanning zone on a test object;
transmitting an ultrasonic pulse from said probe at an angle with respect to a test surface of said test object;
receiving said ultrasonic pulse, which has been reflected by an acoustically discontinued portion in said test object, as an echo;
accepting and storing said received echo from said probe, and receiving and storing the spatial position of said probe when said ultrasonic pulse was transmitted and when said echo was received; and
detecting said acoustically discontinued portion according to the spatial position of said probe and said echo, considering the spread of an ultrasonic beam attributable to diffraction so that values for multiple propagation paths between an origin and a reconstruction point are combined to indicate said acoustically discontinued point, and further considering a mode conversion from a longitudinal wave to a transverse wave and a mode conversion from a transverse wave to a longitudinal wave which take place when said ultrasonic pulse is reflected, wherein
said transmitting step generates a transmission signal and outputs said transmission signal to said probe, then transmits an ultrasonic pulse at a transmitting angle with respect to a test surface of said test object, and
said receiving step receives said ultrasonic pulse, which has been reflected by an acoustically discontinued portion in said test object, as an echo at a receiving angle, which is identical to said transmitting angle, with respect to said test surface.

27. An ultrasonic flaw detection method comprising:
scanning a probe over a predetermined scanning zone on a test object;
transmitting an ultrasonic pulse from said probe at an angle with respect to a test surface of said test object;
receiving said ultrasonic pulse, which has been reflected by an acoustically discontinued portion in said test object, as an echo;
accepting and storing said received echo from said probe, and receiving and storing the spatial position of said probe when said ultrasonic pulse was transmitted and when said echo was received; and
detecting said acoustically discontinued portion according to the spatial position of said probe and said echo, considering the spread of an ultrasonic beam attributable to diffraction so that values for multiple propagation paths between an origin and a reconstruction point are combined to indicate said acoustically discontinued point, and further considering a mode conversion from a longitudinal wave to a transverse wave and a mode conversion from a transverse wave to a longitudinal wave which take place when said ultrasonic pulse is reflected,
wherein said storing step stores an echo received when said probe was scanned over a predetermined scanning zone, and the coordinates of said probe when said ultrasonic pulse was transmitted and when said echo was received; and
said detecting step includes the steps of:
identifying a candidate of a transmitting and receiving round trip beam propagation path which lies in an effective beam width of said probe according to a fixed reconstruction point in a fixed image reconstruction zone of said test object and said stored coordinates of said probe,
determining the time at which an echo is to be received, obtaining the amplitude of an echo corresponding to said time, and adding each obtained echo amplitude on each candidate of said transmitting and receiving round trip beam path; and
outputting a value, which is obtained by adding said echo amplitude over a fixed scanning zone of said probe, as a reconstructed image at said fixed reconstruction point.

28. An ultrasonic flaw detection method according to claim 27, wherein said detecting step outputs a reconstructed image at a fixed reconstruction point in said image reconstruction zone as a three-dimensional image.

29. An ultrasonic flaw detection method according to claim 27 wherein, when the amplitude of the echo corresponding to said determined time has a significant value, said amplitude adding step adds said amplitude.

30. An ultrasonic flaw detection method according to claim 27, wherein said effective beam width is a beam width of −3 dB of an ultrasonic beam related to a transverse wave.

31. An ultrasonic flaw detection method according to claim 27, wherein said effective beam width is a beam width of −3 dB of an ultrasonic beam related to a longitudinal wave.

32. An ultrasonic flaw detection method comprising:
scanning a probe over a predetermined scanning zone on a test object;
transmitting an ultrasonic pulse from said probe at an angle with respect to a test surface of said test object;

receiving said ultrasonic pulse, which has been reflected by an acoustically discontinued portion in said test object, as an echo;

accepting and storing said received echo from said probe, and receiving and storing the spatial position of said probe when said ultrasonic pulse was transmitted and when said echo was received; and detecting said acoustically discontinued portion according to the spatial position of said probe and said echo, considering the spread of an ultrasonic beam attributable to diffraction so that values for multiple propagation paths between an origin and a reconstruction point are combined to indicate said acoustically discontinued point, and further considering a mode conversion from a longitudinal wave to a transverse wave and a mode conversion from a transverse wave to a longitudinal wave which take place when said ultrasonic pulse is reflected, wherein said probe comprises a transmitting probe and a receiving probe, and said scanning step is performed by a scanning means which comprises a transmitting scanner provided for said transmitting probe and a reception scanner provided for said receiving probe, and the spatial position of said ultrasonic pulse transmitted by said transmitting probe is different from the spatial position of said echo received by said receiving probe.

* * * * *